(12) United States Patent
Scanlan et al.

(10) Patent No.: US 7,521,543 B2
(45) Date of Patent: Apr. 21, 2009

(54) A34 AND A33-LIKE 3 DNA, PROTEINS, ANTIBODIES THERETO AND METHODS OF TREATMENT USING SAME

(75) Inventors: Matthew Scanlan, New York, NY (US); Cynthia Scanlan, legal representative, Princeton Junction, NY (US); Gerd Ritter, New York, NY (US); Lloyd Old, New York, NY (US); Achim Jungbluth, New York, NY (US)

(73) Assignee: Ludwig Institute for Cancer Research, New York, NY (US)

( * ) Notice: Subject to any disclaimer, the term of this patent is extended or adjusted under 35 U.S.C. 154(b) by 0 days.

(21) Appl. No.: 10/532,489

(22) PCT Filed: Oct. 23, 2003

(86) PCT No.: PCT/US03/33707

§ 371 (c)(1),
(2), (4) Date: Feb. 21, 2006

(87) PCT Pub. No.: WO2004/037999

PCT Pub. Date: May 6, 2004

(65) Prior Publication Data

US 2006/0292154 A1    Dec. 28, 2006

Related U.S. Application Data

(60) Provisional application No. 60/420,285, filed on Oct. 23, 2002.

(51) Int. Cl.
*C12P 21/08* (2006.01)
(52) U.S. Cl. .................................................. 530/388.8

(58) Field of Classification Search .................. None
See application file for complete search history.

(56) References Cited

U.S. PATENT DOCUMENTS 5,786,465 A    7/1998    Jacobs et al.

FOREIGN PATENT DOCUMENTS

| WO | WO99/26972 | 6/1999 |
|---|---|---|
| WO | WO 99/26972 | * 6/1999 |
| WO | WO99/60020 | 11/1999 |

OTHER PUBLICATIONS

Nustad K, Paus E, Kierulf B, Bormer OP. Specificity and affinity of 30 monoclonal antibodies against alpha-fetoprotein. Tumour Biol., 1998;19(4):293-300, (Abstract only).*
Rudikoff et al. Proc Natl Acad Sci USA 1982 vol. 79 p. 1979.*
MacCallum et al. J. Mol. Biol. (1996) 262, 732-745.*
Pascalis et al. The Journal of Immunology (2002) 169, 732-745.*
Casset et al. (2003) BBRC 307, 198-205.*
Vajdos et al. Journal of Molecular Biology. (2002) 320, 415-428.*
Chen et al. J. Mol. Bio. (1999) 293, 865-881.*
Wu et al. J. Mol. Biol. (1999) 294, 151-162.*
Holm et al. Molecular Immunology, (2007) 44, 1075-1084.*

* cited by examiner

*Primary Examiner*—Larry R. Helms
*Assistant Examiner*—Meera Natarajan
(74) *Attorney, Agent, or Firm*—Crowell & Moring LLP

(57) ABSTRACT

Polynucleotide molecules and polypeptide molecules A34 and A33-like 3 are described, as well as antibodies to polypeptide molecules A34 and A33like 3. Also described are methods of detecting cancers expressing these polypeptides, and methods and kits for diagnosing said cancers, and methods of inhibiting effects of a cancer in a patient.

20 Claims, 24 Drawing Sheets

FIG. 1 mRNA Expression Profiles of A34
End point RT-PCR
Stomach Testis
Origene cDNA Panel (24 Normal Tissues)

Analysis of A34 mRNA Expression in Normal and Malignant Tissues

FIG. 3

A34 Protein: A34 vs A33

```
  1 MVFAFWKVFLILSCLAGQVSVVQVTIPDGFVNVTVGSNVTLICIYTTTVASREQLSIQWS    A34
  1 MVGKMWPVLWTLCAVRVTVDAISVETPQDVLRASQGKSVTLPCTYHTSTSSREGL-IQWD    A33
    MV  W V L      V   V P    G  VTL C Y T   SRE L  IQW

61 FFHKKEMEPISIYFSQGGQAVAIGQFKDRITGSN--DPGNASITISHMQPADSGIYICDV    A34
 60 KLLLTHTERVVIWPFSNKNYIHGELYKNRVSISNNAEQSDASITIDQLTMADNGTYECSV    A33
                 I         K R   SN    ASITI     AD  G Y C V

119 NNPPDFLGQNQGILNVSVLVKPSKPLCSVQGRPETGHTISLSCLSALGTPSPVYYWHKLE    A34
120 SLMSDLEGNTKSRVRLLVLVPPSKPECGIEGETIIGNNIQLTCQSKEGSPTPQYSWKRY-    A33
      D G          VLV PSKP C  G   ILCS  G P P Y W

179 GRDIVPVKENF-NPTTGILV-IGNLTNFEQGYYQCTAINRLGNSSCEIDLTSSHPEVGII    A34
179 --NILNQEQPLAQPASGQPVSLKNISTDTSGYYICTSSNEEGTQFCNITVAVRSPSMNVA    A33
       I        P G V  N    GYY CT N G  CI       P

237 --VGALIGSLVGAAIIISVVCFARNKAKAKERNSKTIAELEPMTKINPRGESEAMPRE      A34
237 LYVGIAVG-VVAALIIGIIIYCCC---CRGKD-------------------K           A33
    VG  G V A III                 K

295 DATQLEVTLPSSIHETGPDTIQEPDYEPKPTQEPAPEPAPGSEPMAVPDLDIELELEPET    A34
266 ---------------DNTEDKE-DARPNREAYEEP--------PEQLRELSREREE        A33
                   D        P E  EP       P     EL  E  E

355 QSELEPEPEPEPESEPGVVVEPLSEDEKGVVKA                              A34
298 EDDYRQEEQRSTGRES---PDHLDQ--------                              A33
        E                     L
```

A34: Nucleic acid sequence (SEQ ID NO: 3):

CTTCTTGTGGTAGGGACCTCTCCTCAGTATTTGAAACTAACCAGCATCTGACAGA
TTTCGAATTTGTAAAAAATACCCTCGAAGATTCAGGAATGAAGCTTCTGTGTGAA
GGATTAAAACAGCCCAACTGTGTATTACAGACATTGAGGTGGTACCGGTGCCTTA
TCTCTTCTGCTTCTTGTGGGGCTCTAGCAGCTGTTCTTAGCACCAGTCAGTGGCT
CACTGAACTGGAATTTAGTGAGACAAAACTGGAAGCTTCAGCTTTGAAATTGCTC
TATGGAGGCTTAAAAGATCCAAATTGCAAATTACAGAAGCTCAACTTGCAGTTTT
CTTTATCTGTAACCGCTGCAAAACTTCCAGTTGGAATGGTTGGAAATTGTTCTGG
TTTCTCGGGATCATTGGTGCAATCTCATTTTGGCTACTGTCAGGACAGTTCTTTC
AAATGTGATCTTTGTAAGCTGCTCTGGCCTTCCACCAGAGTTGCTGCTGCAAAGG
ATTGTGGGAGTCCTAAGTCCTTCCTATCAGAAGGGCTGAACTGGGCAGGAAGACT
TGAGGCAGTGGAGGAGGTTTTGGGGTTGGGGGTGCTTGTACAGCCCGGTGACCCA
GCATCTCAGGGTGGGGGGCATTGTGAAAACTATGGGTCTTTTAGAGACTTGGTGG
ACTTAGAAGTCAAGGCAGAACCAAGCCTGAGAAAAGGTGGTATGGATCTCCAGAG
ACCCACCCTACAAGTTGTCCTCCTTTGCAAAATCTTCTCCCTCAAACTATTTCTC
TTTATTGCATTGCCTAATTCTCCTGGTCAGGTTAGTGTGGTGCAAGTGACCATCC
CAGACGGTTTCGTGAACGTGACTGTTGGATCTAATGTCACTCTCATCTGCATCTA
CACCACCACTGTGGCCTCCCGAGAACAGCTTTCCATCCAGTGGTCTTTCTTCCAT
AAGAAGGAGATGGAGCCAATTTCTATTTACTTTTCTCAAGGTGGACAAGCTGTAG
CCATCGGGCAATTTAAAGATCGAATTACAGGGTCCAACGATCCAGGTAATGCATC
TATCACTATCTCGCATATGCAGCCAGCAGACAGTGGAATTTACATCTGCGATGTT
AACAACCCCCCAGACTTTCTCGGCCAAAACCAAGGCATCCTCAACGTCAGTGTGT
TAGTGAAACCTTCTAAGCCCCTTTGTAGCGTTCAAGGAAGACCAGAAACTGGCCA
CACTATTTCCCTTTCCTGTCTCTCTGCGCTTGGAACACCTTCCCCTGTGTACTAC
TGGCATAAACTTGAGGGAAGAGACATCGTGCCAGTGAAAGAAAACTTCAACCCAA
CCACCGGGATTTTGGTCATTGGAAATCTGACAAATTTTGAACAAGGTTATTACCA
GTGTACTGCCATCAACAGACTTGGCAATAGTTCCTGCGAAATCGATCTCACTTCT
TCACATCCAGAAGTTGGAATCATTGTTGGGGCCTTGATTGGTAGCCTGGTAGGTG
CCGCCATCATCATCTCTGTTGTGTGCTTCGCAAGGAATAAGGCAAAAGCAAAGGC
AAAAGAAAGAAATTCTAAGACCATCGCGGAACTTGAGCCAATGACAAAGATAAAC
CCAAGGGGAGAAAGCGAAGCAATGCCAAGAGAAGACGCTACCCAACTAGAAGTAA
CTCTACCATCTTCCATTCATGAGACTGGCCCTGATACCATCCAAGAACCAGACTA
TGAGCCAAAGCCTACTCAGGAGCCTGCCCCAGAGCCTGCCCCAGGATCAGAGCCT
ATGGCAGTGCCTGACCTTGACATCGAGCTGGAGCTGGAGCCAGAAACGCAGTCGG
AATTGGAGCCAGAGCCAGAGCCAGAGCCAGAGTCAGAGCCTGGGGTTGTAGTTGA
GCCCTTAAGTGAAGATGAAAAGGGAGTGGTTAAGGCATAG

A34 amino acid sequence (SEQ ID NO: 4):

MDLQRPTLQVVLLCKIFSLKLFLFIALPNSPGQVSVVQVTIPDGFVNVTVGSNVT
LICIYTTTVASREQLSIQWSFFHKKEMEPISIYFSQGGQAVAIGQFKDRITGSND
PGNASITISHMQPADSGIYICDVNNPPDFLGQNQGILNVSVLVKPSKPLCSVQGR
PETGHTISLSCLSALGTPSPVYYWHKLEGRDIVPVKENFNPTTGILVIGNLTNFE
QGYYQCTAINRLGNSSCEIDLTSSHPEVGIIVGALIGSLVGAAIIISVVCFARNK
AKAKAKERNSKTIAELEPMTKINPRGESEAMPREDATQLEVTLPSSIHETGPDTI
QEPDYEPKPTQEPAPEPAPGSEPMAVPDLDIELELEPETQSELEPEPEPEPESEP
GVVVEPLSEDEKGVVKA

FIG. 4

A34 clone nucleic acid sequence (SEQ. ID NO: 5)

ACTGTTGGATCTAATGTCACTCTCATCTGCATCTACACCACCACTGTGGCCTCCCGAGA
ACAGCTTTCCATCCAGTGGTCTTTCTTCCATAAGAAGGAGATGGAGCCAATTTCTATTT
ACTTTTCTCAAGGTGGACAAGCTGTAGCCATCGGGCAATTTAAAGATCGAATTACAGGG
TCCAACGATCCAGGTAATGCATCTATCACTATCTCGCATATGCAGCCAGCAGACAGTGG
AATTTACATCTGCGATGTTAACAACCCCCAGACTTTCTCGGCCAAAACCAAGGCATCC
TCAACGTCAGTGTGTTAGTGAAACCTTCTAAGCCCCTTTGTAGCGTTCAAGGAAGACCA
GAAACTGGCCACACTATTTCCCTTTCCTGTCTCTCTGCGCTTGGAACACCTTCCCCTGT
GTACTACTGGCATAAACTTGAGGGAAGAGACATCGTGCCAGTGAAAGAAACTTCAACC
CAACCACCGGGATTTTGGTCATTGGAAATCTGACAAATTTTGAACAAGGTTATTACCAG
TGTACTGCCATCAACAGACTTGGCAATAGTTCCTGCGAAATCGATCTCACTTCTTCACA
TCCAGAAGTTGGAATCATTGTTGGGGCCTTGATTGGTAGCCTGGTAGGTGCCGCCATCA
TCATCTCTGTTGTGTGCTTCGCAAGGAATAAGGCAAAAGCAAAGGCAAAAGAAAGAAAT
TCTAAGACCATCGCGGAACTTGAGCCAATGACAAAGATAAACCCAAGGGGAGAAAGCGA
AGCAATGCCAAGAGAAGACGCTACCCAACTAGAAGTAACTCTACCATCTTCCATTCATG
AGACTGGCCCTGATACCATCCAAGAACCAGACTATGAGCCAAAGCCTACTCAGGAGCCT
GCCCCAGAGCCTGCCCCAGGATCAGAGCCTATGGCAGTGCCTGACCTTGACATCGAGCT
GGAGCTGGAGCCAGAAACGCAGTCGGAATTGGAGCCAGAGCCAGAGCCAGAGCCAGAGT
CAGAGCCTGGGGTTGTAGTTGAGCCCTTAAGTGAAGATGAAA

A34 clone amino acid sequence (SEQ. ID NO: 6)

TVGSNVTLICIYTTTVASREQLSIQWSFFHKKEMEPISIYFSQGGQAVAIGQFKDRITG
SNDPGNASITISHMQPADSGIYICDVNNPPDFLGQNQGILNVSVLVKPSKPLCSVQGRP
ETGHTISLSCLSALGTPSPVYYWHKLEGRDIVPVKENFNPTTGILVIGNLTNFEQGYYQ
CTAINRLGNSSCEIDLTSSHPEVGIIVGALIGSLVGAAIIISVVCFARNKAKAKAKERN
SKTIAELEPMTKINPRGESEAMPREDATQLEVTLPSSIHETGPDTIQEPDYEPKPTQEP
APEPAPGSEPMAVPDLDIELELEPETQSELEPEPEPEPESEPGVVVEPLSEDE

FIGURE 5

A33-like 3 polynucleotide sequence (SEQ ID NO: 7):

```
TGTGCAGGCAACAGGAAACAAATACAGAGGGCAGAGCAAGGATTGGTCAGGACGG
GCTTAGTGAGAAAGGCTCTGAACGAGACACACACCAGCTGCAGCTTCGTACTGAC
GCCTGCCAGCTCCTACACACCTTCCTGGGCAACTGCCAGCGGGGCAAGGCAGGCC
TGGGGCCACCCTGCAGGCAGTGTCTGGGCCCTCAGCTCCCCCTCCCTCCACCTAC
CCCCTCACACCCACCACTACGACCCCACGGGATACCCAGCCCAGACGGAGGAAAC
ACCGAGCCTAGAGACATGAGAGTTGGAGGAGCATTCCACCTTCTACTCGTGTGCC
TGAGCCCAGCACTGCTGTCTGCTGTGCGGATCAACGGGGATGGACAGGAGGTCCT
GTACCTGGCAGAAGGTGATAATGTGAGGCTGGGCTGCCCCTACGTCCTGGACCCT
GAGGACTATGGTCCCAATGGGCTGGACATCGAGTGGATGCAGGTCAACTCAGACC
CCGCCCACCACCGAGAGAACGTGTTCCTTAGTTACCAGGACAAGAGGATCAACCA
TGGCAGCCTTCCCCATCTGCAGCAGAGGGTCCGCTTTGCAGCCTCAGACCCAAGC
CAGTACGATGCCTCCATCAACCTCATGAACCTGCAGGTATCTGATACAGCCACTT
ATGAGTGCCGGGTGAAGAAGACCACCATGGCCACCCGGAAGGTCATTGTCACTGT
CCAAGCACGACCTGCAGTGCCCATGTGCTGGACAGAGGGCCACATGACATATGGC
AACGATGTGGTGCTGAAGTGCTATGCCAGTGGGGGCTCCCAGCCCCTCTCCTACA
AGTGGGCCAAGATCAGTGGGCACCATTACCCCTATCGAGCTGGGTCTTACACCTC
CCAGCACAGCTACCACTCAGAGCTGTCCTACCAGGAGTCCTTCCACAGCTCCATA
AACCAAGGCCTGAACAATGGGGACCTGGTGTTGAAGGATATCTCCAGAGCAGATG
ATGGGCTGTATCAGTGCACAGTGGCCAACAACGTGGGCTACAGTGTTTGTGTGGT
GGAGGTGAAGGTCTCAGACTCCCGGCGTATAGGCGTGATCATCGGCATCGTCCTG
GGCTCTCTGCTCGCGCTGGGCTGCCTGGCCAGAGGACGCCGTGGCGCCCGGGTGC
AAGGCCAGCGGGCGCGGCAGCCGCGTCACCCACCTCCTGGGGTACCCGACGCAGA
ACGTCAGCCGCTCCCTGCGCCGCAATACGCGCCTCCCCCTGCGGCGGCCCCGAG
GACGTGGCCCTGGCGCCCTGCACCGCCGCCGCCGCCTGCGAAGCGGGCCCCTCCC
CGGTCTACGTCAAGGTCAAGAGCGCGGAGCCGGCTGACTGCGCCGAGGGGCCGGT
GCAGTGCAAGAACGGCCTCTTGGTGTGA
```

A33-like 3 polypeptide sequence (SEQ ID NO: 8):

```
MRVGGAFHLLLVCLSPALLSAVRINGDGQEVLYLAEGDNVRLGCPYVLDPEDYGP
NGLDIEWMQVNSDPAHHRENVFLSYQDKRINHGSLPHLQQRVRFAASDPSQYDAS
INLMNLQVSDTATYECRVKKTTMATRKVIVTVQARPAVPMCWTEGHMTYGNDVVL
KCYASGGSQPLSYKWAKISGHHYPYRAGSYTSQHSYHSELSYQESFHSSINQGLN
NGDLVLKDISRADDGLYQCTVANNVGYSVCVVEVKVSDSRRIGVIIGIVLGSLLA
LGCLARGRRGARVQGQRARQPRHPPPGVPDAERQPLPAPQYAPPPCGGPEDVALA
PCTAAAACEAGPSPVYVKVKSAEPADCAEGPVQCKNGLLV
```

FIG. 6

A33-like 3 vs A33:

Score = 67.4 bits (163), Expect = 2e-10
Identities = 63/232 (27%), Positives = 95/232 (40%), Gaps = 35/232 (15%)

```
Query:  29  QEVLYLAEGDNVRLGCPYVLDPEDYGPNGLDIEWMQVNSDPAHHRENVFLSYQDKRINHG  88
            Q+VL  ++G +V L C Y        GL I+W ++      H   V   + +K   HG
A33  :  28  QDVLRASQGKSVTLPCTYHTSTSSR--EGL-IQWDKLLL--THTERVVIWPFSNKNYIHG  82

Query:  89  SLPHLQQRVRFAASDPSQYDASINLMNLQVSDTATYECRVKKTT----MATRKVIVTVQA  144
            L   + RV + ++  Q DASI +  L ++D  TYEC V  +         +V + V
A33  :  83  EL--YKNRVSIS-NNAEQSDASITIDQLTMADNGTYECSVSLMSDLEGNTKSRVRLLVLV  139

Query: 145  RPAVPMCWTEGHMTYGNDVVLKCYASGGSQPLSYKWAKISGHHYPYRAGSYTSQHSYHSE  204
            P+ P C  EG    GN++ L C +  GS      Y W + +
A33  : 140  PPSKPECGIEGETIIGNNIQLTCQSKEGSPTPQYSWKRYN--------------------  179

Query: 205  LSYQESFHSSINQGLNNGDLVLKDISRADDGLYQCTVANNVGYSVCVVEVKV  256  (SEQ. ID NO: 9)
            + QE   +Q +   + LK+IS    G Y CT +N G   C + V V
A33  : 180  ILNQE---QPLAQPASGQPVSLKNISTDTSGYYICTSSNEEGTQFCNITVAV  228  (SEQ. ID NO: 10)
```

FIG. 7

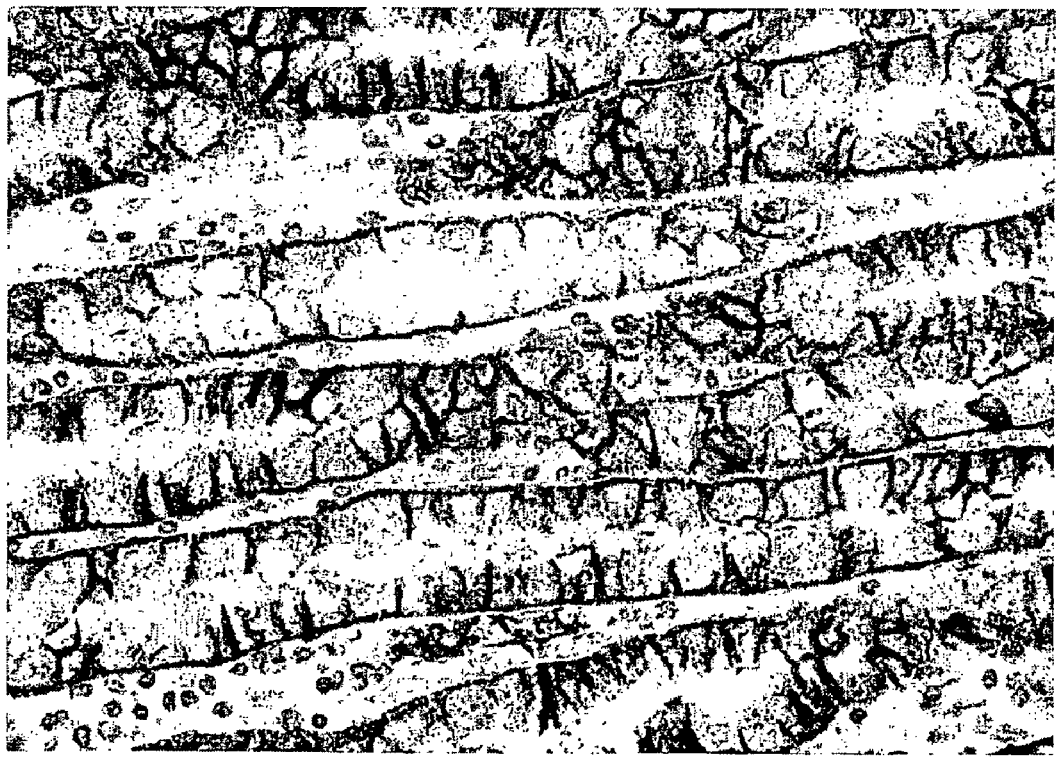
FIG. 12

TA-Bl-mur.A34 Light Chain Clone: 209-970

```
atgaggtgccttgttcagtttctggggctgcttgtgctctggatccct
 M  R  C  L  V  Q  F  L  G  L  L  V  L  W  F  P
ggagccattggggatattgtgatgactcaggctgcaccctctgtccctgtcactcctgga
 G  A  I  G  D  I  V  M  T  Q  A  A  P  S  V  P  V  T  P  G
gagtcagtatccatctcctgcaggtctagtacgagtctcctgcatagtaatggcaacact
 E  S  V  S  I  S  C  R  S  S  T  S  L  L  H  S  N  G  N  T
tacttgtattggttcctgcagaggccaggccagtctcctcagctcctgatatatcggatg
 Y  L  Y  W  F  L  Q  R  P  G  Q  S  P  Q  L  L  I  Y  R  M
tccaaccttgcctcaggagtcccagacaggttcagtggcagtgggtcaggaactgcttc
 S  N  L  A  S  G  V  P  D  R  F  S  G  S  G  S  G  T  A  F
acactgagaatcagtagagtggaggctgaggatgtgggtatttattactgt
 T  L  R  I  S  R  V  E  A  E  D  V  G  I  Y  Y  C  M  Q  H
            ttcggagggggggaccaaactggaaataaaacgg
 L  E  Y  P  F  T  G  G  G  T  K  L  E  I  K  R
```

(SEQ ID NO: 20)
(SEQ ID NO: 21)

TA-Bl-A34 Heavy Chain 4 Clone: 209-970

```
atgaactttggggttcagcttggttttccttgcccttatttaaaaggt
 M  N  F  G  F  S  L  V  F  L  A  L  I  L  K  G
gtccagtgtgaggtggagctggtggagtctggggggaggcctagtgcagcctggagggtcc
 V  Q  C  E  V  E  L  V  E  S  G  G  G  L  V  Q  P  G  G  S
ctgaaactctcctgtgcagcctctggattcaccttcagtacttttggcatgtcttgggtt
 L  K  L  S  C  A  A  S  G  F  T  F  S  T  F  G  M  S  W  V
cgccagactccagacaagaggctggagttggtcgcaaccattaatagtaatggtggtagg
 R  Q  T  P  D  K  R  L  E  L  V  A  T  I  N  S  N  G  G  R
acctattatctagacagtgtgaagggccgattcaccatctccagagaaaatgccaagaac
 T  Y  Y  L  D  S  V  K  G  R  F  T  I  S  R  E  N  A  K  N
accctgtacctgcaaatgagcagtctgaagtctgaggacacagccatgtattactgtgca
 T  L  Y  L  Q  M  S  S  L  K  S  E  D  T  A  M  Y  Y  C  A
aga                                        ctggggccaagggactctg
 R  D  G  L  L  R  D  S  A  W  F  A  Y  W  G  Q  G  T  L
gtcactgtctctgca        (SEQ ID NO: 22)
 V  T  V  S  A         (SEQ ID NO: 23)
```

FIG. 21

TA-B1-mur.A34 Light Chain Clone: 209-564

```
atgaggtgccttgctcagcttctggggctgcttgtgctctggatccct
 M  R  C  L  A  Q  L  L  C  L  L  V  L  W  I  P
ggagccattggggatattgtgatgactcaggctgcaccctctgtacctgtcactcctgga
 G  A  I  G  D  I  V  M  T  Q  A  A  P  S  V  P  V  T  P  G
gagtcagtatccatctcctgcaggtctagtacgagtctcctgcatggtaatggcaacact
 E  S  V  S  I  S  C  R  S  S  T  S  L  L  H  G  N  G  N  T
tacttgtattggttcctgcagaggccaggccagtctcctcagctcctgatatatcggatg
 Y  L  Y  W  F  L  Q  R  P  G  Q  S  P  Q  L  L  I  Y  R  M
tccaaccttgcctcaggagtcccagacaggttcagtggcagtgggtcaggaactgctttc
 S  N  L  A  S  G  V  P  D  R  F  S  G  S  G  S  G  T  A  F
acactgagaatcagtagagtggaggctgaggatgtgggtatttattactgtatgcaacat
 T  L  R  I  S  R  V  E  A  E  D  V  G  I  Y  Y  C  M  Q  H
ctagaatatccattcacgttcggaggggggaccaagctggaaataaaacgg
 L  E  Y  P  F  T  F  G  G  G  T  K  L  E  I  K  R
(SEQ ID NO:  24)
(SEQ ID NO:  25)
```

TA-B1-A34 Heavy Chain 4   Clone: 209-564

```
atggactttgggttcagcttggttttccttgcccttatttttaaaaggt
 M  D  F  G  F  S  L  V  F  L  A  L  I  L  K  G
gtccagtgtgaggtggagctggtggagtctggggaggcttagtgcagcctggagggtcc
 V  Q  C  E  V  E  L  V  E  S  G  G  G  L  V  Q  P  G  G  S
ctgaaactctcctgtgcagcctctggattcaccttcagtagttatggcatgtcttgggtt
 L  K  L  S  C  A  A  S  G  F  T  F  S  S  Y  G  M  S  W  V
cgccagactccagacaagaggctggagttggtcgcaaccattaatagtaatggtggtagg
 R  Q  T  P  D  K  R  L  E  L  V  A  T  I  N  S  N  G  G  R
acctattatctagacagtgtgaagggccgattcaccatctccagagacaatgccaagaac
 T  Y  Y  L  D  S  V  K  G  R  F  T  I  S  R  D  N  A  K  N
accctgtacctgcaaatgagcagtctgaagtctgaggacacagccatgtattactgtgca
 T  L  Y  L  Q  M  S  S  L  K  S  E  D  T  A  M  Y  Y  C  A
agagatggactccttagggattctgcttggtttgcttactggggccaagggactctg
 R  D  G  L  L  R  D  S  A  W  F  A  Y  W  G  Q  G  T  L
gtcactgtctctgca
 V  T  V  S  A
(SEQ ID NO:  26)
(SEQ ID NO:  27)
```

FIG. 22

TA-B1-mur.A34 Light Chain Clone: 209-342

```
atgagggcccctgctcagattttttggattcttgttgctctggttccca
M  R  A  P  A  Q  I  F  G  F  L  L  L  W  F  P
ggtgccagatgtgaaatccagatgacccagtctccatcctctatgtctgcatctctggga
G  A  R  C  E  I  Q  M  T  Q  S  P  S  S  M  S  A  S  L  G
gacagaataaccatcacttgccaggcaactcaagacattgtcaagaatttaaactggtat
D  R  I  T  I  T  C  Q  A  T  Q  D  I  V  K  N  L  N  W  Y
cagcagaaaccagggaaaccccttcaatcctgatctattatgcaactgaactggcagaa
Q  Q  K  P  G  K  P  P  S  I  L  I  Y  Y  A  T  E  L  A  E
ggggtcccatcaaggttcagtggcagtgggtctgggtcagactattctctgacaatcagc
G  V  P  S  R  F  S  G  S  G  S  G  S  D  Y  S  L  T  I  S
aacctggagtctgaagattttgcagactattactgt
N  L  E  S  E  D  F  A  D  Y  Y  C  L  Q  F  Y  D  F  P  L
ttcggtgctgggaccaagctggagctgaaacgg    (SEQ ID NO:  28)
T  F  G  A  G  T  K  L  E  L  K  R    (SEQ ID NO:  29)
```

TA-B1-mur.A34 Heavy Chain    Clone:209-342

```
atgggatggagctatatcatcttctttctggtagcaacagctacaggt
M  G  W  S  Y  I  I  F  F  L  V  A  T  A  T  G
gtgcactcccaggtccagctgcagcagtctgggcctgagctggtgaggcctggggtctca
V  H  S  Q  V  Q  L  Q  Q  S  G  P  E  L  V  R  P  G  V  S
gtgaagatttcctgcaagggttccggctacacattcactgattatgctacgcactgggtg
V  K  I  S  C  K  G  S  G  Y  T  F  T  D  Y  A  T  H  W  V
aggcagagtcatgcaaagagtctagagtggattggagttattagtagttactctggtaat
R  Q  S  H  A  K  S  L  E  W  I  G  V  I  S  S  Y  S  G  N
acaaagtacaaccagaactttaaggacaaggccacaatgactgtagacaaatcctccagc
T  K  Y  N  Q  N  F  K  D  K  A  T  M  T  V  D  K  S  S  S
acagcctatatggaacttgccagattgacatctgaggattctgccatgtattactgtgca
T  A  Y  M  E  L  A  R  L  T  S  E  D  S  A  M  Y  Y  C  A
agaRYDYDVRYYAMDYtggggtcaaggaacctcagtc
R  Y  D  Y  D  V  R  Y  Y  A  M  D  Y  W  G  Q  G  T  S  V
accgtctcctca    (SEQ ID NO:  30)
T  V  S  S      (SEQ ID NO:  31)
```

FIG. 23

TA-B1-mur.A34 light chain clone 209-970

CDR1: SNGNTYLY    (SEQ ID NO: 32)
    CDR2: RMSNLAS    (SEQ ID NO: 33)
    CDR3: MQHLEYPFT    (SEQ ID NO: 34)

TA-B1-A34 heavy chain clone 4 209-970

CDR1: TFGMS    (SEQ ID NO: 35)
    CDR2: TINSNGGRTYYLDSVKG    (SEQ ID NO: 36)
    CDR3: DGGLLRDSAWFAY    (SEQ ID NO: 37)

TA-B1-mur.A34 light chain clone 209-564

CDR1: GNGNTYLY    (SEQ ID NO: 38)
    CDR2: RMSNLAS    (SEQ ID NO: 39)
    CDR3: MQHLEYPFT    (SEQ ID NO: 40)

TA-B1-A34 heavy chain clone 4 209-564

CDR1: SYGMS    (SEQ ID NO: 41)
    CDR2: TINSNGGRTYYLDSVKG    (SEQ ID NO: 42)
    CDR3: DGGLLRDSAWFAY    (SEQ ID NO: 43)

TA-B1-mur.A34 light chain clone 209-342

CDR1: QATQDIVKNLN    (SEQ ID NO: 44)
    CDR2: YATELAE    (SEQ ID NO: 45)
    CDR3: LQFYDFPLT    (SEQ ID NO: 46)

TA-B1-mur.A34 heavy chain clone 209-342

CDR1: DYATH    (SEQ ID NO: 47)
    CDR2: VISSYSGNT    (SEQ ID NO: 48)
    CDR3: YDYDVRYYAMDY    (SEQ ID NO: 49)

FIG. 24

```
AGCGGGGCGATGCCCAGCAGATAAGCCAGGCAAACCTCGGTGTGATCGAAGAAGCCAATTTG
AGACTCAGCCTAGTCCAGGCAAGCTACTGGCACCTGCTGCTCTCAACTAACCTCCACACAAT
GGTGTTCGCATTTTGGAAGGTCTTTCTGATCCTAAGCTGCCTTGCAGGTCAGGTTAGTGTGG
TGCAAGTGACCATCCCAGACGGTTTCGTGAACGTGACTGTTGGATCTAATGTCACTCTCATC
TGCATCTACACCACCACTGTGGCCTCCCGAGAACAGCTTTCCATCCAGTGGTCTTTCTTCCA
TAAGAAGGAGATGGAGCCAATTTCTATTTACTTTTCTCAAGGTGGACAAGCTGTAGCCATCG
GGCAATTTAAAGATCGAATTACAGGGTCCAACGATCCAGGTAATGCATCTATCACTATCTCG
CATATGCAGCCAGCAGACAGTGGAATTTACATCTGCGATGTTAACAACCCCCAGACTTTCT
CGGCCAAAACCAAGGCATCCTCAACGTCAGTGTGTTAGTGAAACCTTCTAAGCCCCTTTGTA
GCGTTCAAGGAAGACCAGAAACTGGCCACACTATTTCCCTTTCCTGTCTCTCTGCGCTTGGA
ACACCTTCCCCTGTGTACTACTGGCATAAACTTGAGGGAAGAGACATCGTGCCAGTGAAAGA
AAACTTCAACCCAACCACCGGGATTTTGGTCATTGGAAATCTGACAAATTTTGAACAAGGTT
ATTACCAGTGTACTGCCATCAACAGACTTGGCAATAGTTCCTGCGAAATCGATCTCACTTCT
TCACATCCAGAAGTTGGAATCATTGTTGGGGCCTTGATTGGTAGCCTGGTAGGTGCCGCCAT
CATCATCTCTGTTGTGTGCTTCGCAAGGAATAAGGCAAAAGCAAAGGCAAAAGAAAGAAATT
CTAAGACCATCGCGGAACTTGAGCCAATGACAAAGATAAACCAAGGGGAGAAAGCGAAGCA
ATGCCAAGAGAAGACGCTACCCAACTAGAAGTAACTCTACCATCTTCCATTCATGAGACTGG
CCCTGATACCATCCAAGAACCAGACTATGAGCCAAAGCCTACTCAGGAGCCTGCCCCAGAGC
CTGCCCCAGGATCAGAGCCTATGGCAGTGCCTGACCTTGACATCGAGCTGGAGCTGGAGCCA
GAAACGCAGTCGGAATTGGAGCCAGAGCCAGAGCCAGAGCCAGAGTCAGAGCCTGGGGTTGT
AGTTGAGCCCTTAAGTGAAGATGAAAAGGGAGTGGTTAAGGCATAGGCTGGTGGCCTAAGTA
CAGCATTAATCATTAAGGAACCCATTACTGCCATTTGGAATTCAAATAACCTAACCAACCTC
CACCTCCTCCTTCCATTTTGACCAACCTTCTTCTAACAAGGTGCTCATTCCTACTATGAATC
CAGAATAAACACGCCAAGATAACAGCTAAATCAGCAAGGGTTCCTGTATTACCAATATAGAA
TACTAACAATTTTACTAACACGTAAGCATAACAAATGACAGGGCAAGTGATTTCTAACTTAG
TTGAGTTTTGCAACAGTACCTGTGTTGTTATTTCAGAAAATATTATTTCTCTCTTTTTAACT
ACTCTTTTTTTTTATTTTGGACAGAGTCTTGCTCCGTCGCGCAGGCTGTGATCGTAGTGGTG
CGATCTCGGCTCACTGCGGCCTCCGCTCCCTGGGTTCGGGCGATTCTCCTGCCTGGGCCTCC
TGAGTGGCTGGGACTGCAGGCACGTGCCGCCACGCCCGGCTAATTTTTGTATTTTGGTAG
AGATGGGGTTTCACGTTGTTGGCCAGGATGGTCTCCATCTCCTGACCTCATGATCCGCCCAC
CTTGGCCTCCCAAAATGCTGGGATTACAGGCATGAGCCACTGCGCCCGGCCTCTTTTAGCT
ACTCTTATGTTCCACATGCACATATGACAAGGTGGCATTAATTAGATTCAATATTATTTCTA
GGAATAGTTCCTCATTCATTTTTATATTGACCACTAAGAAAATAATTCATCAGCATTATCTC
ATAGATTGGAAAATTTTCTCCAAATACAATAGAGGAGAATATGTAAAGGGTATACATTAATT
GGTACGTAGCATTTAAAATCAGGTCTTATAATTAATGCTTCATTCCTCATATTAGATTTCCC
AAGAAATCACCCTGGTATCCAATATCTGAGCATGGCAAATTTAAAAAATAACACAATTTCTT
GCCTGTGACCCTAGCACTTTGGGAGGCCGAGGCAGGTGGATCACCTGAGGTCAGGGGTTCGA
GACCAGCCTGGCCGACATGGCGAAGCCCCTTCTCTGCTAGGAATGCAGAAATTGGCTGGGCG
TGGTGGTGCATGCCTGTAGTCCCGGCTACTTGGGAGGCTGAGGCAGGAGAGTCGCTTGAACC
CAGGGGGTGGAGGTTGCAGTGAGCCGAGATTGTGCCACTGCACTCCAACCTGGGTGACGGAG
TGAGATTCCATCTGAAAAACAAAAACAAAAACAGAAAACAAACAAACAAAAACAAAAATC
CCCACAACTTTGTCAAATAATGTACAGGCAAACACTTTCAAATATAATTTCCTTCAGTGAAT
ACAAAATGTTGATATCATAGGTGATGTACAATTTAGTTTTGAATGAGTTATTATGTTATCAC
TGTGTCTGATGTTATCTACTTTGAAAGGCAGTCCAGAAAGTGTTCTAAGTGAACTCTTAAG
ATCTATTTTAGATAATTTCAACTAATTAAATAACCTGTTTTACTGCCTGTACATTCCACATT
AATAAAGCGATACCAATCTTATATGAATGCTAATATTACTAAAATGCACTGATATCACTTCT
TCTTCCACTGTTGAAAAGCTTTCTCATGATCATATTTCACCCACATCTCACCTTGAAGAAAC
TTACAGGTAGACTTACCTTTTCACTTGTGGAATTAATCATATTTAAATCTTACTTTAAGGCT
CAATAAATAATACTCATAATGTCCCAAAAAAAAAAAAAAA        (A34, SEQ ID
NO: 50)
```

FIG. 25

MVFAFWKVFLILSCLAGQVSVVQVTIPDGFVNVTVGSNVTLICIYTTTVASREQLSIQWSFF
HKKEMEPISIYFSQGGQAVAIGQFKDRITGSNDPGNASITISHMQPADSGIYICDVNNPPDF
LGQNQGILNVSVLVKPSKPLCSVQGRPETGHTISLSCLSALGTPSPVYYWHKLEGRDIVPVK
ENFNPTTGILVIGNLTNFEQGYYQCTAINRLGNSSCEIDLTSSHPEVGIIVGALIGSLVGAA
IIISVVCFARNKAKAKAKERNSKTIAELEPMTKINPRGESEAMPREDATQLEVTLPSSIHET
GPDTIQEPDYEPKPTQEPAPEPAPGSEPMAVPDLDIELELEPETQSELEPEPEPEPESEPGV
VVEPLSEDEKGVVKA     (A34, SEQ ID NO: 1)

FIG. 26

A34 AND A33-LIKE 3 DNA, PROTEINS, ANTIBODIES THERETO AND METHODS OF TREATMENT USING SAME

FIELD OF THE INVENTION

The invention relates to A34 and A33-like 3 polypeptides, and to the nucleotide sequences encoding these polypeptides, and nucleotide and polypeptide fragments thereof, as well as antisense sequences thereof. The invention also relates to immunoglobulin products that bind with specificity to A34 antigen and/or A33-like 3 antigen, and CDR and variable regions thereof. This invention is also directed to methods of inhibiting cancer in a patient with such immunoglobulin products, and to compositions comprising such immunoglobulin products, as well as to kits and methods of detecting cancers.

BACKGROUND OF THE INVENTION

Modern medicine has been indisputably enriched by the intersection of traditional treatments for disease with the inroads of molecular biology. In particular, immunology has provided new hope for the treatment of various diseases, particularly neoplastic diseases, by providing well-characterized and specific antibodies. Antibodies have become important as therapeutic agents because they may be targeted to a specific site for action. For example, cancer cells may possess a "marker" protein that may be a binding site or antigen for a particular antibody.

Historically, antibodies were generated in laboratory animals (usually mice or rabbits) by injecting laboratory animals with the antigen of interest over an extended period. (For general discussion of the structure and biosynthesis of immunoglobulins, see standard immunology textbooks, such as W. E. Paul, *Fundamental Immunology*, Raven Press, New York, N.Y. 1993, or Janeway et al., *Immunobiology The Immune System In Health and Disease*, Garland Publishing, New York, N.Y. 2001.) The foreign antigen resulted in an immune response; the resulting antibodies could then be purified from blood. However, this approach has limitations. In vivo use of antibodies from a different species may induce a potentially fatal response (for example, murine antibodies when injected into humans may produce a human anti-mouse antibody response—the "HAMA" response, see, for example, Schiff et al., *Cancer Research* 45: 879-885 (1985)). Additionally, non-human antibodies will be less efficacious in stimulating human complement or cell mediated toxicity.

Molecular biology again begins to provide an answer to these issues. Chimeric and recombinant antibodies are now being used to address these issues. Chimeric antibodies exploit the component nature of immunoglobulin products by combining portions of antibodies from different species. For example, the variable region from a mouse may be combined with the constant regions from a human. Recombinant DNA techniques are then used for cutting and splicing the various components to form functional immunoglobulin products. Another approach for expanding the utility of antibodies into immunoglobulin products is the technique known as "CDR grafting." In this method, only the complementarity determining region, "CDR," is inserted into a human antibody framework. Even this approach may be fine-tuned by substitution of critical murine antibody residues in the human variable regions. The binding of an antibody to its target antigen is mediated through the complementarity-determining regions (CDRs) of its heavy and light chains, with the role of CDR3 of the heavy chain being of particular importance (Xu and Davis, Immunity, 13:37-45, 2000). The use and production of such humanized antibodies continues to be explored, but these techniques are in common current usage. U.S. Pat. Nos. 5,225,539; 5,530,101; 5,585,089; and 5,859,205 describe examples of such techniques.

Yet another approach to avoid the potential problems of immunogenic reactions against non-human protein sequences is using fully human antibodies. Methods for preparing fully human antibodies are well known in the art. For example, fully human antibodies can be prepared by immunizing transgenic mice which express human immunoglobulins instead of mouse immunoglobulins. An antibody response in such a mouse directly generates fully human antibodies. Examples of such mice include the Xenomouse™ (Abgenix, Inc.) and the HuMAb-Mouse@ (Medarex, Inc.,), see also U.S. Pat. No. 6,207,418, U.S. Pat. No. 6,150,584, U.S. Pat. No. 6,111,166, U.S. Pat. No. 6,075,181, U.S. Pat. No. 5,922,545, U.S. Pat. No. No. 5,545,806 and U.S. Pat. No. 5,569,825. Antibodies can then be prepared by standard techniques, e.g., standard hybridoma techniques, or by phage display (see below). These antibodies will then contain only fully human amino acid sequences.

Monoclonal antibodies, including fully human antibodies, may also be generated and isolated from phage display libraries. The construction and screening of phage display libraries are well known in the art, see, e.g., Marks et al., *J. Mol. Biol.* 222(3): 581-597 (1991); Hoogenboom et al., *J. Mol. Biol.*, 227(2): 381-388 (1992); and U.S. Pat. Nos. 5,885,793, and 5,969,108.

The following references are illustrative of such fully human antibodies and phage display techniques: Marks et al., "By-passing immunization. Human antibodies from V-gene libraries displayed on phage," *J. Mol. Biol.* 222(3):581-597 (1991); Hoogenboom et al., "By-passing immunization. Human antibodies from synthetic repertoires of germline VH gene segments rearranged in vitro," *J. Mol. Biol.* 227(2):381-388 (1992).

Novel strategies for improving the efficacy of therapeutic monoclonal antibodies, such as augmenting their in vivo effector function, conjugating them directly to cytotoxic agents or radionuclides, and activating such conjugated agents with pre-targeted pro-drugs, as well as coupling monoclonal antibody therapy with traditional chemotherapy regimes, have been introduced. Large scale clinical trials employing these second generation monoclonal antibodies are currently underway and some have gained FDA approval for the treatment of cancer, most notably anti-c-erbB-2/Her2neu (Herceptin) for the treatment of breast cancer, anti-CD20 (Rituxan) for the treatment of non-Hodgkins lymphoma, and anti-CD52 (Campath) for the treatment B cell chronic lymphocytic leukemia.

The discovery of new, therapeutically relevant cell surface target molecules has not kept pace with the rapid advances in monoclonal antibody technology, and only a relatively small number of antigenic targets are being pursued in this regard. This is especially poignant given the momentous progress in gene discovery emanating from the analysis of the human genome, trascriptome, and proteome. In contrast, the identification of intracellular targets for active-specific cancer immunotherapy i.e., cancer vaccines, has flourished in the last decade. Thus, mining the human transcriptome for new cell surface antigens is highly warranted. In this regard, the instant invention resulted partially from searching the human expressed sequence tag (EST) database for novel transcripts encoding tissue-restricted cell surface proteins because these may represent new targets for monoclonal antibody based therapies.

The A33/JAM gene family includes at least seven previously known proteins (A33, CAR, HCTX, ELAM, JAM1, JAM2, and JAM3). These proteins are generally distinguished by two transmembrane domains (with a single signal sequence) and two Ig-like domains. One member, A33, is known to be associated with colon cancer. The isolation and characterization of the A33 molecule is described in U.S. Pat. No. 5,712,369. Humanized antibodies to A33 are described in U.S. Pat. Nos. 5,958,412; 6,307,026, and Rader et al., *J. Biol. Chem.* 275(18):13668-76 (2000); methods of using A33 antibodies are described in U.S. Pat. No. 6,346,249 B1 and U.S. Pat. No. 6,342,587. All these references are specifically incorporated herein by reference.

Human clinical trials have been conducted with mouse and humanized antibodies directed to A33. The biodistribution and imaging characteristics of $^{131}$I-mAb A33 were studied in colon carcinoma patients with hepatic metastases. The studies showed that mAb A33 localization was antigen-specific, cancer:liver ratios were 2.3- to 45 fold higher for specific antibody as compared to non-specific antibodies. See, for example, Welt et al., *J. Clin. Oncol.* 8:1894-1906 (1990). A subsequent radioimmunotherapy phase I/II study of $^{131}$I-mAb A33 demonstrated that $^{131}$I-mAb A33 had modest anticancer effects in heavily pre-treated patients who were no longer responding to chemotherapy. See, for example, Welt et al., *J. Clin. Oncol.* 12:1561-1571 (1994).

Other clinical trials and results for A33 mAbs have been described in, for example, Welt et al., "Quantitative analysis of antibody localization in human metastatic colon cancer: a phase I study of monoclonal antibody A33," *J. Clin. Oncol.* 8(11):1894-906 (1990); and Welt et al., "Phase I/II study of iodine 131-labeled monoclonal antibody A33 in patients with advanced colon cancer," *J. Clin. Oncol.* 12(8):1561-71 (1994).

However, A33 is a marker mainly limited to colon cancer. Two novel members of the A33/JAM family are herein described. One new protein/gene is termed "A34." Yet another novel member of this family is also described and is termed "A33-like 3."

U.S. Pat. No. 6,312,921, to Jacobs et al. for "Secreted Proteins and Polynucleotides Encoding Them," discloses protein and polynucleotides with some overlap with A34. However, these sequences are not identical to A34 or A33-like 3: and, in contrast to the disclosed methods of the instant invention, Jacobs' disclosed uses are non-specific, i.e., for unspecified biological activity, research uses, and nutritional uses.

DETAILED DESCRIPTION OF THE INVENTION

Definitions

Bispecific antibodies: Bispecific antibodies are monoclonal, preferably human or humanized, antibodies that have binding specificities for at least two different antigens. In the present case, one of the binding specificities is for A34 or A33 like 3, the other one is for any other antigen, and preferably for a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities [Milstein and Cuello, Nature, 305:537-539 (1983)]. It is also well known within the art of how to generate bispecific antibodies, or bispecific antibody fragments, by using recombinant DNA techniques [Kriangkum et al. Biomol Eng. 2001 September; 18(2):31-40].

Cancer: Any one of a number of diseases characterized by uncontrolled cell growth and/or proliferation. Examples are neoplasms, adenocarcinomas, carcinomas, tumors, leukemias, etc.

CDR: Complementarity determining regions, sections of an immunoglobulin molecule. There are typically three CDRs present in each heavy and light chain, respectively.

Epitope: A portion of a molecule (generally a protein, though it may be any moiety) that is specifically recognized by an immunoglobulin product.

Fragment: Various fragments of immunoglobulin or antibodies are known in the art, i.e., Fab, Fab$_2$, F(ab')$_2$, Fv, Fc, Fd, scFvs, etc. A Fab fragment is a multimeric protein consisting of the immunologically active portions of an immunoglobulin heavy chain variable region and an immunoglobulin light chain variable region, covalently coupled together and capable of specifically binding to an antigen. Fab fragments are generated via proteolytic cleavage (with, for example, papain) of an intact immunoglobulin molecule. A Fab$_2$ fragment comprises two joined Fab fragments. When these two fragments are joined by the immunoglobulin hinge region, a F(ab')$_2$ fragment results. An Fv fragment is a multimeric protein consisting of the immunologically active portions of an immunoglobulin heavy chain variable region and an immunoglobulin light chain variable region covalently coupled together and capable of specifically binding to an antigen. A fragment could also be a single chain polypeptide containing only one light chain variable region, or a fragment thereof that contains the three CDRs of the light chain variable region, without an associated heavy chain moiety or, a single chain polypeptides containing only one heavy chain variable region, or a fragment thereof containing the three CDRs of the heavy chain variable region, without an associated light chain moiety; and multi specific antibodies formed from antibody fragments, this has for example been described in U.S. Pat. No. 6,248,516. Fv fragments or single region (domain) fragments are typically generated by expression in host cell lines of the relevant identified regions. These and other immunoglobulin or antibody fragments are within the scope of the invention and are described in standard immunology textbooks such as Paul, *Fundamental Immunology* or Janeway et al. *Immunobiology* (cited above). Molecular biology now allows direct synthesis (via expression in cells or chemically) of these fragments, as well as synthesis of combinations thereof A fragment of an antibody or immunoglobulin can also have bispecific function as described above.

Immunoglobulin molecule (Igs): A class of protein molecules present in bodily fluids (e.g., plasma, colostrum, and tears) which have one or more immunoglobulin domains. Typically, a monomeric immunoglobulin molecule comprises four polypeptide chains. The four chains are two identical heavy chains and two identical light chains and are linked by disulfide bonds to form the Y-shaped monomeric antibody molecule.

Immunoglobulin superfamily molecule: A molecule that has a domain size and an amino acid sequence that is significantly similar to immunoglobulin or immunoglobulin domains. This similarity significance is determined via computer program (for example, Align, a program described by Dayhoff et al., *Meth. Enzymol.* 91: 524-545 (1983)). An Align computer program score of less than 3 indicates that the molecule is a member of an immunoglobulin superfamily. Examples include immunoglobulin heavy chains from IgM, IgD, IgG, IgA, or IgE, light chains kappa and lambda, major histocompatibility antigens, etc.

Multimeric protein: a protein containing more than one separate polypeptide or protein chain associated with one another to form a singular protein unit. The units may be the same or different, i.e., homodimers and heterodimers are both encompassed.

Polypeptide and peptide: A linear series of amino acids connected covalently by peptide bonds between the alpha amino and carboxy groups of adjacent amino acids.

Protein: A linear series of greater than about 50 amino acids where said amino acids are connected covalently by peptide bonds between the alpha amino and carboxyl groups of adjacent amino acids.

Therapeutically effective amount: The amount of a composition administered to a patient in need thereof in the course of treatment. The amount and concentration of the active ingredient(s) is within the skill of one of ordinary skill in the medical and biomedical arts, and takes into account such factors as the age, health, weight, height, overall physical condition, disease state, other medications received, etc., of the patient in need of treatment.

Treatment or treating: A method of inhibiting, reducing, alleviating, and/or ameliorating all or some of the effects of a disease in a patient. Treatment includes the prevention of occurrence of a disease in a patient who is currently not experiencing any symptoms, but who is or who may be at risk for the disease.

The instant invention comprises isolated A34 and A33-like 3 proteins and/or polypeptide molecules, and isolated polynucleotide molecules encoding these proteins and/or polypeptide molecules. It also encompasses the isolated immunoglobulin products that bind these proteins and/or any epitopes thereof, and various fragments thereof, including variable regions and/or CDRs.

The protein and/or immunoglobulin product according to the invention may be isolated from natural sources, or may be produced recombinantly in host cells. Included within the scope of the invention are the conservative substitutions known to one of ordinary skill in the art, i.e., substitutions resulting in substantially similar sequences. Conservative substitutions are those amino acid or nucleic acid substitutions which do not significantly change the properties of the molecule compared to the molecule before the substitution(s). Substantially similar nucleic acid fragments of the instant invention may also be characterized by the percent identity of the amino acid sequences that they encode to the amino acid sequences disclosed herein, as determined by algorithms commonly employed by those skilled in this art.

As used herein, the term "conservative substitution" denotes the replacement of an amino acid residue by another, biologically similar residue. As such, it should be understood that in the context of the present invention, a conservative substitution is recognized in the art as a substitution of one amino acid for another amino acid that has similar properties. Examples of conservative substitutions include the substitution of one hydrophobic residue such as isoleucine, valine, leucine, alanine, cysteine, glycine, phenylalanine, proline, tryptophan, tyrosine, norleucine or methionine for another, or the substitution of one polar residue for another, such as the substitution of arginine for lysine, glutamic acid for aspartic acid, or glutamine for asparagine, and the like. Neutral hydrophilic amino acids which can be substituted for one another include asparagine, glutamine, serine and threonine. The term "conservative substitution" also includes the use of a substituted amino acid in place of an unsubstituted parent amino acid.

Exemplary conservative substitutions are set out in the following Table A from WO 97/09433.

TABLE A

Conservative Substitutions I

| SIDE CHAIN CHARACTERISTIC | AMINO ACID |
|---|---|
| Aliphatic Non-polar | G A P I L V |
| Polar - uncharged | C S T M N Q |
| Polar - charged | D E K R |
| Aromatic | H F W Y |
| Other | N Q D E |

Alternatively, conservative amino acids can be grouped as described in Lehninger, (*Biochemistry,* 2nd Ed.; Worth Publishers, Inc. NY: N.Y. (1975), pp. 71-77) as set out in the following Table B.

TABLE B

Conservative Amino Acid Substitutions II

| SIDE CHAIN CHARACTERISTIC | AMINO ACID |
|---|---|
| Non-polar (hydrophobic) | |
| A. Aliphatic: | A L I V P |
| B. Aromatic: | F W |
| C. Sulfur-containing: | M |
| D. Borderline: | G |
| Uncharged-polar | |
| A. Hydroxyl: | S T Y |
| B. Amides: | N Q |
| C. Sulfhydryl: | C |
| D. Borderline: | G |
| Positively Charged (Basic): | K R H |
| Negatively Charged (Acidic): | D E |

Exemplary conservative substitutions are set out in the following Table C.

TABLE C

Conservative Substitutions III

| Original Residue | Exemplary Substitution |
|---|---|
| Ala (A) | Val, Leu, Ile |
| Arg (R) | Lys, Gln, Asn |
| Asn (N) | Gln, His, Lys, Arg |
| Asp (D) | Glu |
| Cys (C) | Ser |
| Gln (Q) | Asn |
| Glu (E) | Asp |
| His (H) | Asn, Gln, Lys, Arg |
| Ile (I) | Leu, Val, Met, Ala, Phe |
| Leu (L) | Ile, Val, Met, Ala, Phe |
| Lys (K) | Arg, Gln, Asn |
| Met (M) | Leu, Phe, Ile |
| Phe (F) | Leu, Val, Ile, Ala |
| Pro (P) | Gly |
| Ser (S) | Thr |
| Thr (T) | Ser |
| Trp (W) | Tyr, Phe |
| Tyr (Y) | Trp, Phe, Thr, Ser |
| Val (V) | Ile, Leu, Met, Phe, Ala |

If desired, the peptides of the invention can be modified, for instance, by glycosylation, amidation, carboxylation, or phosphorylation, or by the creation of acid addition salts, amides, esters, in particular C-terminal esters, and N-acyl derivatives of the peptides of the invention. The peptides also can be modified to create peptide derivatives by forming covalent or noncovalent complexes with other moieties. Covalently-bound complexes can be prepared by lining the chemical moieties to functional groups on the side chains of amino acids comprising the peptides, or at the N- or C-terminus.

In particular, it is anticipated that the aforementioned peptides can be conjugated to a reporter group, including, but not limited to a radiolabel, a fluorescent label, an enzyme (e.g., that catalyzes a colorimetric or fluorometric reaction), a substrate, a solid matrix, or a carrier (e.g., biotin or avidin).

Suitable nucleic acid fragments (isolated polynucleotides of the present invention) encode polypeptides that are at least about 70% identical, preferably at least about 80% identical, to the amino acid sequences reported herein. Preferred nucleic acid fragments encode amino acid sequences that are about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above identities but typically encode a polypeptide having at least 50 amino acids, preferably at least 100 amino acids, more preferably at least 150 amino acids, still more preferably at least 200 amino acids, and most preferably at least 250 amino acids. Also encompassed in the invention are antisense sequences of the isolated polynucleotides of the present invention.

Sequence alignments and percent identity calculations may be performed, for example, using the Megalign program of the LASERGENE bioinformatics computing suite (DNASTAR Inc., Madison, Wis.). Multiple alignment of the sequences may be performed using the Clustal method of alignment (Higgins and Sharp (1989) CABIOS. 5:151-153) with the default parameters (GAP PENALTY=10, GAP LENGTH PENALTY=10). Default parameters for pairwise alignments using the Clustal method may be KTUPLE 1, GAP PENALTY=3, WINDOW=5 and DIAGONALS SAVED=5, for example.

For the multiple sequence alignments shown, the Clustal (found at http://clustalw.genome.ad.jp/) default settings were utilized which rely on a GAP OPEN PENALTY=10 and a GAP EXTENSION PENALTY=0.05. For the pairwise alignments shown, the default settings for BLAST (found at http://www.ncbi.nlm.nih.gov/blast/bl2seq/bl2.html) were used, which rely on a GAP OPEN PENALTY=11 and a GAP EXTENSION PENALTY=1.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually, by one skilled in the art, or by using computer-based sequence comparison and identification tools that employ algorithms such as BLAST (Basic Local Alignment Search Tool; Altschul et al. *J. Mol. Biol.* 215:403-410 (1993); see also www.ncbi.nlm.nih.gov/BLAST/).

In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers.

Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise A34 and A33-like 3. The skilled artisan, having the benefit of the sequences as reported herein, may now use all or a substantial portion of the disclosed sequences for purposes known to those skilled in this art. Accordingly, the instant invention comprises the complete sequences as reported in the accompanying Figures and Sequence Listing, as well as substantial portions of those sequences as defined above, and antisense sequences thereof.

"Codon degeneracy" refers to divergence in the genetic code permitting variation of the nucleotide sequence without affecting the amino acid sequence of an encoded polypeptide. Accordingly, the instant invention includes any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

The immunoglobulin molecule may be an antibody, an Fv fragment, an $F_c$ fragment, an $F_d$ fragment, a Fab fragment, a Fab' fragment, a F(ab)$_2$ fragment, F(ab')$_2$ fragment, an scFvs fragment, a single chain antibody, a multimeric antibody, or any combination thereof. The immunoglobulin molecule may be joined to a reporter or chemotherapeutic molecule, or it may be joined to an additional fragment, and it may be a monomer or a multimeric product. The immunoglobulin molecule may also be made recombinantly, to include all or part of the variable regions and/or CDRs.

The inventive protein(s)/antibody(ies) make it possible to detect A34 and/or A33-like 3 polypeptide or polynucleotide molecules, in order to provide a patient with an accurate diagnosis of the presence of cancer that expresses any of these proteins. Detection methods and kits according to the invention may detect A34 and A33-like 3 molecules in any way known in the art. For example, the expression of A34 and A33-like 3 may be detected directly, via mRNA or antisense technology, e.g., by using PCR based techniques, or agents which bind the expressed protein may be detected, e.g., directly with an antibody or polypeptide fragment which binds said A34 and A33-like 3 molecule to form a complex. The antibody or polypeptide fragment which is capable of forming a complex may be linked with a label in order to facilitate detection of the complexes. Such labels are well known in the art, and include, for example, radioactive labels and fluorescent labels.

The bound complexes comprise immunoglobulin molecules with an affinity for A34 protein. This affinity may be greater than about 50 nM, or preferably greater than about 5 nM, as measured, for example, by surface plasmon resonance (Biacore™) or other biosensor system.

The present invention encompasses methods of diagnosing cancer characterized by the presence of A34 antigen in cancer cells, comprising: obtaining a sample of cells of interest;

contacting said sample with an agent, which specifically binds A34 antigen, such that A34/agent complexes may be formed; and detecting the presence or absence of said complexes, wherein the presence of said complexes indicates a positive cancer diagnosis.

In another embodiment, the present invention encompasses methods for determining regression, progression, or onset of a cancerous condition comprising monitoring a sample from a patient with said cancerous condition for the presence, absence, or change in expression level of A34 antigen comprising: obtaining a sample of interest; contacting said sample with at least one agent, which specifically binds A34 antigen, such that A34/agent complexes may be formed; and detecting the presence, absence or change in of said complexes, wherein the presence, absence, or change in expression level of said complexes indicates progression, regression or onset of cancer diagnosis.

In a further embodiment, the present invention encompasses methods for determining if cancer cells which express A34 are present in a sample, comprising: contacting a sample of interest with at least one oligonucleotide molecule which specifically hybridizes to a nucleic acid molecule which encodes A34, wherein hybridization of said at least one oligonucleotide molecule to a nucleic acid molecule is indicative of cancer cells which express A34 in said sample; and detecting the presence or absence of such hybridization, wherein the presence of said hybridization indicates the presence of cancer cells which express A34.

A kit according to the invention generally comprises an appropriate agent which forms a complex with at least one of the A34 and A33-like 3 molecules (either polynucleotide or polypeptide molecules) and instructions for the method of forming and detecting complexes in a sample of interest.

In general, the patient is a mammal; preferably, the patient is a human.

A further advantage of the immunoglobulin products according to the instant invention is in methods of treatment of cancers or neoplasms that express A34 and/or A33-like 3 protein. In addition to detecting these cancers, the immunoglobulins of the instant invention may be used to treat or to reduce the effects of said cancers and neoplasms by administration of the inventive immunoglobulin products, either alone, with a pharmaceutically acceptable carrier, or in combination with another anti-cancer agent. When the inventive immunoglobulin products are administered in combination with an additional anti-cancer agent, the complex is specifically targeted to the cancer cells, thus maximizing the therapeutic potential of the anti-cancer agent while minimizing damage to healthy tissues.

BRIEF DESCRIPTION OF THE DRAWINGS

The invention will be described in further detail with reference to illustrative embodiments shown in the accompanying drawings.

FIG. 3 shows the full length A34 amino acid sequence (SEQ ID NO: 1) and the amino acid sequence comparison of A34 with A33 (SEQ ID NO: 2).

FIG. 4 shows an initially obtained polynucleotide sequence (SEQ ID NO: 3) and amino acid sequence (SEQ ID NO: 4) of A34.

FIG. 5 shows an additional A34 clone polynucleotide (SEQ ID NO: 5) and amino acid sequence (SEQ ID NO: 6).

FIG. 6 shows the polynucleotide sequence (SEQ ID NO: 7) and amino acid sequence (SEQ ID NO: 8) of A33-like 3.

FIG. 7 shows a comparison between the amino acid sequences of A33-like 3 (SEQ ID NO: 9) and A33 (SEQ ID NO: 10).

FIGS. 12, 13, and 14 show an immunohistochemical analyses of A34 expression in normal stomach mucosa/fundic glands.

FIG. 21 shows the polynucleotide and amino acid sequences of an murine A34 variable region light chain clone and heavy chain clone designated 209-970. CDRs are indicated with shaded boxes and underlining.

FIG. 22 shows the polynucleotide and amino acid sequences of an murine A34 variable region light chain clone and heavy chain clone designated 209-564. CDRs are indicated with shaded boxes and underlining.

FIG. 23 shows the polynucleotide and amino acid sequences of an murine A34 variable region light chain clone and heavy chain clone designated 209-342.

FIG. 24 shows the amino acid sequences of the CDR regions for the three A34 antibody clones. (SEQ ID NOS: 32-49).

FIG. 25 shows the full length A34 nucleotide sequence, SEQ ID NO: 50.

FIG. 26 shows the full length A34 amino acid sequence, SEQ ID NO 1.

SUMMARY OF THE INVENTION

Figure 1:
FIG. 1 shows the end point RT-PCR expression of A34 mRNA in 24 normal tissues.

The invention relates to novel proteins from the same protein family as the A33 protein and to immunoglobulin products which recognize and bind to these novel proteins. Two additional members of the A33 protein family have been identified and are described herein, i.e., A34 and A33-like 3 protein. All three are members of the A33/JAM family, as shown by their amino acid sequences and expression profiles. Antibodies to A34 are of particular interest in treating esophaegeal, ovarian, and stomach cancers.

EXAMPLE 1

General Materials and Methods for Reverse Transcription and PCR

Tumor tissues were obtained from Memorial Sloan-Kettering Cancer Center, Weill Medical College of Cornell University and Aichi Cancer Center Research Center, Nagoya Japan. Normal tissue RNA preparations were purchased from Clontech Laboratories Inc. (Palo Alto, Calif.) and Ambion Inc. (Austin, Tex.). Total RNA from tumor tissues was prepared by the guanidinium thiocyanate method.

Normalized cDNA preparations derived from various normal tissues were purchased from Clontech laboratories Inc. (Palo Alto, Calif.). Additional cDNA preparations (tumor and normal tissues) were prepared using the Superscript First strand synthesis kit from Invitrogen Life Technologies (Carlsbad, Calif.) as per manufacturer's instructions using 5 micrograms of total RNA in 40 ml reaction. Normal tissue cDNA was also purchased from Origene Technologies Inc. (Rockville, Md.). This is the source of cDNA panel of 24 tissues used in the end point RT-PCR data shown in FIG. 1.

The concentration of A33, A34 and A33-like 3 mRNA transcripts in normal tissues was measured by real-time RT-PCR using 16 different normal tissue cDNA preparations (ovary, leukocyte, prostate, spleen, testis, thymus, brain, heart, kidney, liver, lung, placenta, skeletal muscle, pancreas, small intestine and colon) that had been normalized for 6 housekeeping genes (Clontech). Gene-specific TaqMan probes and PCR primers were designed using Primer Express software (Applied Biosystems, Foster City, Calif.), and their sequences are provided below.

Multiplex PCR reactions were prepared using 2.5 μl of cDNA diluted in TaqMan PCR Master Mix supplemented with 1.25 μl of Vic labeled human beta glucuronidase (GUS) endogenous control probe/primer mix (Applied Biosystems proprietary dye), 200 nM 6-carboxy-fluorescein labeled gene-specific TaqMan probe, and a 900 nM concentration of gene specific forward and reverse primers (300-900 nM). Triplicate PCR reactions were prepared for each cDNA sample. PCR consisted of 40 cycles of 95° C. denaturation (15 seconds) and 60° C. annealing/extension (60 seconds).

Thermal cycling and fluorescent monitoring were performed using an ABI 7700 sequence analyzer (Applied Biosystems). The point at which the PCR product is first detected above a fixed threshold, termed cycle threshold (Ct), was determined for each sample. The abundance of gene-specific transcripts in normal tissues was determined by comparison with a standard curve generated from the Ct values of known concentrations of plasmid DNA template encoding, for example, A33, A34 and/or A33-like 3.

The quantity of the specific transcripts of interest (i.e., A34, A33-like 3, etc.) present in various cancer specimens and additional normal tissues (breast, stomach, esophagus, cervix, adrenal) were calculated relative to a similarly prepared normal testis cDNA specimen. In these experiments, the resultant Ct values were first normalized by subtracting the Ct value obtained from the GUS endogenous control (DCt=Ct FAM–Ct VIC).

The concentration of the mRNA of interest (i.e., A34, A33-like 3, etc.) in various cancer specimens and additional normal tissues (experimental samples) was calculated relative to normal testis by subtracting the normalized Ct values obtained with normal tissue (for A34, subtracting the normalized Ct values obtained with normal testis) from those obtained with experimental samples (DDCt=DCt of experimental samples–DCt of normal tissue), and the relative concentration was determined (Relative Concentration=2-DDCt, formula derived by Applied Biosystems and published in ABI PRISM 7700 Sequence Detection System User Bulletin #2, Dec. 11, 1997).

Relative concentrations in the experimental samples were then plotted in terms of fg cDNA starting material, using the normalized testis cDNA preparation (Clontech) as a calibrator. For example, A34 mRNA was expressed in gastric cancer specimen #5 at a level that was 0.387 times the level detected in testis, and the expression level of A34 in a normalized, normal testis specimen was equivalent to 3.38 fg of cDNA starting material. Using the expression level in normal testis as a calibrator, gastric cancer specimen #5 was expressed at a level equivalent to 1.31 fg of cDNA starting material (0.387× 3.38).

EXAMPLE 2

The A34 Gene and its Murine Orthologue

Analysis of the human genome database mapped the A34 gene to chromosome Xq22.1-22.3, and revealed no sequences of high similarity, suggesting that A34 is a single copy gene with no additional family members. The A34 gene is approximately 34 Kb in length, equivalent to bp 117203-151283 of the chromosome X genomic contiguous sequence, NT 011765. The A34 gene spans 7 exons, whereby exon 1 encodes the 5' untranslated region and a large portion of the signal sequence, exons 2 and 3 encode the variable (V) immunoglobulin (Ig)-like domain, exons 4 and 5 encode the constant type 2 ($C_2$) Ig-like domain, exon 6 encodes the transmembrane domain and a portion of the cytoplasmic domain, and exon 7 encodes the remainder of the cytoplasmic domain and the 3' untranslated region. This intron/exon structure is quite similar to that of the A33 gene.

A putative murine ortholog of A34 was identified on the basis of nucleotide similarities, tissue distribution of homologous ESTs, protein similarities, chromosomal localization, and gene structure. Comparison of the human A34 nucleotide sequence with the mouse EST database showed more than 83% nucleotide identity with EST sequences belonging to murine Unigene cluster Mm.66893. There are currently 31 sequences in this Unigene cluster, including 23 ESTs derived from normal testis, 6 ESTs from derived normal stomach and 2 ESTs from derived normal cecum. This tissue distribution is quite similar to the tissue distribution of human A34 EST sequences.

The full length murine EST clone, RIKEN cDNA 4930405J24 (Genbank Acc. No. NM_030181), is the reference cDNA sequence for this mouse gene. This transcript consists of 2182 nucleotides and encodes a protein of 407 amino acids, which is 73% identical (330 amino acid overlap) to human A34 and maintains the human A34 domain structure i.e. extracellular V-type and $C_2$ type Ig-like domains, transmembrane domain, and intracellular domain. The extracellular cysteine residues are conserved among the human and murine proteins, and like human A34, there are 6 potential N-glycosylation sites. The intracellular domain is the least conserved portion of the protein, though, like human A34, EP repeats are also found in carboxyl terminal residues of the intracellular domain of the putative murine protein. The murine A34 gene is approximately 31 Kb in length, equivalent to bp 5534868-5566206 of murine chromosome X genomic contiguous sequence, NT 039716, and spans 7 exons, encoding the same protein domains as the 7 exons of human A34 described above.

EXAMPLE 3

A34 mRNA expression in normal tissues was investigated in an initial experiment by RT-PCR according to the experimental procedure of Example 1 using the following primers:

```
A33L2F, bp 222
ACTGTTGGATCTAATGTCAC      (SEQ ID NO: 11)

A33L2R, bp 543
AAGGTTTCACTAACACACTG      (SEQ ID NO: 12)
```

The results showed that A34 was expressed in testis and stomach, but no significant expression was found in any of the other 22 normal tissues tested, see FIG. 1 (Origene cDNA panel of 24 normal tissues was used).

Subsequently, a A34 clone of 1045 bp (SEQ ID NO: 5) encoding 348 amino acids (SEQ ID NO: 6) was obtained. Although the protein obtained was partial, its sequence includes all but the amino-terminal-most 48 amino acids (which are part of the extracellular domain) and the carboxyl-terminal most 48 amino acids (which are part of the intracellular domain).

Further expression analysis on normal and tumor tissues using real time RT-PCR utilized the following primers:

```
L2f =
GAAGGAGATGGAGCCAATTTCTATT    (SEQ ID NO: 13)

L2r =
CCTGTAATTCGATCTTTAAATTGCC    (SEQ ID NO: 14)
``` with the following Taqman-probe:

```
6FAM- CTTTTCTCAAGGTGGACAAGCTGTAGCC (SEQ ID NO: 15)
ATC -TAMARA
```

The experimental procedure was performed similarly to that described in Example 1. In this instance, TAMARA was used as the quencher dye, with VIC or FAM as reporter dyes, though any quencher/reporter system known to one of ordinary skill may also be used.

This experiment showed significant A34 expression in testis and stomach, while 19 other specimens showed low to trace levels of A34 expression. These results are illustrated graphically in FIG. 2. A34 was also expressed at high levels in 2 of 6 gastric cancers, 9 of 16 esophageal cancers, and 4 of 17 ovarian cancers as shown in Table 1. This differential expression can be exploited by targeting with immunoglobulin molecules, such as antibodies, and/or conjugated immunoglobulin molecules, such as antibody-drug conjugates or antibody-radionuclide conjugates for therapeutic or diagnostic purposes. The differential expression can also be exploited for diagnostic purposes by using techniques such as PCR in measuring the A34 nucleic acid expression.

TABLE 1

Tumor Tissues:

| | |
|---|---|
| Gastric Cancer | 2/6 (33%) |
| Esophageal Cancer | 9/16 (56%) |
| Ovarian Cancer | 4/17 (23%) |
| Lung Cancer | 0/9 |
| Colon Cancer | 0/5 |
| Melanoma | 0/3 |

Figure 2:
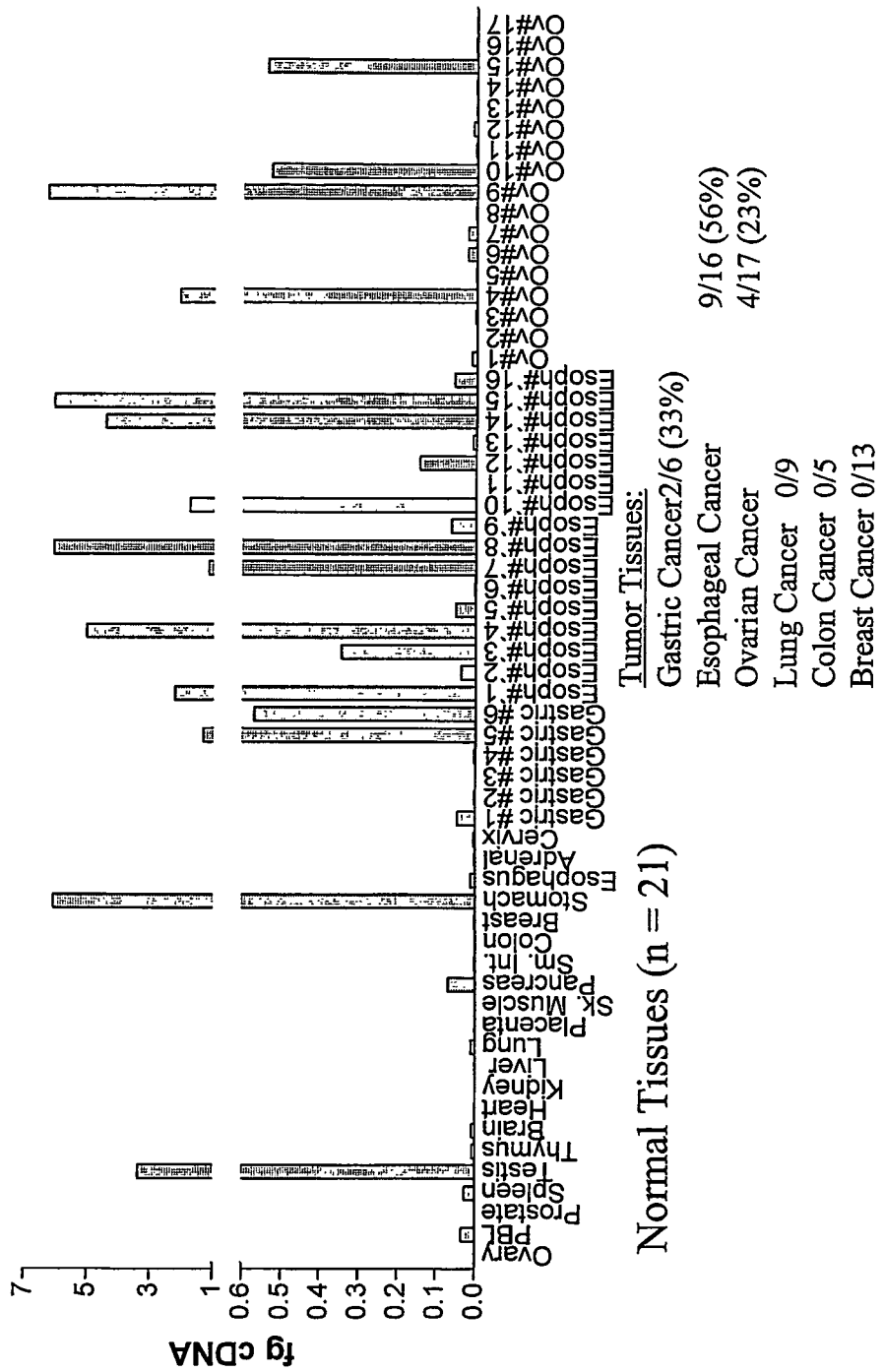
FIG. 2 shows an analysis of A34 expression in normal and malignant tissues using real-time PCR.

Expression Profile of A34 mRNA Transcripts:

In order to investigate the expression pattern of A34 mRNA, real-time quantitative RT-PCR was performed using a normalized cDNA panel derived from 21 normal adult tissues, and various malignant tissues. As shown in FIG. 2, A34 mRNA was expressed at high levels in testis (3.4 fg) and stomach (7.4 fg), and at a low level in normal pancreas (0.07 fg). Only trace levels (0.03-0.001 fg) of mRNA were detected in 13 other normal tissues (spleen, PBL, thymus, brain, heart, liver, lung, placenta, small intestine, breast, esophagus, adrenal gland, cervix). No A34 mRNA was detected in the remaining 5 normal tissues (ovary, prostate, colon, kidney, and skeletal muscle). A34 mRNA expression was also examined in a normalized cDNA panel derived from various malignant tissues. As shown in FIG. 2, high level A34 mRNA expression (0.5 fg or above) was detected in 2/6 gastric cancer specimens, 8/16 esophageal cancer specimens, and 4/17 ovarian cancer specimens. A34 mRNA was not detected in lung cancer (0/9 specimens), colon cancer (0/5 specimens), or breast cancer (0/13 specimens). Thus in the cDNA panels examined, A34 mRNA expression was largely restricted to normal testis and stomach, as well as ovarian, gastric and esophageal cancers.

EXAMPLE 4

Identification of the A34 mRNA Transcript:

In order to identify paralogues of the A33 colon cancer antigen that could serve as novel targets for monoclonal antibody-based therapy of human cancer, the amino acid sequence glycoprotein A33 was compared with a translated, non-redundant nucleotide database:

A novel transcript termed A34 was identified, which upon hypothetical translation showed 31% amino acid identity with A33, including limited conservation of a putative signal sequence, immunoglobulin (1g)-like domains and a transmembrane domain, suggesting it encoded a cell surface protein. The A34 transcript was represented by Unigene cluster Hs.177164, which contains a full length testisderived cDNA clone, MGC:44287 (Genbank Acc. No. BC043216), as well as 15 other homologous expressed sequence tags (ESTs), derived mainly from normal testis (7 ESTs), and also from normal stomach (2 ESTs), normal aorta (1 EST), uterine cancer (2 ESTs), pancreatic cancer (I EST), and pooled tissues (2 ESTs). The limited distribution of homologous ESTs suggested that the A34 transcript was differentially expressed.

Analysis of the human genome database mapped the gene encoding A34 to chromosome Xq22.1. Thus, A34 shares certain characteristics, such as a prevalence of testis-derived ESTs and mapping to chromosome X, with members of the cancerltestis (CT) antigen family, a group of immunogenic proteins whose expression is restricted to gametogenic tissue and cancer, and are considered target molecules for therapeutic cancer vaccines. Therefore, on the basis of its similarity with the A33 colon cancer antigen, the limited tissue distribution of homologous ESTs, and its similarity with CT antigens, the A34 gene product became the focus of our search for novel cell surface molecules expressed in cancer.

The full length A34 transcript, represented by testis-derived cDNA clone, MGC:44287, consists of 3017 nucleotides (see FIG. 25), a length in agreement with the single hybridization signal of 3.1 Kb detected on Northern blots of testis mRNA hybridized with a $^{32}P$ labeled A34 cDNA probe. The A34 transcript, as represented by MGC:44287, contains 122 bp of 5' untranslated sequence and 1731 bp of 3' untranslated sequence. The A34 nucleotide sequence was verified by sequencing an additional full length A34 EST clone, IMAGE: 5266771, as well as four independent cDNA clones, encompassing the entire protein coding region of A34, generated by RT-PCR of human testis RNA. Both strategies yielded cDNA sequences identical to MGC:44287 in the protein coding regions, although IMAGE:5266771 contained a 712 bp deletion in the 3' untranslated region corresponding to nucleotides 1702-2413 of MGC:44287.

A34 Protein:

An initial experiment showed that A34 (SEQ ID NO: 3) encoded a protein of 387 amino acids (SEQ ID NO: 4). Subsequent cloning of the A34 transcript as detailed above revealed the complete protein and DNA (see SEQ ID NOs: 1 and 50).

The predicted ATG start site, present at bp 123 of clone MGC:44287, conformed to the Kozak consensus sequence for initiation of protein translation, and is followed by the longest possible open reading frame of 1161 bp. The A34 protein consisted of 387 amino acids (Mr 41,816), comprising three structural domains: an extracellular domain of 233 amino acids, a transmembrane domain of 23 amino acids, and an intracellular domain of 131 amino acids (FIG. 3). Following the initial methionine residue, the N-terminal most 21 amino acids formed a putative hydrophobic signal sequence with a possible cleavage site between residues 21 and 22. Amino acid residues 33-123 encompassed an N-terminal, V-type Ig-like domain containing two cysteine residues ($C^{43}$, $C^{116}$), which are predicted to form disulfide bonds. A segment of 31 amino acids separated the V-type Ig-like domain from a second Ig-like domain of the $C_2$ type present at residues 154-218, which contains two cysteine residues ($C^{161}$, $C^{211}$).

The extracellular domain of A34 has 6 potential N-linked glycosylation sites. Given that the average size of an oligosaccharide chain is approximately of 2.5 kDa, the carbohydrate portion of A34 could potentially contribute approximately 15 kDa of mass, and thus the predicted size of native A34 protein (less the signal peptide of 2.3 kDa) is 54.4 kDa. Hydrophobicity plots and transmembrane domain prediction software located a transmembrane domain at residues 234-256, which was followed by a C-terminal intracellular domain encompassing residues 257-387. The A34 intracellular domain contained 7 sites of potential serine/threonine phosphorylation (casein kinase II phosphorylation sites), and a GSK3 phosphorylation site. Two TRAF2-binding consensus motifs are present at amino acids 314-317 and 324-327. Furthermore, a unique pattern of glutamic acid/proline repeats (EP) is found in the carboxyl terminus of A34. This pattern is found in only two other known human proteins, hematopoietic lineage cell specific protein (HS1) and src substrate protein p85fcortactin.

The domain organization and amino acid sequence of A34 placed it in the junctional adhesion molecule (JAM) family. The JAM family includes molecules such as GPA33, Coxsackie and adenovirus receptor (CXADR), cortical thymocyte receptor-like protein (CTXL), JAM1/F11 receptor, JAM2, and JAM3/Mac-1 receptor, which are believed to mediate cell-cell adhesion, and localize to tight junctions of epithelial and endothelial cells. Members are characterized by two extracellular Ig-like domains (V and $C_2$ type), conserved cysteine residues in the extracellular domain, and a single transmembrane domain. The A34 domain structure has a similar organization. An alignment of A34 and A33 is provided in FIG. 3. The A34 amino acid sequence is 35%, 32%, 28%, 26%, 25%, and 27% identical to CTXL (244 amino acid overlap), A33 (262 amino acid overlap), JAM2 (232 amino acid overlap), CXADR (259 amino acid overlap), JAM1 (270 amino acid overlap), and JAM3 (113 amino acid overlap), respectively, with conservation of at least 4/6 cysteine residues in the extracellular domain.

A34 has a predicted molecular weight of 41.8 kDa and which is 32% identical to A33 and 49% similar to A33, see Table 2 for comparisons with other A33/JAM family proteins (similarity percentage obtained according to BLAST).

A34 was located in unigene cluster Hs.177164 on chromosome Xq22.1-22.3. The A34 amino acid sequence contains a hydrophilic signal (leader sequence) residues 2-21, two Ig-like domains (residues 33-123, and 154-218) and a single transmembrane domain (residues 234-256).

TABLE 2

| Family Member Compared with A34 | Identity | Similarity | Location |
| --- | --- | --- | --- |
| A33 | 32% | 49% | 262 aa, A34 aa 1-256, A33 aa 1-257 |
| CXADR | 26% | 43% | 259 aa, A34 aa 9-258, CAR aa 7-261 |
| CTXL | 35% | 55% | 244 aa, A34 aa 9-256, hCTX aa 16-261 |
| ESAM | 29% | 45% | 261 aa, A34 aa 8-254, ESAM aa 16-268 |
| JAM1 | 25% | 40% | 270 aa, A34 aa 11-257, JAM1 aa 16-260 |
| JAM2 | 28% | 44% | 232 aa, A34 aa 48-258, JAM2 aa 56-262 |
| JAM3 | 27% | 42% | 113 aa, A34 aa 158-257, JAM3 aa 3-112 |

The intracellular domains of the JAM family, including A34, are poorly conserved. For example, the intracellular domain of A34 consists of 131 amino acids, while the intracellular domain of A33 consists of 60 amino acids, and there is no significant similarity in composition between the two intracellular domains (FIG. 3).

A34 Antibodies:

In order to investigate the A34 protein in vivo and in vitro, a murine monoclonal antibodies were generated to the extracellular domain of A34 (amino acids 35-231). A recombinant HIS-tagged recombinant polypeptide, comprising 209 amino acids (23 kDa) derived from the extracellular domain of A34, was produced. Mice were immunized with this recombinant polypeptide and three IgG1 monoclonal antibodies were isolated (identified as 342, 564, and 970) and purified in milligram quantities.

Total RNA was extracted by standard RNA isolation techniques (Chomczynski & Sacchi, *Anal. Biochem.* 1987 162: 156-159) from the hybridomas corresponding to the three IgG1 monoclonal antibodies. First strand cDNA was prepared using the First strand cDNA synthesis kit (Pharmacia Biotech) and priming with d(T)18 for both the heavy and light chains (Renner et al., *Biotechniques* 1998 24(5): 720-2). This cDNA was subjected to PCR using combinations of standard primers for murine heavy and light chains. The PCR products for heavy and light variable regions were cloned using the TA Cloning System (Invitrogen Corporation, Carlsbad, Calif.) and subsequently sequenced using standard techniques. The sequences for variable and CDR regions of the three murine antibodies are shown in FIGS. 21-24.

Figure 8:
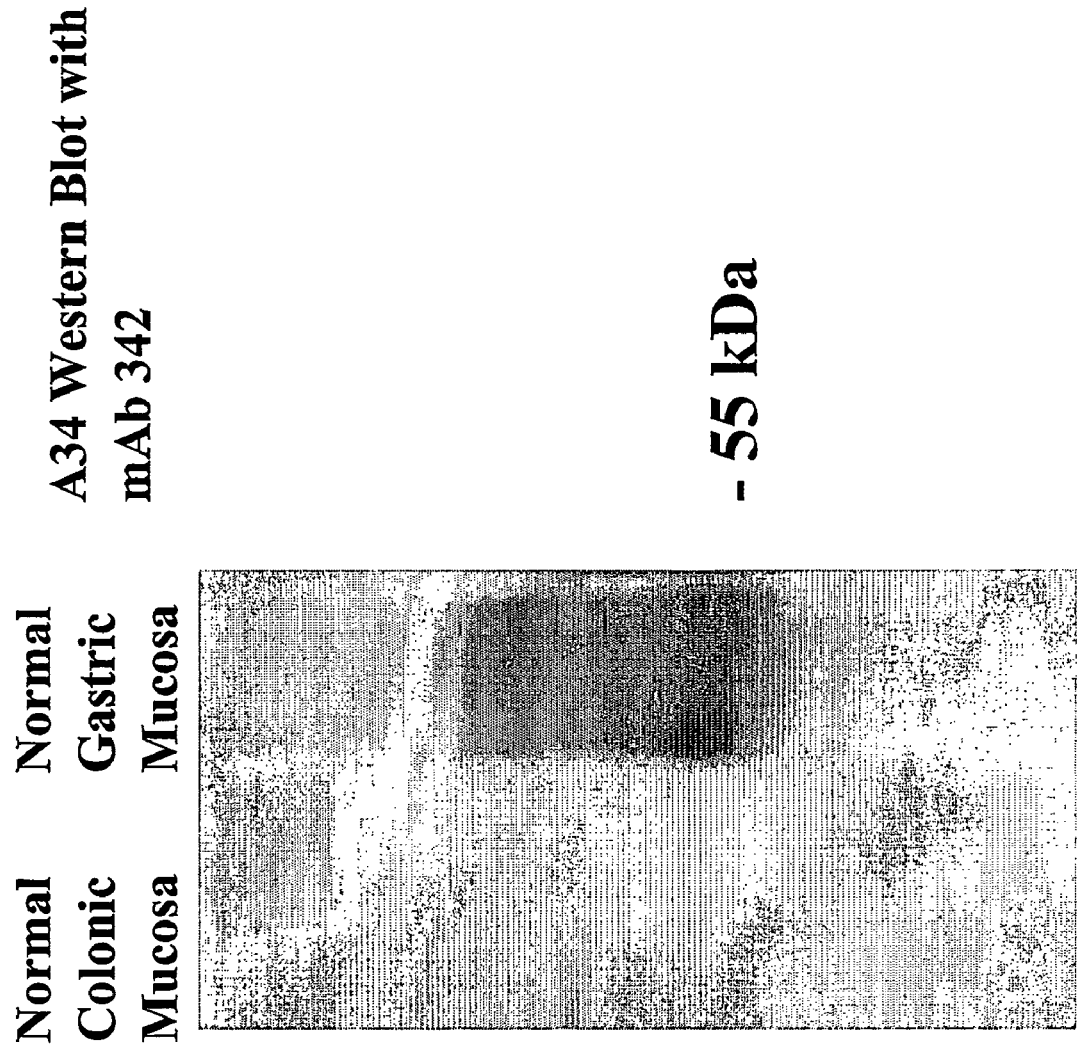
FIG. 8 shows a Western blot with mAb 342 of normal colonic mucosa and normal gastric mucosa.

As shown in FIG. 8, monoclonal antibody 342 recognized a 51 kDa protein in Western blots prepared from human gastric mucosa. This protein was not present in similar lysates prepared from human colonic mucosa. The 51 kDa size of the A34 protein detected by Western blotting is consistent with predicted size of 54.4 kDA determined by hypothetical translation of the A34 cDNA and predicted carbohydrate contributions.

Preliminary immunohistochemical analyses of A34 were done on formalin-fixed paraffin embedded tissues as follows.

Initially, four antibody clones, which were positive by ELISA, were analyzed by immunohistochemistry (IHC). Reactivity was first tested on frozen tissues with known A34 mRNA expression and different dilutions of newly generated hybridoma supernatant were tested. The tissues were snap-frozen specimens, embedded in OCT (optimal cutting temperature) compound. Five mm cuts were fixed in cold acetone for 10 minutes and blocking of endogenous peroxidase activity was done with 3% $H_2O_2$. Primary antibody incubation was done overnight at 5° C. The primary antibodies were detected by a biotinylated horse-anti-mouse (Vector, Labs, Burlingame, Calif.) secondary antibody, followed by an avidin-biotin-complex (ABC-Elite, Vector Labs) system. 3,3'-diaminobenzidine (Liquid DAB, BioGenex, San Ramon, Calif.) served as a chromogen, and hematoxylin was used as a counterstain.

Reactive clones were then purified and an optimal working concentration was established by IHC titering on tissue specimens. Three of the four (342, 970, 564) hybridoma clones showed reactivity in frozen stomach and testis, and dilutions were 1:20 of all three clones. These clones were purified and again titered, revealing good staining at 1.0 ug/ml.

In a second step, the three positive clones in frozen tissues were tested on formalin-fixed paraffin embedded (FFPE) tissues blocks using antigen retrieval techniques consisting of a steamer and different antigen retrieval solutions. Incubation and detection of primary antibody was done as with the frozen tissues. A panel of normal tissues as well as gastric carcinomas were analyzed. In formalin fixed parafin embedded tissues, the best staining was achieved by using an antigen-retrieval technique employing heating the slides for 30 minutes at 93° C. in an Tris-acetate (TA) buffer solution (pH 8.0, 1 mM). All three clones showed similar staining, and 342 was chosen for further analyses.

Figure 9:
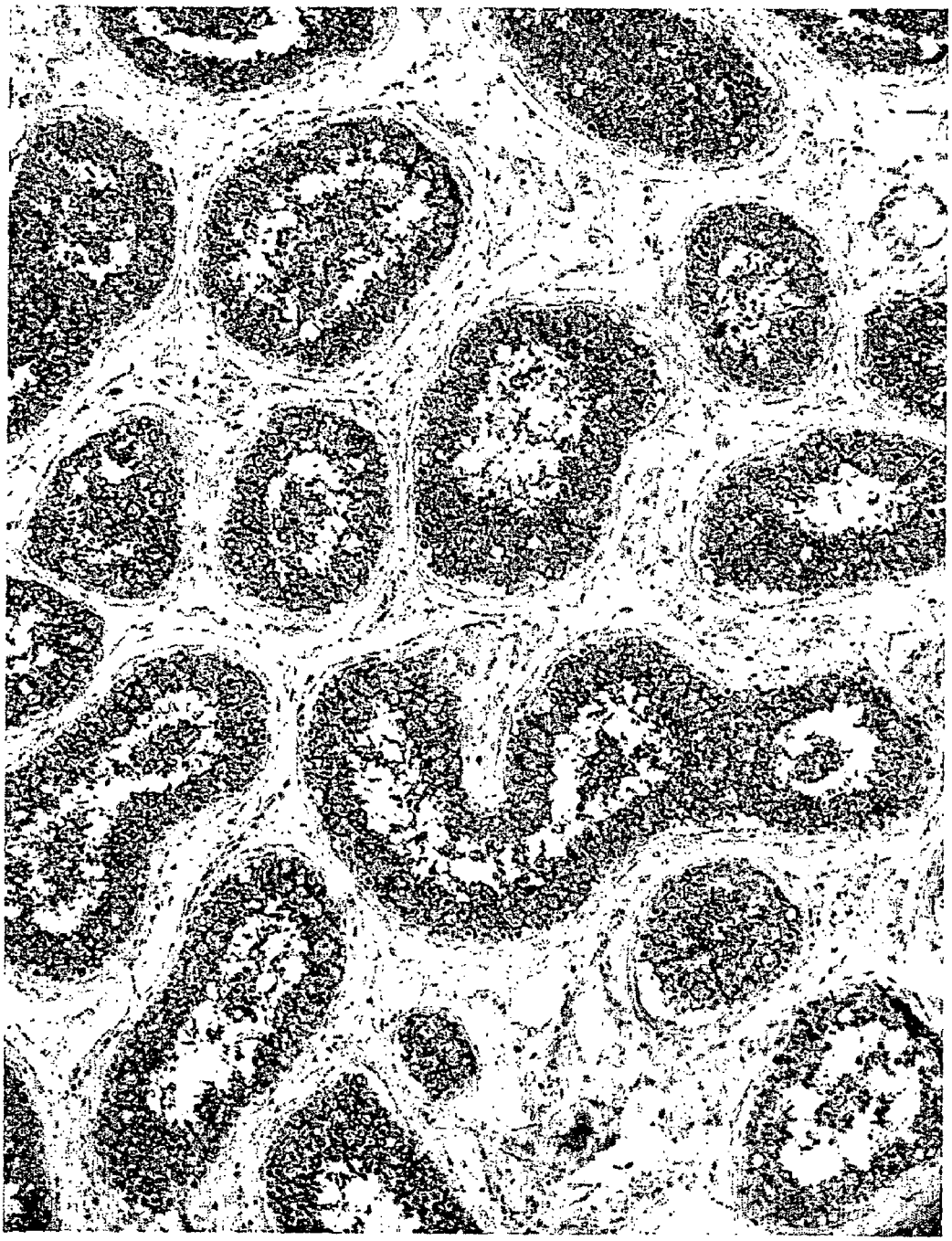
FIGS. 9 and 10 show immunohistochemical analyses of A34 expression in normal testis.
Figure 10:
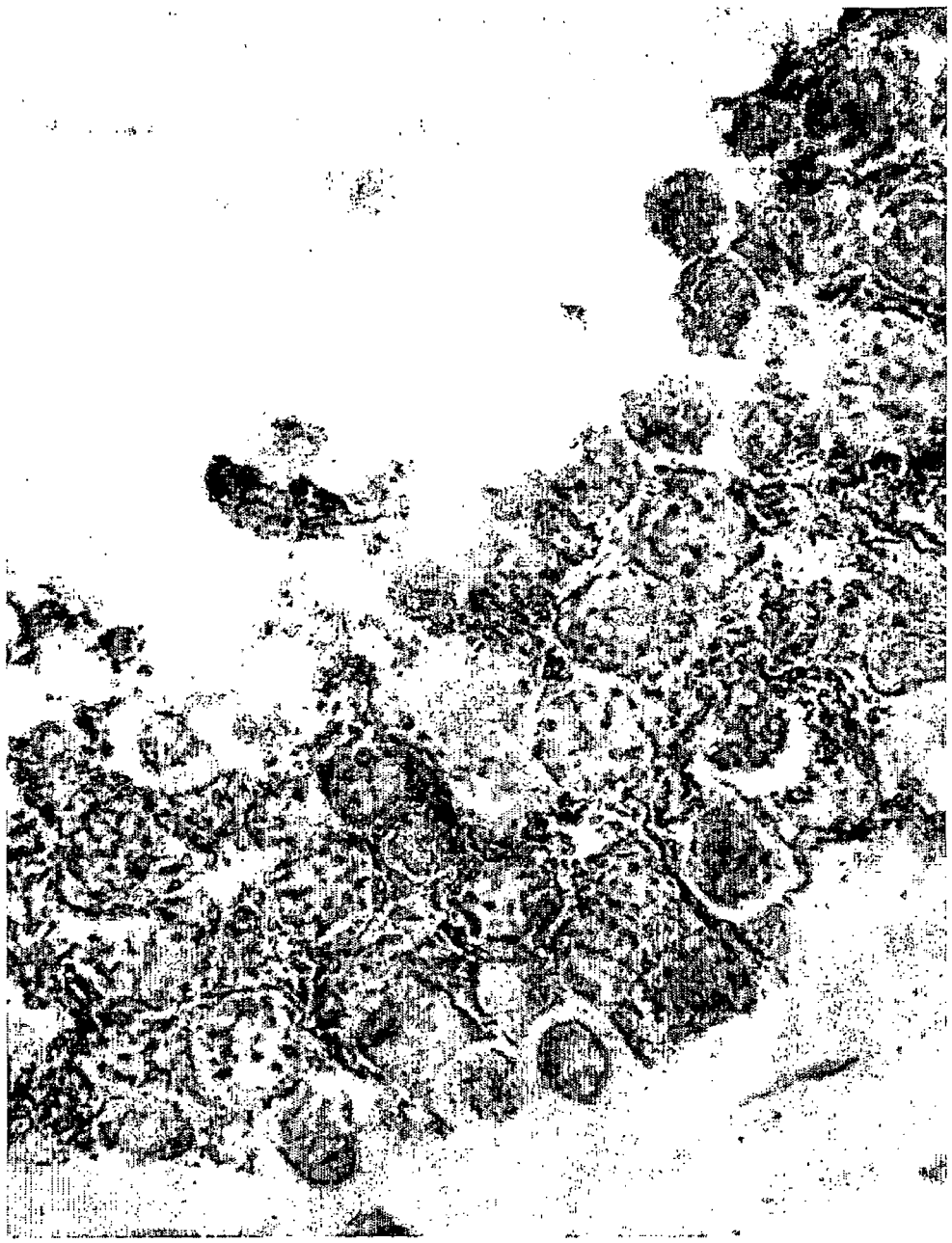
Figure 11:
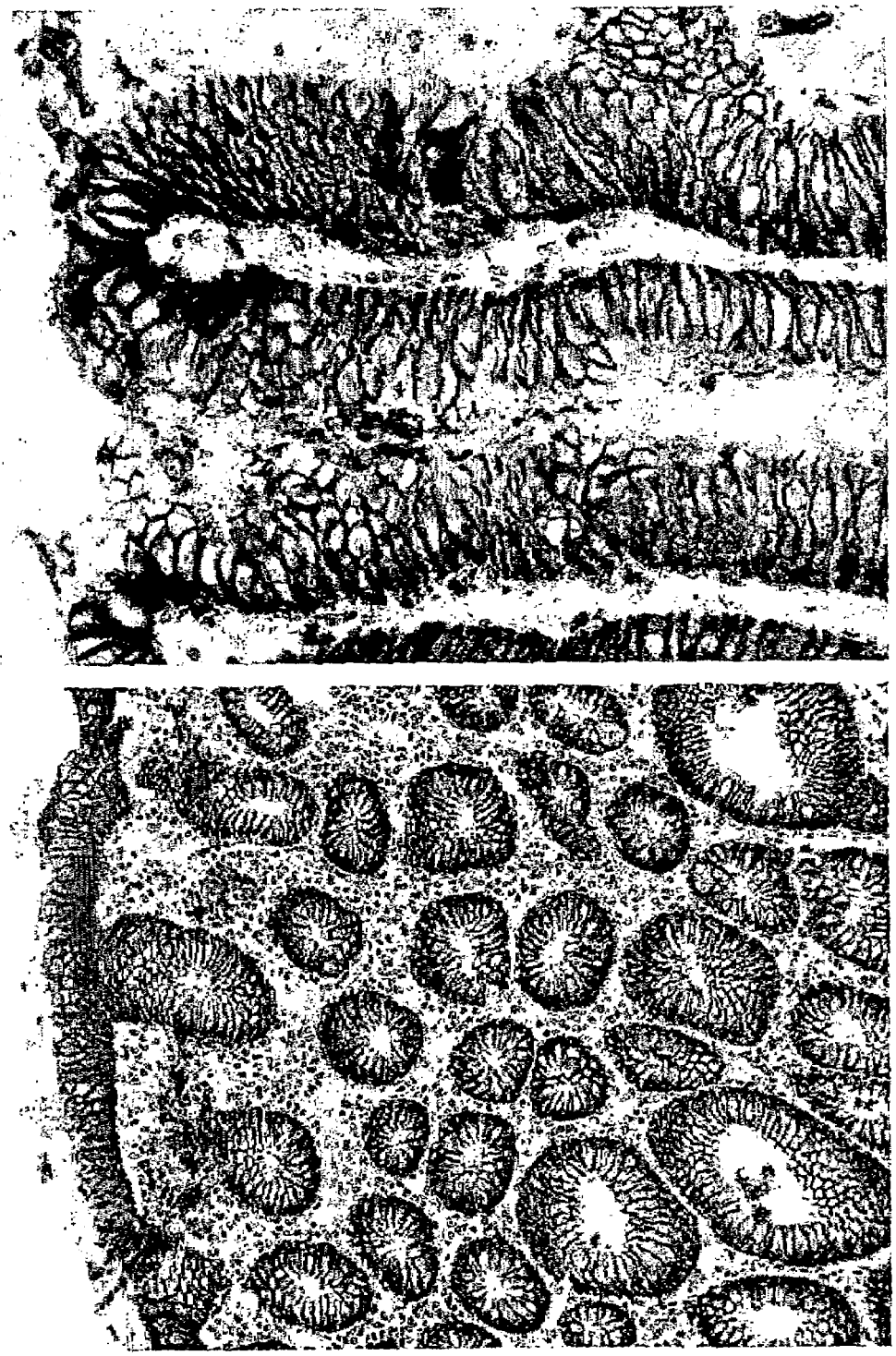
FIG. 11 shows an immunohistochemical analysis of A34 expression in normal stomach mucosa/surface epithelium.
Figure 14:
Figure 13:
Figure 16:
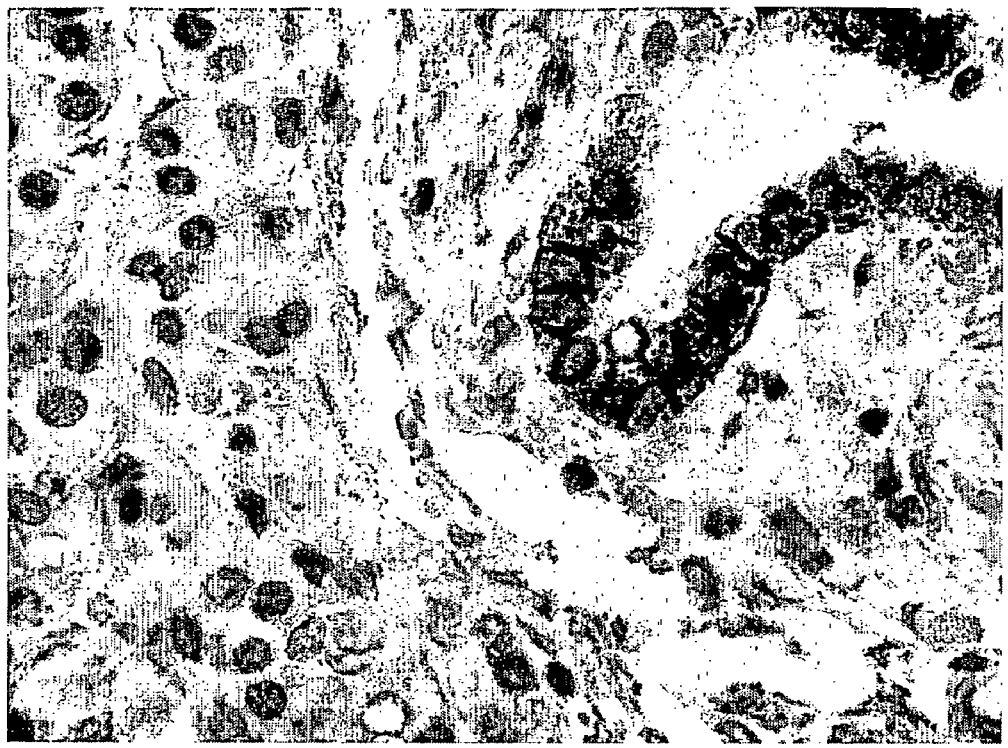
FIGS. 15 and 16 show an immunohistochemical analysis of A34 expression in normal pancreas.
Figure 15:
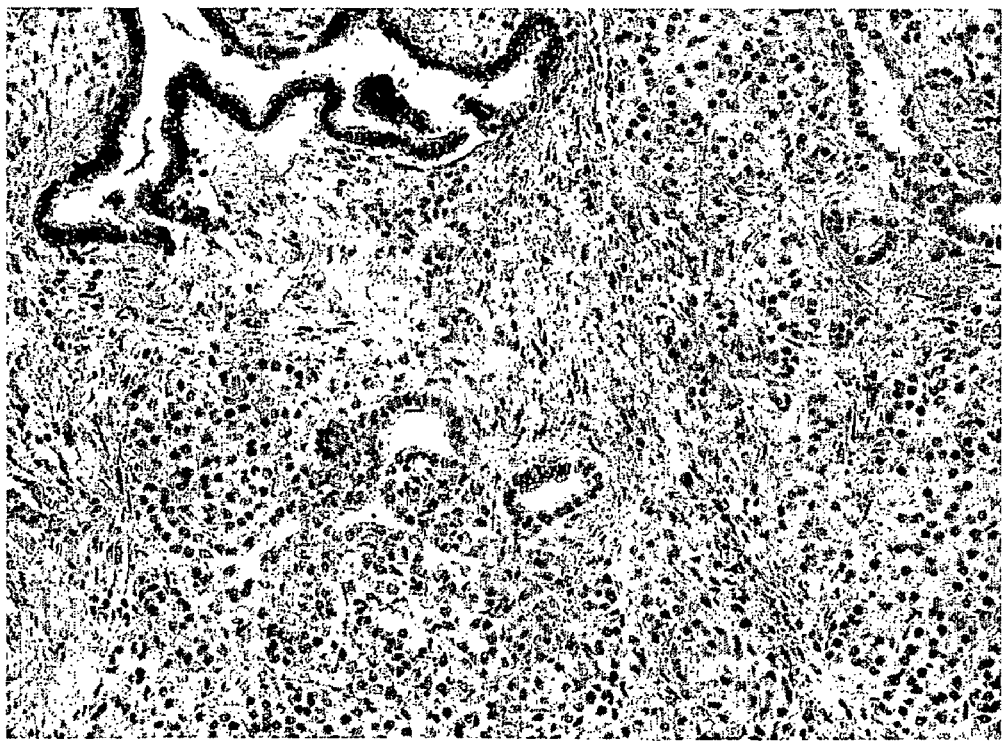
Figure 17:
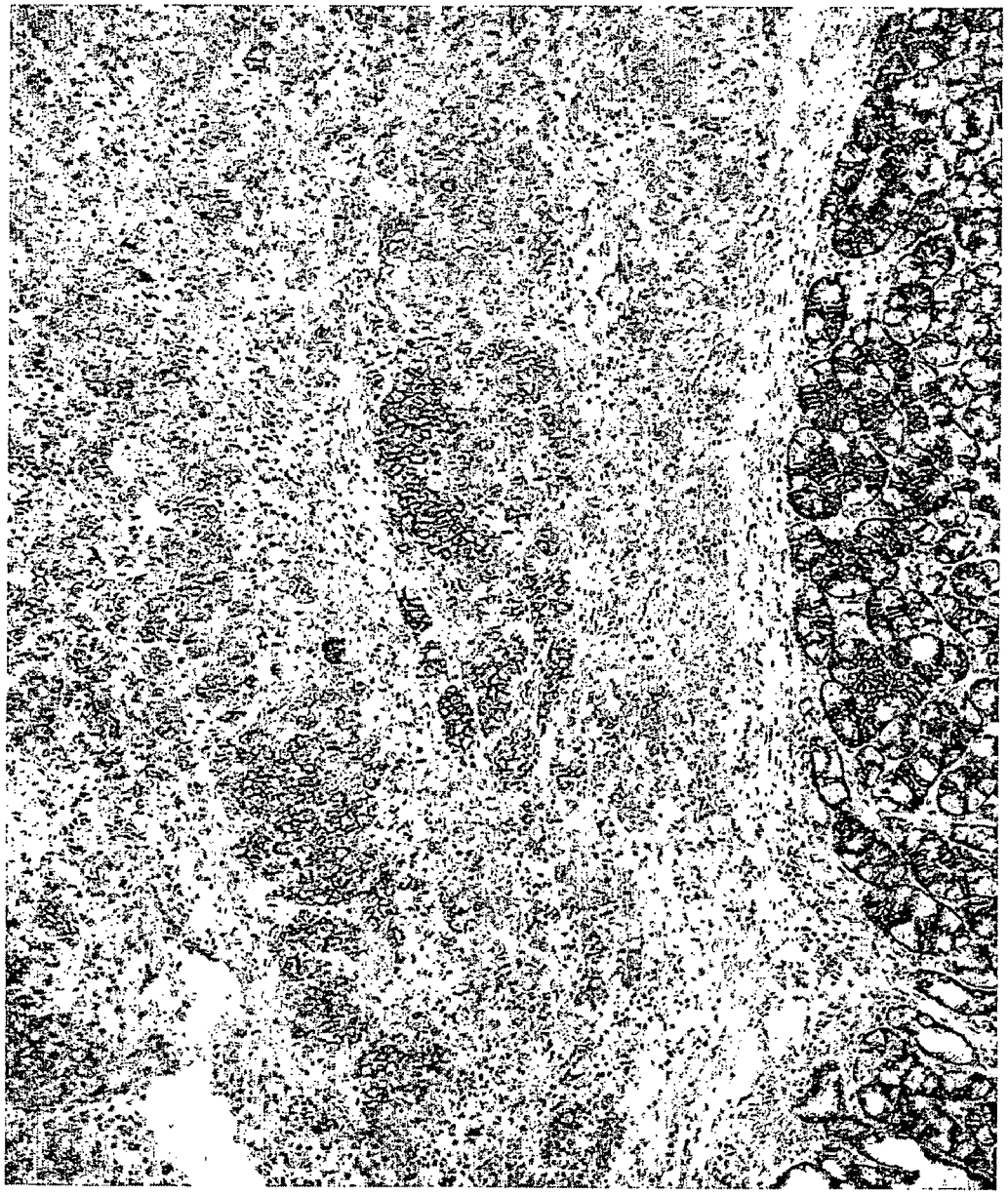
FIGS. 17-20 show immunohistochemical analyses of A34 expression in stomach carcinoma.
Figure 18:
Figure 19:
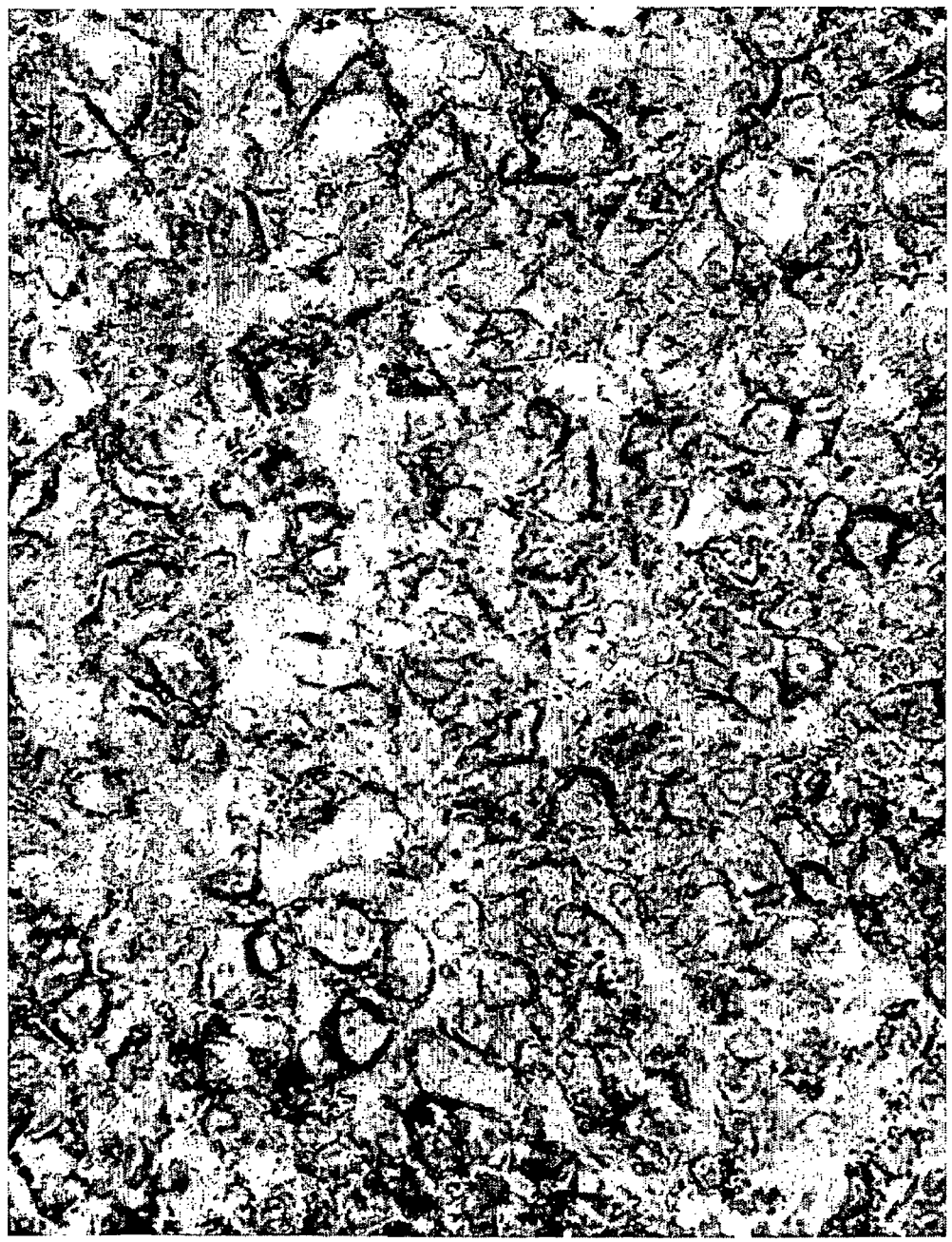
Figure 20:
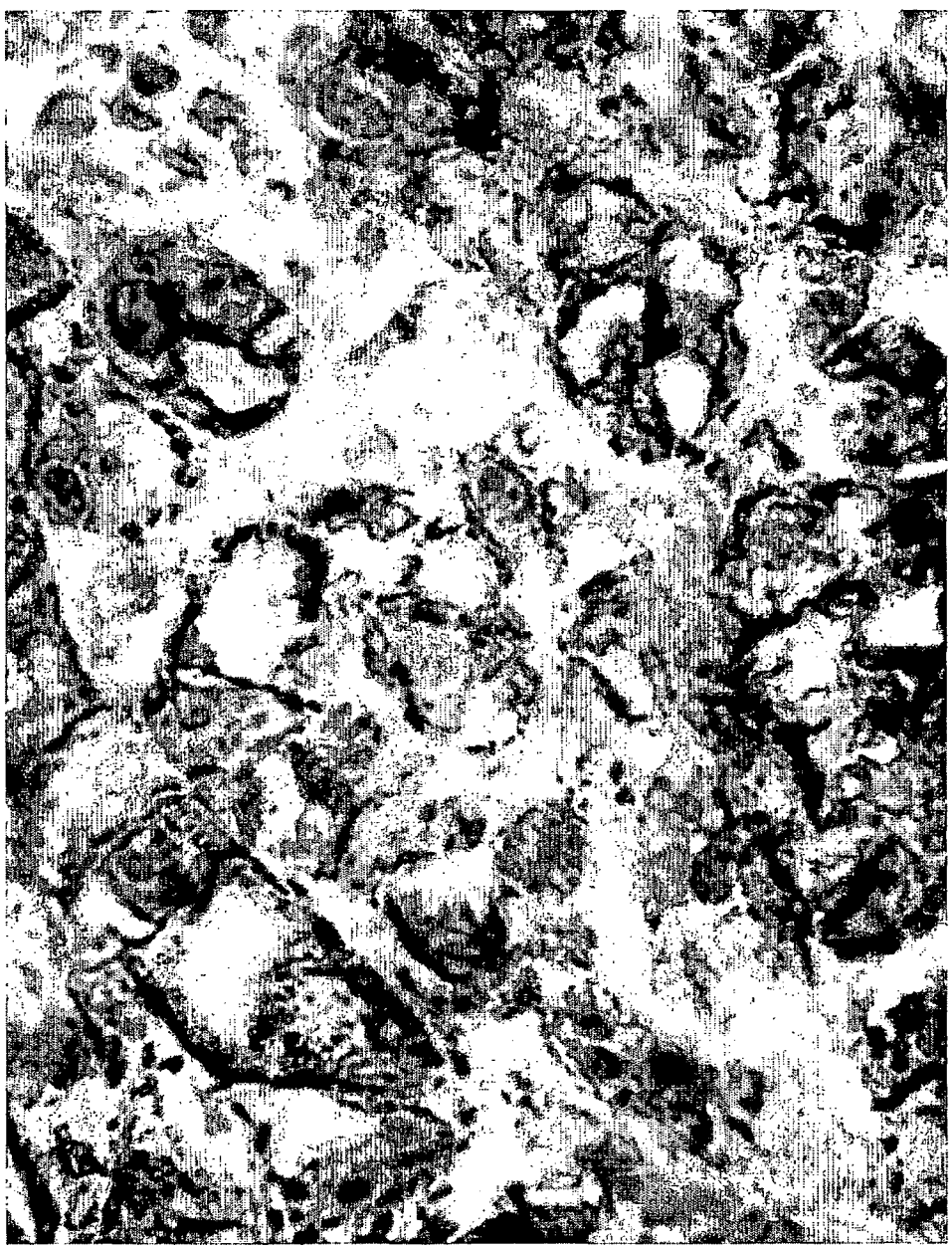

Results:

In normal tissues, immunoreactivity was predominantly present in stomach and testis. In stomach, intense staining was observed in the mucosa. There was mostly membranous and also cytoplasmic staining of all epithelial cellular components reaching from the surface epithelium to the bottom of the specialized glands (FIGS. 11-14). In testis, a cytoplasmic staining of the germ cells which was present in all tubules could be observed (FIGS. 9-10). In pancreas, a focal staining of the duct epithelium was occasionally seen (FIGS. 15-16). No staining was present in any other normal tissue, such as colon, esophagus, small intestine, lung, liver, skin and kidney.

In a panel of 20 normal tissues, A34 could only be found in stomach mucosa (FIGS. 11-14), testis (FIGS. 9-10), and, to a much lesser degree, in pancreas (FIGS. 15-16). In stomach, the epithehal cells throughout the entire mucosa were stained. No other tissue component was stained. The mucosal cells showed a typical membranous staining pattern. A similar staining pattern was observed in ductal epithelial cells of the pancreas, however, in pancreas, only focal cells were immunopositive.

In testis, a reactivity staining pattern was observed consisting entirely of germ cells. No staining was observed in the testicular interstitial tissue.

In a limited set of gastric, ovarian and esophageal carcinomas, A34 showed a mostly heterogeneous or sometimes homogeneous labeling of tumor cells. As in normal tissues, the immunoreactivity pattern was membranous.

The following tables represent, in tabular form, immunohistochemical analyses performed on gastric/stomach cancer cells, ovarian cancer cells, and esophageal carcinoma cells with A34 clone 342. "Neg" indicates a negative response and the plus signs indicate the percentage of stained tumor cells, where Focal: ~<5% (for very small numbers of cells); +: >5-25%; ++>25-50%; +++>50-75%; and ++++>75%. This grading is reproducible and conforms to standard procedures found in the literature.

TABLE 3

| Gastric/stomach cancer | |
|---|---|
| Sample | A34 staining |
| 1 | neg |
| 2 | neg |

TABLE 3-continued

| Gastric/stomach cancer | |
|---|---|
| Sample | A34 staining |
| 3 | neg |
| 4 | ++ |
| 5 | neg |
| 6 | neg |
| 7 | neg |
| 8 | neg |
| 9 | Foc. (single cells) |
| 10 | neg |
| 11 | Foc. w |
| 12 | neg |
| 13 | pos |
| 14 | Foc. w |
| 15 | neg |
| 16 | neg |
| 17 | Foc. |
| 18 | neg |
| 19 | Foc. |
| 20 | neg. |
| 21 | Foc. |
| 22 | Neg. |
| 23 | neg |
| 24 | neg |
| 25 | neg |
| 26 | neg |
| 27 | neg |
| 28 | neg |
| 29 | neg |
| 30 | neg |
| 31 | + |
| 32 | +++ |
| 33 | neg |
| 34 | neg |
| 35 | + |
| 36 | ++ |
| 37 | + |
| 38 | neg |
| 39 | neg |
| 40 | neg |
| 41 | ++++ |
| 42 | neg |
| 43 | + |
| Total | 14/43 |
| Foc | 6 |
| + | 4 |
| ++ | 2 |
| +++ | 1 |
| ++++ | 1 |

TABLE 4

| Ovarian cancer | |
|---|---|
| Sample | A34 |
| 1 | Neg |
| 2 | Neg |
| 3 | + |
| 4 | Neg |
| 5 | Neg |
| 6 | Neg |
| 7 | Neg |
| 8 | Neg |
| 9 | Neg |
| 10 | ++++ |
| 11 | Neg |
| 12 | Neg |
| 13 | Neg |
| 14 | Neg |
| 15 | Neg |
| 16 | Neg |
| 17 | Neg |
| 18 | Neg |

TABLE 4-continued

Ovarian cancer

| Sample | A34 | | |
|---|---|---|---|
| 19 | Neg | | |
| 20 | Neg | | |
| 21 | Neg | | |
| | Total | 2/21 | |
| | foc | — | |
| | + | 1 | |
| | ++ | — | |
| | +++ | — | |
| | ++++ | 1 | |

TABLE 5

Eosphaegeal carcinoma

| Sample | A34 staining | |
|---|---|---|
| 1 | − | |
| 2 | − | |
| 3 | + | |
| 4 | ++ | |
| 5 | − | |
| 6 | − | |
| 7 | + | |
| 8 | ++ | |
| 9 | ++ | |
| 10 | ++ | |
| 11 | + | |
| | Total | 7/11 |
| | Neg | 4 |
| | Foc | — |
| | + | 3 |
| | ++ | 4 |
| | +++ | — |
| | ++++ | — |

Table 6 indicates the immunohistochemical analyses of A34 protein expression in normal tissues as detected by A34 antibody clone 342. The majority of the tissues tested were negative. Stomach and testis were positive.

TABLE 6

| Tissue | A34 Clone 342 |
|---|---|
| Esophagus m 2x | — |
| Esophagus sub 2x | — |
| Stomach 1x | Pos |
| Stomach sub 1x | — |
| Small intestine duo m 1x | — |
| Small intestine duo sub 1x | — |
| liver | — |
| Small intestine m 2x | — |
| Small intestine sub 2x | — |
| Colon m 3x | — |
| Colon sub 3x | — |
| Appendix m 3x | — |
| Appendix sub 3x | — |
| Liver 3x | — |
| Gall bladder | Brownish hue |
| Pancreatic islets 3x | — |
| Pancreatic exo 3x | Duct epi.cut/hit in 1 pan |
| Mesentery | — |
| Thyroid | — |
| Synovia | — |
| Salivary gland 2x | — |
| Skeletal muscle 3x | — |
| Synovia | — |
| Adrenal gland med 4x | — |
| Adrenal gland cortex 4x | — |
| Lymph node 1x | — |
| Peripheral nerve 1x | — |
| Thymus 2x | — |
| Spleen 3x | — |
| Tonsil 3x | — |
| Lung alve 3x | — |
| Lung bro 2x | — |
| Pleura 2x | — |
| Prostate 2x | GC/surface |
| Kidney med 3x | — |
| Kidney cort 3x | — |
| Ureter 2x | — |
| UB m 3x | — |
| UB sub 3x | Muscl. Pos 1x |
| Testis 3x | Pos |
| Vagin 1x | — |
| Omentum 1x | — |
| Cervix 2 | — |
| Endometrium 3x | — |
| Fallopian tub 2x | — |
| Ovary 3x | — |
| Placenta villi 2x | — |
| Placenta plate 2x | — |
| Placenta am = pl 1x | — |
| Amnion 2x | — |
| Breast gland 3x | — |
| Breast duct 3x | — |
| Skin epithelium 3x | — |
| Skin dermis 3x | — |
| Valve 1x | — |

EXAMPLE 5

The stomach/testis-related expression profiles of both human and mouse A34 transcripts suggested that expression of these two orthologs may be under the control of similar regulatory sequences in their corresponding promoters. A comparison of DNA sequences located upstream of the human and mouse A34 start site revealed 64% nucleotide identity between the orthologous genes at positions 1 to 600 of the putative start site (80% identity from 1 to 300 of the putative start site). These regions may constitute the A34 promotor regions.

Like the human and mouse A33 gene, these putative A34 promotors lack a TATA box within 25-30 bp of the start site, indicating that mRNA transcription is independent of TATA sequences, but do contain a CAAT box, located at position 67 and 70 upstream of the human and murine ATG start site, respectively. Binding sites for 3 tissue specific transcription factors are highly conserved between the human and mouse A34 orthologs, including an intestinal specific homeobox transcription factor, CDX1, and 2 testis-related transcription factors, SRY and SOX-5. CDX1 binding sites, which are also found in the A33 orthologues, are present at 236 and 233 upstream of the human and murine ATG start site, respectively. Binding sites for the 2 testis-related transcription factors, SRY and SOX-5, overlap each other, and are found at positions 294 and 288 upstream of the human and murine ATG start site, respectively. The presence of binding sites for these 3 transcription factors in the putative A34 promotors is consistent with the stomach/testis-related mRNA expression profile of A34.

Human A34 Promotor Region:

```
GGTAGTGACAACTGCCAGTGTTTCAAAAAAGAGTAACATATCC        (SEQ ID NO: 16)
AGAGTTTGTTCACACAGAAATGAATGCTTTTTAGCTTCATAACCCCTGT
GCCCTTCCCGTGAGCCCCATCTCCCCAGGAAACGATATAGTACCAATTT
ACTAACTTAATTTGTAAAAGGAGGTTAGTGAATCAATTCTGTAAGACTC
ATGGAAATATTTGAAATTAATTAGCCTTGTCAGCTTTTATTTGCATAGG
CTCTCTTCCAACCATATCCCCCAGCCCAAGTACAACGTTTTAGTAAGAT
TGATTTTAAACAATGAGACTTAGAGAATCTGTGTACAAGGAGCTTGAAT
AATTTAAATGCGTGGGTTTATTATTAACACAGTAGCAAATATATCAAGG
AAACACGCCCCATGAAAAGTGTTTCAAAGAAACACAAATCTGTACTGAA
AAAAGTCTATACGCAATAAGTAAGCCCAAAGAGGCATGTTTGCTTGGC
GATGCCCAGCAGATAAGCCAGGCAAACCTCGGTGTGATCGAAGAAGCC
AATTTGAGACTCAGCCTAGTCCAGGCAAGCTACTGGCACCTGCTGCTCT
CAACTAACCTCCACACAATG
```

Murine A34 Promotor Region:

```
GGATTTGCTGACAGTCCAATCACTGGAAAGTGTTACTGGAAAT        (SEQ ID NO: 17)
GCCTTATTAGAGTTGAGATTTTTAGCCTGGGACTGGTACAAATTATTAC
ATAGGATGAAGGAGAAAGAAACCCAGGAGACCATTCAGGAAGCTGTTG
CTTTAGGCTAACGTAATATCTAGAACAAAATGGAAGCAGCAGGTTGGA
GATGGGACAAATCTACCATTCACTTTAGAAGCAGCAGGACCAAGATAT
CTTATGGGAAGAACTGGAGGAGGCCCTCCAAGTACAACTTTCTTTTTTT
AAAAAGGGTTGATTTTAAACAATGTAACCTAAGAGAATCTGTGTACAAA
GAACTGAAAGGATTTAAGTGCGTGGTTTATTATTAACACAGTAGCAAAT
ATATCAAGGGGACACACCCCGGGGGAAAAGGGTTTCAAATAAACACAG
ATTTGTTCAGAGAGAACTCAGTGCCCAATAAGCAAGCGTAAGGAGGCC
TATTTGCTTGGTGATGCCCAGCCGATAAGCCAGGCTGTGACTGAAGAA
GCCAATTTGAAACTCAGCCTAGTTCAGGCAGCCTTCGGACTGGCACCT
GCTGCTCCAAGCGACTTTCAGCATG
```

The ATG start codon is underlined in the murine and human sequences.

EXAMPLE 6

A33-like 3 (SEQ ID NO: 7) is located on human chromosome 1 at >gi|18547605|ref|XM_089096.1|, and has similarities with coxsackievirus and adenovirus receptor-like proteins. A33-like 3 polypeptide molecule (SEQ ID NO: 8) weighs approximately 40,085 Da (approx. 370 amino acids) which is 27% identical to A33 and 40% similar to A33 (using computer-based sequence comparison and identification tools that employ algorithms, i.e., BLAST or a similar program).

A33-like 3 protein has one transmembrane domain, extending from amino acids 4-26, and has two Ig-like domains extending from amino acids 37-128 and 160-241. Table 7 shows a comparison between A33-like 3 and the other family members, including the novel polypeptide A34.

TABLE 7

| Family Member Compared with A33-like 3 | Identity | Similarity | Location |
|---|---|---|---|
| A33 | 27% | 40% | 232 aa, A33-like 3 aa 29-256, A33 aa 28-228 |
| CAR | 33% | 49% | 231aa, A33-like 3 aa 29-256, CAR aa 26-229 |
| HCTX | 23% | 42% | 168 aa, A33-like 3 aa 95-258, hCTX aa 109-255 |
| ELAM | 25% | 40% | 168 aa, A33-like 3 aa 97-257, ELAM aa 100-244 |
| JAM1 | 24% | 33% | 219 aa, A33-like 3 aa 34-246, JAM1 aa 40-219 |
| JAM2 | 28% | 36% | 150 aa, A33-like 3 aa 108-250, JAM2 aa 91-225 |

TABLE 7-continued

| Family Member Compared with A33-like 3 | Identity | Similarity | Location |
|---|---|---|---|
| JAM3 | none | none | n/a |
| A34 (A33-like 2) | 24% | 45% | 161 aa, A33-like 3 aa 101-257 |

A33-like 3 mRNA expression in normal tissues is investigated in an initial experiment by RT-PCR according to the experimental procedure of Example 1 using the following primers:

```
A33L3F, bp 733
TGCCCATGTGCTGGACAGAG,        (SEQ ID NO: 18)

A33L3R, bp 1025
CACGTTGTTGGCCACTGTGC,        (SEQ ID NO: 19)
```

EXAMPLE 7

Recombinant protein A34 and A33-like 3, or fragments thereof, are produced from the appropriate isolated cDNA sequence. Mic, rabbits, or other appropriate mammals are immunized with at least one of recombinant or isolated A34 protein (either whole or appropriate antigenic fragments), and antibodies are generated and purified by standard techniques as detailed in the references cited previously and known to those of skill in the art.

EXAMPLE 8

Antibodies targeting the A34 and/or A33-like 3 antigens are used for both diagnostic and therapeutic purposes. For therapeutic purposes the naked (unconjugated) antibody itself is used as a therapeutic, for example, by eliciting a immunoresponse against a tumor by stimulating ADCC and/or CDC responses. The A34 and/or A33-like 3 specific antibodies are conjugated with a radioisotope or a chemotherapeutic or cytotoxic agent for both therapeutic and/or diagnostic purposes. The radioisotope is, for example, $^{125}$I, $^{131}$I, $^{99}$Tc, $^{90}$Y and $^{111}$In, or any other γ, α or β emitter. Those of skill in the art will appreciate that many methods are suitable for the conjugation of an antibody with a radioisotope, e.g., U.S. Pat. Nos. 5,160,723 and 5,851,526.

The antibodies that bind to A34 and/or A33-like 3 antigens are optionally conjugated with at least one chemotherapeutic agent, or at least one cytotoxic agent, or may be used in conjunction with such an agent. For example, the antibodies can be conjugated to, or used in combination therapy together with, QFA (an antifolate), BCNU, mercaptopurine, methotrexate, docetaxel, adriamycin or calicheamicin. These are all well known chemotherapeutics or cytotoxic drugs and conjugation, and combination use, of these with proteins, including antibodies, have been described, e.g. Hellstrom et al., *Methods Mol. Biol.* 166:3-16 (2001); Sievers et al., *Curr. Opin. Oncol.* 13(6):522-7 (2001); Winer et al., *Oncology* 61 Suppl 2:50-7 (2001).

The antibodies, or any fragments thereof, may also be conjugated or recombinantly fused to any cellular toxin, bacterial or other, e.g., pseudomonas exotoxin, ricin, or diptheria toxin. The part of the toxin used can be the whole toxin, or any particular domain of the toxin. Such antibody-toxin molecules have successfully been used for targeting and therapy of different kinds of cancers, see e.g., Pastan, *Biochim Biophys Acta.*, 1333(2):C1-6 (Oct. 24, 1997); Kreitman et al., *New Engl. J. Med.* 345(4):241-247 (2001); Schnell et al., *Leukemia* 14(1):129-35 (2000) and Ghetie et al., *Mol. Biotechnol.*, 18(3):251-68 (2001).

Other conjugation partners can also be conjugated to the antibodies used in the methods of this invention, for example, enzymes, and prodrugs, such as the ADEPT approach, e.g., Xu et al., *Clin Cancer Res.* 7(11):3314-24 (2001). Any method known in the art for preparing antibody conjugates may be used to generate conjugates useful in this invention. The A34 or A33-like 3 specific antibodies conjugated with a cytotoxic or chemotherapeutic agent may be administered to a patient in need thereof before, after, or concurrently with a non-conjugated form of an A34 or A33-like 3 specific antibody.

Examples describing drug conjugates, etc. are found in: Hellstrom et al., "Development and activities of the BR96-doxorubicin immunoconjugate," *Methods Mol Biol.* 166:3-16 (2001); Sievers et al., "Mylotarg: antibody-targeted chemotherapy comes of age," *Curr Opin Oncol.* 13(6):522-7 (2001); Winer et al., "New combinations with Herceptin in metastatic breast cancer," *Oncology* 61 Suppl 2:50-7 (2001); Pastan I., "Targeted therapy of cancer with recombinant immunotoxins," *Biochim Biophys Acta.* 1333(2):C1-6 (1997); Kreitman et al., "Efficacy of the anti-CD22 recombinant immunotoxin BL22 in chemotherapy-resistant hairy-cell leukemia," *New Engl J. Med.* 345(4):241-7 (2001); Schnell et al., "Treatment of refractory Hodgkin's lymphoma patients with an anti-CD25 ricin A-chain immunotoxin," *Leukemia* 14(1):129-35 (2000); Ghetie et al., "Chemical construction of immunotoxins," *Mol Biotechnol.* 18(3):251-68 (2001); Xu et al., "Strategies for enzyme/prodrug cancer therapy," *Clin. Cancer Res.* 7(11):3314-24 (2001); Hudson et al., "Recombinant antibodies for cancer diagnosis and therapy," *Expert Opin Biol Ther.* 1(5):845-55 (2001).

EXAMPLE 9

Humanized, fully human, and/or chimeric antibodies and/or immunoglobulin products which bind to A34 and/or A33-like 3 are used as targeting agents in conjunction with other cancer therapies. The antibody, fragment, or other immunoglobulin product is linked to an additional anti-cancer agent, and a therapeutically effective amount of the conjugate produced is administered to a patient in need thereof. Alternatively, the agent is linked to a label for detection. Examples of labels include radioactive isotopes and fluorescent markers. The linkage may be covalent or ionic in nature.

EXAMPLE 10

These antibodies, or antigenically active fragments thereof which bind to A34 and/or A33-like 3 are further manipulated by molecular biological techniques known in the art to make humanized antibodies. The antibodies may be fully or partially human.

EXAMPLE 11

Humanized, fully human, and/or chimeric antibodies and/or immunoglobulin products which bind to A34 and/or A33-like 3, or appropriately antigenic fragments that bind to at least one of A34 and A33-like 3, are combined with, or linked to, other agents, such as radioisotopes, chemotherapeutic agents, cytokines, cytotoxic agents, or other immunoglobulin products. The linkage may be ionic or covalent, and is formed by methods known in the art (see references cited above).

EXAMPLE 12

A composition of at least one immunoglobulin product (whether an antibody, a fragment, or an immunoglobulin linked to another agent, or any combination thereof), wherein said at least one immunoglobulin product binds to at least one of A34 and/or A33-like 3, will be formed by combining a therapeutically effective amount of said immunoglobulin product with a pharmaceutically acceptable carrier. This composition will then be administered to a patient in need thereof (i.e., a human or other mammal).

Such patients will be suffering from a disorder, such as a neoplastic disease, wherein the disorder expresses the antigen to which the immunoglobulin product binds (i.e., A34 or A33-like 3).

A composition, or treatment regimen, with at least one immunoglobulin product (whether an antibody, a fragment, or an immunoglobulin linked to another agent, or any combination thereof), wherein said at least one immunoglobulin product binds to at least one of A34 and/or A33-like 3, will be formed by combining said immunoglobulin product with a chemotherapeutic agent. The chemotherapeutic agents may be administered prior to, concurrently with, or after A34 and/or A33-like 3 specific immunoglobulin product is administered to the patient. Examples of chemotherapeutic drugs that could be used in such a combination are (but not limited to) oxaliplatin, irinotecan, topotecan, carmustine, vincristine, leucovorin, streptozocin, Orzel™ and fluoropyrimidines, e.g., 5-fluorouracil, ftoraflur, capecitabine, gemcitabine, floxuridine and fluoritine, and other nucleoside analogs, and vinca alkaloid analogs, including but not limited to vinblastine, navelbine, and vinzolidine, topoisomerase I inhibitors, including but not limited to topotecan and camptothecin, and other platinum analogs including but not limited to cisplatin and carboplatin.

A composition, or treatment regimen, with at least one immunoglobulin product (whether an antibody, a fragment, or an immunoglobulin linked to another agent, or any combination thereof), wherein said at least one immunoglobulin product binds to at least one of A34 and/or A33-like 3, is formed by combining said immunoglobulin product with another immunoglobulin product that is not specific for A34 or the A33 like 3 antigens. Examples of such immunoglobulins are antibodies targeting receptors of the Epidermal Growth Factor Receptor (EGFR) family of proteins, e.g., Cetuximab (Erbitux™, ImClone Systems Inc.) and Trastuzumab (Herceptin™, Genentech Inc.).

A composition, or treatment regimen, with at least one immunoglobulin product (whether an antibody, a fragment, or an immunoglobulin linked to another agent, or any combination thereof), wherein said at least one immunoglobulin product binds to at least one of A34 and/or A33-like 3, is formed by combining said immunoglobulin product with a small molecule signalling inhibitor. Examples of such small molecule signaling inhibitors are Imatinib Mesylate (Glivec®, Novartis AG) and Gefitinib (Iressa™, AstraZeneca Ltd.).

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations falling within the scope of the appended claims and equivalents thereof.

What is claimed is:

1. A substantially pure immunoglobulin molecule which binds specifically to A34 antigen wherein said immunoglobulin molecule comprises:
   1) at least one light chain variable region comprising a CDR1 region consisting of a sequence selected from SEQ ID NO: 32, SEQ ID NO: 38 and SEQ ID NO: 44; a CDR2 region consisting of the sequence of SEQ ID NO: 33 or SEQ ID NO: 45; and a CDR3 region consisting of the sequence of SEQ ID NO: 34 or SEQ ID NO: 46; and
   2) at least one heavy chain variable region comprising a CDR1 region consisting of a sequence selected from SEQ ID NO: 35, SEQ ID NO: 41 and SEQ ID NO: 47; a CDR2 region consisting of the sequence of SEQ ID NO: 36 or SEQ ID NO: 48; and a CDR3 region consisting of the sequence of SEQ ID NO: 37 or SEQ ID NO: 49.

2. A composition comprising a therapeutically effective amount of the molecule of claim 1 and at least one pharmaceutically acceptable carrier.

3. A composition comprising a therapeutically effective amount of an immunoglobulin according to claim 1 that binds to A34 and is conjugated to an anti-cancer agent, and at least one pharmaceutically acceptable carrier.

4. The immunoglobulin molecule of claim 1, wherein said immunoglobulin molecule is humanized.

5. The immunoglobulin molecule of claim 1, wherein said immunoglobulin molecule is recombinant.

6. An immunoglobulin molecule according to claim 1 that binds to A34 and is conjugated to at least one anti-cancer agent.

7. The immunoglobulin molecule according to claim 6, wherein said anti-cancer agent is selected from the group consisting of radioisotopes, chemotherapeutic agents, cytotoxic agents and combinations thereof.

8. The immunoglobulin molecule according to claim 7, wherein said anti-cancer agent is a radioisotope selected from the group consisting of $^{125}$I, $^{131}$I, $^{99}$Tc, $^{90}$Y and $^{111}$In.

9. The immunoglobulin molecule according to claim 6, wherein said anti-cancer agent comprises a chemotherapeutic agent or cytotoxic agent selected from the group consisting of QFA, antifolates, BCNU (carmustine), mercaptopurine, methotrexate, docetaxel, adriamycin, calicheamicin cellular toxin, bacterial toxin, pseudomonas exotoxin, ricin, diptheria toxin and combinations thereof.

10. The substantially pure immunoglobulin molecule according to claim 1, wherein the immunoglobulin molecule binds to an extracellular portion of A34.

11. A substantially pure immunoglobulin molecule which binds specifically to A34 antigen, wherein said immunoglobulin molecule comprises:

at least one heavy chain variable region selected from SEQ ID NO: 23, SEQ ID NO: 27, and SEQ ID NO: 31; and at least one light chain variable region selected from SEQ ID NO: 21, SEQ ID NO: 25, and SEQ ID NO: 29.

12. A composition comprising a therapeutically effective amount of the molecule of claim 11 and at least one pharmaceutically acceptable carrier.

13. A composition comprising a therapeutically effective amount of an immunoglobulin according to claim 11 that binds to A34 and is conjugated to an anti-cancer agent, and at least one pharmaceutically acceptable carrier.

14. The immunoglobulin molecule of claim 11, wherein said immunoglobulin molecule is humanized.

15. The immunoglobulin molecule of claim 11, wherein said immunoglobulin molecule is recombinant.

16. An immunoglobulin molecule according to claim 11 that binds to A34 and is conjugated to at least one anti-cancer agent.

17. The immunoglobulin molecule according to claim 16, wherein said anti-cancer agent is selected from the group consisting of radioisotopes, chemotherapeutic agents, cytotoxic agents and combinations thereof.

18. The immunoglobulin molecule according to claim 17, wherein said anti-cancer agent is a radioisotope selected from the group consisting of $^{125}I$, $^{131}I$, $^{99}Tc$, $^{90}Y$ and $^{111}In$.

19. The immunoglobulin molecule according to claim 16, wherein said anti-cancer agent comprises a chemotherapeutic agent or cytotoxic agent selected from the group consisting of QFA, antifolates, BCNU (carmustine), mercaptopurine, methotrexate, docetaxel, adriamycin, calicheamicin cellular toxin, bacterial toxin, pseudomonas exotoxin, ricin, diptheria toxin and combinations thereof.

20. The substantially pure immunoglobulin molecule according to claim 11, wherein the immunoglobulin molecule binds to an extracellular portion of A34.

* * * * *

SEQUENCE LISTING

<160> NUMBER OF SEQ ID NOS: 50

<210> SEQ ID NO 1
<211> LENGTH: 387
<212> TYPE: PRT
<213> ORGANISM: Homo sapiens

<400> SEQUENCE: 1

Met Val Phe Ala Phe Trp Lys Val Phe Leu Ile Leu Ser Cys Leu Ala
 1               5                  10                  15

Gly Gln Val Ser Val Val Gln Val Thr Ile Pro Asp Gly Phe Val Asn
            20                  25                  30

Val Thr Val Gly Ser Asn Val Thr Leu Ile Cys Ile Tyr Thr Thr Thr
        35                  40                  45

Val Ala Ser Arg Glu Gln Leu Ser Ile Gln Trp Ser Phe Phe His Lys
    50                  55                  60

Lys Glu Met Glu Pro Ile Ser Ile Tyr Phe Ser Gln Gly Gly Gln Ala
65                  70                  75                  80

Val Ala Ile Gly Gln Phe Lys Asp Arg Ile Thr Gly Ser Asn Asp Pro
                85                  90                  95

Gly Asn Ala Ser Ile Thr Ile Ser His Met Gln Pro Ala Asp Ser Gly
            100                 105                 110

Ile Tyr Ile Cys Asp Val Asn Asn Pro Pro Asp Phe Leu Gly Gln Asn
        115                 120                 125

Gln Gly Ile Leu Asn Val Ser Val Leu Val Lys Pro Ser Lys Pro Leu
    130                 135                 140

Cys Ser Val Gln Gly Arg Pro Glu Thr Gly His Thr Ile Ser Leu Ser
145                 150                 155                 160

Cys Leu Ser Ala Leu Gly Thr Pro Ser Pro Val Tyr Tyr Trp His Lys
                165                 170                 175

Leu Glu Gly Arg Asp Ile Val Pro Val Lys Glu Asn Phe Asn Pro Thr
            180                 185                 190

Thr Gly Ile Leu Val Ile Gly Asn Leu Thr Asn Phe Glu Gln Gly Tyr
        195                 200                 205

Tyr Gln Cys Thr Ala Ile Asn Arg Leu Gly Asn Ser Ser Cys Glu Ile
    210                 215                 220

Asp Leu Thr Ser Ser His Pro Glu Val Gly Ile Ile Val Gly Ala Leu
225                 230                 235                 240

Ile Gly Ser Leu Val Gly Ala Ala Ile Ile Ile Ser Val Val Cys Phe
                245                 250                 255

Ala Arg Asn Lys Ala Lys Ala Lys Ala Lys Glu Arg Asn Ser Lys Thr
            260                 265                 270

```
Ile Ala Glu Leu Glu Pro Met Thr Lys Ile Asn Pro Arg Gly Glu Ser
            275                 280                 285

Glu Ala Met Pro Arg Glu Asp Ala Thr Gln Leu Glu Val Thr Leu Pro
        290                 295                 300

Ser Ser Ile His Glu Thr Gly Pro Asp Thr Ile Gln Glu Pro Asp Tyr
305                 310                 315                 320

Glu Pro Lys Pro Thr Gln Glu Pro Ala Pro Glu Pro Ala Pro Gly Ser
                325                 330                 335

Glu Pro Met Ala Val Pro Asp Leu Asp Ile Glu Leu Glu Leu Glu Pro
            340                 345                 350

Glu Thr Gln Ser Glu Leu Glu Pro Glu Pro Glu Pro Glu Pro Glu Ser
            355                 360                 365

Glu Pro Gly Val Val Val Glu Pro Leu Ser Glu Asp Glu Lys Gly Val
            370                 375                 380

Val Lys Ala
385

<210> SEQ ID NO 2
<211> LENGTH: 319
<212> TYPE: PRT
<213> ORGANISM: Homo sapiens

<400> SEQUENCE: 2

Met Val Gly Lys Met Trp Pro Val Leu Trp Thr Leu Cys Ala Val Arg
  1               5                  10                  15

Val Thr Val Asp Ala Ile Ser Val Glu Thr Pro Gln Asp Val Leu Arg
                20                  25                  30

Ala Ser Gln Gly Lys Ser Val Thr Leu Pro Cys Thr Tyr His Thr Ser
            35                  40                  45

Thr Ser Ser Arg Glu Gly Leu Ile Gln Trp Asp Lys Leu Leu Leu Thr
        50                  55                  60

His Thr Glu Arg Val Val Ile Trp Pro Phe Ser Asn Lys Asn Tyr Ile
65                  70                  75                  80

His Gly Glu Leu Tyr Lys Asn Arg Val Ser Ile Ser Asn Asn Ala Glu
                85                  90                  95

Gln Ser Asp Ala Ser Ile Thr Ile Asp Gln Leu Thr Met Ala Asp Asn
            100                 105                 110

Gly Thr Tyr Glu Cys Ser Val Ser Leu Met Ser Asp Leu Glu Gly Asn
        115                 120                 125

Thr Lys Ser Arg Val Arg Leu Leu Val Leu Val Pro Pro Ser Lys Pro
    130                 135                 140

Glu Cys Gly Ile Glu Gly Glu Thr Ile Ile Gly Asn Asn Ile Gln Leu
145                 150                 155                 160

Thr Cys Gln Ser Lys Glu Gly Ser Pro Thr Pro Gln Tyr Ser Trp Lys
                165                 170                 175

Arg Tyr Asn Ile Leu Asn Gln Glu Gln Pro Leu Ala Gln Pro Ala Ser
            180                 185                 190

Gly Gln Pro Val Ser Leu Lys Asn Ile Ser Thr Asp Thr Ser Gly Tyr
        195                 200                 205

Tyr Ile Cys Thr Ser Ser Asn Glu Glu Gly Thr Gln Phe Cys Asn Ile
    210                 215                 220

Thr Val Ala Val Arg Ser Pro Ser Met Asn Val Ala Leu Tyr Val Gly
225                 230                 235                 240

Ile Ala Val Gly Val Val Ala Ala Leu Ile Ile Ile Gly Ile Ile Ile
```

```
                   245                 250                 255
Tyr Cys Cys Cys Cys Arg Gly Lys Asp Asp Asn Thr Glu Asp Lys Glu
                       260                 265                 270

Asp Ala Arg Pro Asn Arg Glu Ala Tyr Glu Glu Pro Pro Glu Gln Leu
        275                 280                 285

Arg Glu Leu Ser Arg Glu Arg Glu Glu Glu Asp Asp Tyr Arg Gln Glu
    290                 295                 300

Glu Gln Arg Ser Thr Gly Arg Glu Ser Pro Asp His Leu Asp Gln
305                 310                 315

<210> SEQ ID NO 3
<211> LENGTH: 1910
<212> TYPE: DNA
<213> ORGANISM: Homo sapiens

<400> SEQUENCE: 3
```

| | | | | |
|---|---|---|---|---|
| cttcttgtgg | tagggacctc | tcctcagtat | ttgaaactaa | ccagcatctg acagatttcg | 60 |
| aatttgtaaa | aaataccctc | gaagattcag | gaatgaagct | tctgtgtgaa ggattaaaac | 120 |
| agcccaactg | tgtattacag | acattgaggt | ggtaccggtg | ccttatctct tctgcttctt | 180 |
| gtggggctct | agcagctgtt | cttagcacca | gtcagtggct | cactgaactg gaatttagtg | 240 |
| agacaaaact | ggaagcttca | gctttgaaat | tgctctatgg | aggcttaaaa gatccaaatt | 300 |
| gcaaattaca | gaagctcaac | ttgcagtttt | ctttatctgt | aaccgctgca aaacttccag | 360 |
| ttggaatggt | tggaaattgt | tctggttttct | cgggatcatt | ggtgcaatct cattttggct | 420 |
| actgtcagga | cagttctttc | aaatgtgatc | tttgtaagct | gctctggcct tccaccagag | 480 |
| ttgctgctgc | aaaggattgt | gggagtccta | agtccttcct | atcagaaggg ctgaactggg | 540 |
| caggaagact | tgaggcagtg | gaggaggttt | tggggttggg | ggtgcttgta cagcccggtg | 600 |
| acccagcatc | tcagggtggg | gggcattgtg | aaaactatgg | gtcttttaga gacttggtgg | 660 |
| acttagaagt | caaggcagaa | ccaagcctga | gaaaaggtgg | tatggatctc cagagaccca | 720 |
| ccctacaagt | tgtcctcctt | tgcaaaatct | tctccctcaa | actatttctc tttattgcat | 780 |
| tgcctaattc | tcctggtcag | gttagtgtgg | tgcaagtgac | catcccagac ggtttcgtga | 840 |
| acgtgactgt | tggatctaat | gtcactctca | tctgcatcta | caccaccact gtggcctccc | 900 |
| gagaacagct | ttccatccag | tggtctttct | tccataagaa | ggagatggag ccaatttcta | 960 |
| tttactttc | tcaaggtgga | caagctgtag | ccatcgggca | atttaaagat cgaattacag | 1020 |
| ggtccaacga | tccaggtaat | gcatctatca | ctatctcgca | tatgcagcca gcagacagtg | 1080 |
| gaattacat | ctgcgatgtt | aacaaccccc | cagactttct | cggccaaaac caaggcatcc | 1140 |
| tcaacgtcag | tgtgttagtg | aaaccttcta | agcccctttg | tagcgttcaa ggaagaccag | 1200 |
| aaactggcca | cactatttcc | ctttcctgtc | tctctgcgct | tggaacacct tcccctgtgt | 1260 |
| actactggca | taaacttgag | ggaagagaca | tcgtgccagt | gaaagaaaac ttcaacccaa | 1320 |
| ccaccgggat | tttggtcatt | ggaaatctga | caaattttga | acaaggttat taccagtgta | 1380 |
| ctgccatcaa | cagacttggc | aatagttcct | gcgaaatcga | tctcacttct tcacatccag | 1440 |
| aagttggaat | cattgttggg | gccttgattg | gtagcctggt | aggtgccgcc atcatcatct | 1500 |
| ctgttgtgtg | cttcgcaagg | aataaggcaa | agcaaaggc | aaaagaaaga aattctaaga | 1560 |
| ccatcgcgga | acttgagcca | atgacaaaga | taaacccaag | gggagaaagc gaagcaatgc | 1620 |
| caagagaaga | cgctacccaa | ctagaagtaa | ctctaccatc | ttccattcat gagactggcc | 1680 |
| ctgataccat | ccaagaacca | gactatgagc | caaagcctac | tcaggagcct gccccagagc | 1740 |

```
ctgccccagg atcagagcct atggcagtgc ctgaccttga catcgagctg gagctggagc    1800
cagaaacgca gtcggaattg gagccagagc cagagccaga gccagagtca gagcctgggg    1860
ttgtagttga gcccttaagt gaagatgaaa agggagtggt taaggcatag                1910

<210> SEQ ID NO 4
<211> LENGTH: 402
<212> TYPE: PRT
<213> ORGANISM: Homo sapiens

<400> SEQUENCE: 4

Met Asp Leu Gln Arg Pro Thr Leu Gln Val Val Leu Cys Lys Ile
 1               5                  10                  15

Phe Ser Leu Lys Leu Phe Leu Phe Ile Ala Leu Pro Asn Ser Pro Gly
                20                  25                  30

Gln Val Ser Val Val Gln Val Thr Ile Pro Asp Gly Phe Val Asn Val
                35                  40                  45

Thr Val Gly Ser Asn Val Thr Leu Ile Cys Ile Tyr Thr Thr Thr Val
            50                  55                  60

Ala Ser Arg Glu Gln Leu Ser Ile Gln Trp Ser Phe Phe His Lys Lys
 65                  70                  75                  80

Glu Met Glu Pro Ile Ser Ile Tyr Phe Ser Gln Gly Gly Gln Ala Val
                85                  90                  95

Ala Ile Gly Gln Phe Lys Asp Arg Ile Thr Gly Ser Asn Asp Pro Gly
                100                 105                 110

Asn Ala Ser Ile Thr Ile Ser His Met Gln Pro Ala Asp Ser Gly Ile
            115                 120                 125

Tyr Ile Cys Asp Val Asn Asn Pro Pro Asp Phe Leu Gly Gln Asn Gln
130                 135                 140

Gly Ile Leu Asn Val Ser Val Leu Val Lys Pro Ser Lys Pro Leu Cys
145                 150                 155                 160

Ser Val Gln Gly Arg Pro Glu Thr Gly His Thr Ile Ser Leu Ser Cys
                165                 170                 175

Leu Ser Ala Leu Gly Thr Pro Ser Pro Val Tyr Tyr Trp His Lys Leu
                180                 185                 190

Glu Gly Arg Asp Ile Val Pro Val Lys Glu Asn Phe Asn Pro Thr Thr
                195                 200                 205

Gly Ile Leu Val Ile Gly Asn Leu Thr Asn Phe Glu Gln Gly Tyr Tyr
            210                 215                 220

Gln Cys Thr Ala Ile Asn Arg Leu Gly Asn Ser Ser Cys Glu Ile Asp
225                 230                 235                 240

Leu Thr Ser Ser His Pro Glu Val Gly Ile Val Gly Ala Leu Ile
                245                 250                 255

Gly Ser Leu Val Gly Ala Ala Ile Ile Ile Ser Val Val Cys Phe Ala
                260                 265                 270

Arg Asn Lys Ala Lys Ala Lys Ala Lys Glu Arg Asn Ser Lys Thr Ile
                275                 280                 285

Ala Glu Leu Glu Pro Met Thr Lys Ile Asn Pro Arg Gly Glu Ser Glu
                290                 295                 300

Ala Met Pro Arg Glu Asp Ala Thr Gln Leu Glu Val Thr Leu Pro Ser
305                 310                 315                 320

Ser Ile His Glu Thr Gly Pro Asp Thr Ile Gln Glu Pro Asp Tyr Glu
                325                 330                 335

Pro Lys Pro Thr Gln Glu Pro Ala Pro Glu Pro Ala Pro Gly Ser Glu
```

```
                340             345             350
Pro Met Ala Val Pro Asp Leu Asp Ile Glu Leu Glu Leu Glu Pro Glu
            355                 360                 365

Thr Gln Ser Glu Leu Glu Pro Glu Pro Glu Pro Glu Pro Glu Ser Glu
        370                 375                 380

Pro Gly Val Val Glu Pro Leu Ser Glu Asp Glu Lys Gly Val Val
385                 390                 395                 400

Lys Ala

<210> SEQ ID NO 5
<211> LENGTH: 1045
<212> TYPE: DNA
<213> ORGANISM: Homo sapiens

<400> SEQUENCE: 5
actgttggat ctaatgtcac tctcatctgc atctacacca ccactgtggc ctcccgagaa      60 cagcttttcca tccagtggtc tttcttccat aagaaggaga tggagccaat ttctatttac    120
ttttctcaag gtggacaagc tgtagccatc gggcaattta agatcgaat acagggtcc      180 aacgatccag gtaatgcatc tatcactatc tcgcatatgc agccagcaga cagtggaatt    240
tacatctgcg atgttaacaa ccccccagac tttctcggcc aaaaccaagg catcctcaac    300
gtcagtgtgt tagtgaaacc ttctaagccc ctttgtagcg ttcaaggaag accagaaact    360
ggccacacta tttcccttc ctgtctctct gcgcttggaa caccttcccc tgtgtactac    420
tggcataaac ttgagggaag agacatcgtg ccagtgaaaa aaacttcaa cccaaccacc     480 gggattttgg tcattggaaa tctgacaaat tttgaacaag ttattacca gtgtactgcc     540 atcaacagac ttggcaatag ttcctgcgaa atcgatctca cttcttcaca tccagaagtt    600
ggaatcattg ttgggggcctt gattggtagc ctggtaggtg ccgccatcat catctctgtt   660
gtgtgcttcg caaggaataa ggcaaaagca aaggcaaaag aaagaaattc taagaccatc    720
gcggaacttg agccaatgac aaagataaac ccaaggggag aaagcgaagc aatgccaaga    780
gaagacgcta cccaactaga agtaactcta ccatcttcca ttcatgagac tggccctgat    840
accatccaag aaccagacta tgagccaaag cctactcagg agcctgcccc agagcctgcc    900
ccaggatcag agcctatggc agtgcctgac cttgacatcg agctggagct ggagccagaa    960
acgcagtcgg aattggagcc agagccagag ccagagccag agtcagagcc tggggttgta   1020
gttgagccct aagtgaaga tgaaa                                          1045

<210> SEQ ID NO 6
<211> LENGTH: 348
<212> TYPE: PRT
<213> ORGANISM: Homo sapiens

<400> SEQUENCE: 6

Thr Val Gly Ser Asn Val Thr Leu Ile Cys Ile Tyr Thr Thr Thr Val
 1               5                  10                  15

Ala Ser Arg Glu Gln Leu Ser Ile Gln Trp Ser Phe Phe His Lys Lys
            20                  25                  30

Glu Met Glu Pro Ile Ser Ile Tyr Phe Ser Gln Gly Gly Gln Ala Val
        35                  40                  45

Ala Ile Gly Gln Phe Lys Asp Arg Ile Thr Gly Ser Asn Asp Pro Gly
    50                  55                  60

Asn Ala Ser Ile Thr Ile Ser His Met Gln Pro Ala Asp Ser Gly Ile
65                  70                  75                  80
```

```
Tyr Ile Cys Asp Val Asn Asn Pro Pro Asp Phe Leu Gly Gln Asn Gln
                    85                  90                  95

Gly Ile Leu Asn Val Ser Val Leu Val Lys Pro Ser Lys Pro Leu Cys
            100                 105                 110

Ser Val Gln Gly Arg Pro Glu Thr Gly His Thr Ile Ser Leu Ser Cys
        115                 120                 125

Leu Ser Ala Leu Gly Thr Pro Ser Pro Val Tyr Tyr Trp His Lys Leu
    130                 135                 140

Glu Gly Arg Asp Ile Val Pro Lys Glu Asn Phe Asn Pro Thr Thr
145                 150                 155                 160

Gly Ile Leu Val Ile Gly Asn Leu Thr Asn Phe Glu Gln Gly Tyr Tyr
                165                 170                 175

Gln Cys Thr Ala Ile Asn Arg Leu Gly Asn Ser Ser Cys Glu Ile Asp
            180                 185                 190

Leu Thr Ser Ser His Pro Glu Val Gly Ile Ile Val Gly Ala Leu Ile
        195                 200                 205

Gly Ser Leu Val Gly Ala Ala Ile Ile Ile Ser Val Val Cys Phe Ala
    210                 215                 220

Arg Asn Lys Ala Lys Ala Lys Ala Lys Glu Arg Asn Ser Lys Thr Ile
225                 230                 235                 240

Ala Glu Leu Glu Pro Met Thr Lys Ile Asn Pro Arg Gly Glu Ser Glu
                245                 250                 255

Ala Met Pro Arg Glu Asp Ala Thr Gln Leu Glu Val Thr Leu Pro Ser
            260                 265                 270

Ser Ile His Glu Thr Gly Pro Asp Thr Ile Gln Glu Pro Asp Tyr Glu
        275                 280                 285

Pro Lys Pro Thr Gln Glu Pro Ala Pro Glu Pro Ala Pro Gly Ser Glu
    290                 295                 300

Pro Met Ala Val Pro Asp Leu Asp Ile Glu Leu Glu Leu Glu Pro Glu
305                 310                 315                 320

Thr Gln Ser Glu Leu Glu Pro Glu Pro Glu Pro Glu Pro Glu Ser Glu
                325                 330                 335

Pro Gly Val Val Val Glu Pro Leu Ser Glu Asp Glu
            340                 345
```

<210> SEQ ID NO 7
<211> LENGTH: 1403
<212> TYPE: DNA
<213> ORGANISM: Homo sapiens

<400> SEQUENCE: 7

| | |
|---|---:|
| tgtgcaggca acaggaaaca aatacagagg gcagagcaag gattggtcag gacgggctta | 60 |
| gtgagaaagg ctctgaacga gacacacacc agctgcagct tcgtactgac gcctgccagc | 120 |
| tcctacacac cttcctgggc aactgccagc ggggcaaggc aggcctgggg ccaccctgca | 180 |
| ggcagtgtct gggccctcag ctccccctcc ctccacctac ccctcacac ccaccactac | 240 |
| gaccccacgg gatacccagc ccagacggag gaaacaccga gcctagagac atgagagttg | 300 |
| gaggagcatt ccaccttcta ctcgtgtgcc tgagcccagc actgctgtct gctgtgcgga | 360 |
| tcaacgggga tggacaggag gtcctgtacc tggcagaagg tgataatgtg aggctgggct | 420 |
| gccccctacgt cctggaccct gaggactatg gtcccaatgg gctggacatc gagtggatgc | 480 |
| aggtcaactc agaccccgcc caccaccgag agaacgtgtt ccttagttac aggacaagaa | 540 |
| ggatcaacca tggcagcctt ccccatctgc agcagagggt ccgctttgca gcctcagacc | 600 |

```
caagccagta cgatgcctcc atcaacctca tgaacctgca ggtatctgat acagccactt    660
atgagtgccg ggtgaagaag accaccatgg ccacccggaa ggtcattgtc actgtccaag    720
cacgacctgc agtgcccatg tgctggacag agggccacat gacatatggc aacgatgtgg    780
tgctgaagtg ctatgccagt gggggctccc agcccctctc ctacaagtgg gccaagatca    840
gtgggcacca ttcccctat cgagctgggt cttacacctc ccagcacagc taccactcag    900
agctgtccta ccaggagtcc ttccacagct ccataaacca aggcctgaac aatggggacc    960
tggtgttgaa ggatatctcc agagcagatg atgggctgta tcagtgcaca gtggccaaca   1020
acgtgggcta cagtgtttgt gtggtggagg tgaaggtctc agactcccgg cgtataggcg   1080
tgatcatcgg catcgtcctg ggctctctgc tcgcgctggg ctgcctggcc agaggacgcc   1140
gtggcgcccg ggtgcaaggc cagcgggcgc ggcagccgcg tcacccacct cctgggtac    1200 ccgacgcaga acgtcagccg ctccctgcgc cgcaatacgc gcctcccccc tgcggcggcc   1260
ccgaggacgt ggccctggcg ccctgcaccg ccgccgccgc ctgcgaagcg ggccctccc    1320 cggtctacgt caaggtcaag agcgcggagc cggctgactg cgccgagggg ccggtgcagt   1380
gcaagaacgg cctcttggtg tga                                           1403

<210> SEQ ID NO 8
<211> LENGTH: 370
<212> TYPE: PRT
<213> ORGANISM: Homo sapiens

<400> SEQUENCE: 8

Met Arg Val Gly Gly Ala Phe His Leu Leu Leu Val Cys Leu Ser Pro
  1               5                  10                  15

Ala Leu Leu Ser Ala Val Arg Ile Asn Gly Asp Gly Gln Glu Val Leu
                 20                  25                  30

Tyr Leu Ala Glu Gly Asp Asn Val Arg Leu Gly Cys Pro Tyr Val Leu
             35                  40                  45

Asp Pro Glu Asp Tyr Gly Pro Asn Gly Leu Asp Ile Glu Trp Met Gln
         50                  55                  60

Val Asn Ser Asp Pro Ala His His Arg Glu Asn Val Phe Leu Ser Tyr
 65                  70                  75                  80

Gln Asp Lys Arg Ile Asn His Gly Ser Leu Pro His Leu Gln Gln Arg
                 85                  90                  95

Val Arg Phe Ala Ala Ser Asp Pro Ser Gln Tyr Asp Ala Ser Ile Asn
            100                 105                 110

Leu Met Asn Leu Gln Val Ser Asp Thr Ala Thr Tyr Glu Cys Arg Val
        115                 120                 125

Lys Lys Thr Thr Met Ala Thr Arg Lys Val Ile Val Thr Val Gln Ala
    130                 135                 140

Arg Pro Ala Val Pro Met Cys Trp Thr Glu Gly His Met Thr Tyr Gly
145                 150                 155                 160

Asn Asp Val Val Leu Lys Cys Tyr Ala Ser Gly Gly Ser Gln Pro Leu
                165                 170                 175

Ser Tyr Lys Trp Ala Lys Ile Ser Gly His His Tyr Pro Tyr Arg Ala
            180                 185                 190

Gly Ser Tyr Thr Ser Gln His Ser Tyr His Ser Glu Leu Ser Tyr Gln
        195                 200                 205

Glu Ser Phe His Ser Ser Ile Asn Gln Gly Leu Asn Asn Gly Asp Leu
    210                 215                 220
```

```
Val Leu Lys Asp Ile Ser Arg Ala Asp Asp Gly Leu Tyr Gln Cys Thr
225                 230                 235                 240

Val Ala Asn Asn Val Gly Tyr Ser Val Cys Val Val Glu Val Lys Val
                245                 250                 255

Ser Asp Ser Arg Arg Ile Gly Val Ile Ile Gly Ile Val Leu Gly Ser
            260                 265                 270

Leu Leu Ala Leu Gly Cys Leu Ala Arg Gly Arg Arg Gly Ala Arg Val
        275                 280                 285

Gln Gly Gln Arg Ala Arg Gln Pro Arg His Pro Pro Gly Val Pro
    290                 295                 300

Asp Ala Glu Arg Gln Pro Leu Pro Ala Pro Gln Tyr Ala Pro Pro Pro
305                 310                 315                 320

Cys Gly Gly Pro Glu Asp Val Ala Leu Ala Pro Cys Thr Ala Ala Ala
                325                 330                 335

Ala Cys Glu Ala Gly Pro Ser Pro Val Tyr Val Lys Val Lys Ser Ala
            340                 345                 350

Glu Pro Ala Asp Cys Ala Glu Gly Pro Val Gln Cys Lys Asn Gly Leu
        355                 360                 365

Leu Val
    370

<210> SEQ ID NO 9
<211> LENGTH: 228
<212> TYPE: PRT
<213> ORGANISM: Homo sapiens

<400> SEQUENCE: 9

Gln Glu Val Leu Tyr Leu Ala Glu Gly Asp Asn Val Arg Leu Gly Cys
1               5                   10                  15

Pro Tyr Val Leu Asp Pro Glu Asp Tyr Gly Pro Asn Gly Leu Asp Ile
            20                  25                  30

Glu Trp Met Gln Val Asn Ser Asp Pro Ala His His Arg Glu Asn Val
        35                  40                  45

Phe Leu Ser Tyr Gln Asp Lys Arg Ile Asn His Gly Ser Leu Pro His
    50                  55                  60

Leu Gln Gln Arg Val Arg Phe Ala Ala Ser Asp Pro Ser Gln Tyr Asp
65                  70                  75                  80

Ala Ser Ile Asn Leu Met Asn Leu Gln Val Ser Asp Thr Ala Thr Tyr
                85                  90                  95

Glu Cys Arg Val Lys Lys Thr Thr Met Ala Thr Arg Lys Val Ile Val
            100                 105                 110

Thr Val Gln Ala Arg Pro Ala Val Pro Met Cys Trp Thr Glu Gly His
        115                 120                 125

Met Thr Tyr Gly Asn Asp Val Val Leu Lys Cys Tyr Ala Ser Gly Gly
    130                 135                 140

Ser Gln Pro Leu Ser Tyr Lys Trp Ala Lys Ile Ser Gly His His
145                 150                 155                 160

Pro Tyr Arg Ala Gly Ser Tyr Thr Ser Gln His Ser Tyr His Ser Glu
                165                 170                 175

Leu Ser Tyr Gln Glu Ser Phe His Ser Ser Ile Asn Gln Gly Leu Asn
            180                 185                 190

Asn Gly Asp Leu Val Leu Lys Asp Ile Ser Arg Ala Asp Asp Gly Leu
        195                 200                 205

Tyr Gln Cys Thr Val Ala Asn Asn Val Gly Tyr Ser Val Cys Val Val
    210                 215                 220
```

```
Glu Val Lys Val
225

<210> SEQ ID NO 10
<211> LENGTH: 201
<212> TYPE: PRT
<213> ORGANISM: Homo sapiens

<400> SEQUENCE: 10

Gln Asp Val Leu Arg Ala Ser Gln Gly Lys Ser Val Thr Leu Pro Cys
  1               5                  10                  15

Thr Tyr His Thr Ser Thr Ser Ser Arg Glu Gly Leu Ile Gln Trp Asp
                 20                  25                  30

Lys Leu Leu Leu Thr His Thr Glu Arg Val Val Ile Trp Pro Phe Ser
             35                  40                  45

Asn Lys Asn Tyr Ile His Gly Glu Leu Tyr Lys Asn Arg Val Ser Ile
         50                  55                  60

Ser Asn Asn Ala Glu Gln Ser Asp Ala Ser Ile Thr Ile Asp Gln Leu
 65                  70                  75                  80

Thr Met Ala Asp Asn Gly Thr Tyr Glu Cys Ser Val Ser Leu Met Ser
                 85                  90                  95

Asp Leu Glu Gly Asn Thr Lys Ser Arg Val Arg Leu Leu Val Leu Val
            100                 105                 110

Pro Pro Ser Lys Pro Glu Cys Gly Ile Glu Gly Glu Thr Ile Ile Gly
        115                 120                 125

Asn Asn Ile Gln Leu Thr Cys Gln Ser Lys Glu Gly Ser Pro Thr Pro
    130                 135                 140

Gln Tyr Ser Trp Lys Arg Tyr Asn Ile Leu Asn Gln Glu Gln Pro Leu
145                 150                 155                 160

Ala Gln Pro Ala Ser Gly Gln Pro Val Ser Leu Lys Asn Ile Ser Thr
                165                 170                 175

Asp Thr Ser Gly Tyr Tyr Ile Cys Thr Ser Ser Asn Glu Glu Gly Thr
            180                 185                 190

Gln Phe Cys Asn Ile Thr Val Ala Val
        195                 200

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
actgttggat ctaatgtcac                                                 20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
aaggtttcac taacacactg                                                 20

<210> SEQ ID NO 13
```

-continued

```
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gaaggagatg gagccaattt ctatt                                           25

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cctgtaattc gatctttaaa ttgcc                                           25

<210> SEQ ID NO 15
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
cttttctcaa ggtggacaag ctgtagccat c                                    31

<210> SEQ ID NO 16
<211> LENGTH: 600
<212> TYPE: DNA
<213> ORGANISM: Homo sapiens

<400> SEQUENCE: 16
ggtagtgaca actgccagtg tttcaaaaaa gagtaacata tccagagttt gttcacacag     60
aaatgaatgc ttttagcttc ataacccct gtgcccttcc cgtgagcccc atctccccag     120
gaaacgatat agtaccaatt tactaactta atttgtaaaa ggaggttagt gaatcaattc    180
tgtaagactc atggaaatat ttgaaattaa ttagccttgt cagcttttat ttgcataggc    240
tctcttccaa ccatatcccc cagcccaagt acaacgtttt agtaagattg atttttaaaca    300 atgagactta gagaatctgt gtacaaggag cttgaataat ttaaatgcgt gggtttatta    360
ttaacacagt agcaaatata tcaaggaaac acgccccatg aaaagtgttt caaagaaaca    420
caaatctgta ctgaaaaaag tctatacgca ataagtaagc ccaaagaggc atgtttgctt    480
ggcgatgccc agcagataag ccaggcaaac ctcggtgtga tcgaagaagc caatttgaga    540
ctcagcctag tccaggcaag ctactggcac ctgctgctct caactaacct ccacacaatg    600

<210> SEQ ID NO 17
<211> LENGTH: 600
<212> TYPE: DNA
<213> ORGANISM: Mus musculus

<400> SEQUENCE: 17
ggatttgctg acagtccaat cactggaaag tgttactgga aatgccttat tagagttgag     60 attttttagcc tggactggt acaaattatt acataggatg aaggagaaag aaacccagga    120
gaccattcag gaagctgttg ctttaggcta acgtaatatc tagaacaaaa tggaagcagc    180
```

-continued

```
aggttggaga tgggacaaat ctaccattca ctttagaagc agcaggacca agatatctta    240
tgggaagaac tggaggaggc cctccaagta caactttctt tttttaaaaa gggttgattt    300
taaacaatgt aacctaagag aatctgtgta caaagaactg aaaggattta agtgcgtggt    360
ttattattaa cacagtagca aatatatcaa ggggacacac cccgggggaa aagggtttca    420
aataaacaca gatttgttca gagagaactc agtgcccaat aagcaagcgt aaggaggcct    480
atttgcttgg tgatgcccag ccgataagcc aggctgtgac tgaagaagcc aatttgaaac    540
tcagcctagt tcaggcagcc ttcggactgg cacctgctgc tccaagcgac tttcagcatg    600
```

```
<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
tgcccatgtg ctggacagag                                                 20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
cacgttgttg gccactgtgc                                                 20

<210> SEQ ID NO 20
<211> LENGTH: 399
<212> TYPE: DNA
<213> ORGANISM: Mus musculus
<220> FEATURE:
<221> NAME/KEY: CDS
<222> LOCATION: (1)..(399)

<400> SEQUENCE: 20 atg agg tgc ctt gtt cag ttt ctg ggg ctg ctt gtg ctc tgg atc cct     48
Met Arg Cys Leu Val Gln Phe Leu Gly Leu Leu Val Leu Trp Ile Pro
  1               5                  10                  15 gga gcc att ggg gat att gtg atg act cag gct gca ccc tct gtc cct     96
Gly Ala Ile Gly Asp Ile Val Met Thr Gln Ala Ala Pro Ser Val Pro
             20                  25                  30 gtc act cct gga gag tca gta tcc atc tcc tgc agg tct agt acg agt    144
Val Thr Pro Gly Glu Ser Val Ser Ile Ser Cys Arg Ser Ser Thr Ser
         35                  40                  45 ctc ctg cat agt aat ggc aac act tac ttg tat tgg ttc ctg cag agg    192
Leu Leu His Ser Asn Gly Asn Thr Tyr Leu Tyr Trp Phe Leu Gln Arg
     50                  55                  60 cca ggc cag tct cct cag ctc ctg ata tat cgg atg tcc aac ctt gcc    240
Pro Gly Gln Ser Pro Gln Leu Leu Ile Tyr Arg Met Ser Asn Leu Ala
 65                  70                  75                  80 tca gga gtc cca gac agg ttc agt ggc agt ggg tca gga act gct ttc    288
Ser Gly Val Pro Asp Arg Phe Ser Gly Ser Gly Ser Gly Thr Ala Phe
                 85                  90                  95 aca ctg aga atc agt aga gtg gag gct gag gat gtg ggt att tat tac    336
Thr Leu Arg Ile Ser Arg Val Glu Ala Glu Asp Val Gly Ile Tyr Tyr
            100                 105                 110
```

```
tgt atg caa cat cta gaa tat cct ttc acg ttc gga ggg ggg acc aaa      384
Cys Met Gln His Leu Glu Tyr Pro Phe Thr Phe Gly Gly Gly Thr Lys
        115                 120                 125 ctg gaa ata aaa cgg                                                   399
Leu Glu Ile Lys Arg
    130

<210> SEQ ID NO 21
<211> LENGTH: 133
<212> TYPE: PRT
<213> ORGANISM: Mus musculus

<400> SEQUENCE: 21

Met Arg Cys Leu Val Gln Phe Leu Gly Leu Leu Val Leu Trp Ile Pro
 1               5                  10                  15

Gly Ala Ile Gly Asp Ile Val Met Thr Gln Ala Ala Pro Ser Val Pro
                20                  25                  30

Val Thr Pro Gly Glu Ser Val Ser Ile Ser Cys Arg Ser Ser Thr Ser
            35                  40                  45

Leu Leu His Ser Asn Gly Asn Thr Tyr Leu Tyr Trp Phe Leu Gln Arg
        50                  55                  60

Pro Gly Gln Ser Pro Gln Leu Leu Ile Tyr Arg Met Ser Asn Leu Ala
 65                 70                  75                  80

Ser Gly Val Pro Asp Arg Phe Ser Gly Ser Gly Ser Gly Thr Ala Phe
                85                  90                  95

Thr Leu Arg Ile Ser Arg Val Glu Ala Glu Asp Val Gly Ile Tyr Tyr
            100                 105                 110

Cys Met Gln His Leu Glu Tyr Pro Phe Thr Phe Gly Gly Gly Thr Lys
        115                 120                 125

Leu Glu Ile Lys Arg
    130

<210> SEQ ID NO 22
<211> LENGTH: 423
<212> TYPE: DNA
<213> ORGANISM: Mus musculus
<220> FEATURE:
<221> NAME/KEY: CDS
<222> LOCATION: (1)..(423)

<400> SEQUENCE: 22 atg aac ttt ggg ttc agc ttg gtt ttc ctt gcc ctt att tta aaa ggt      48
Met Asn Phe Gly Phe Ser Leu Val Phe Leu Ala Leu Ile Leu Lys Gly
 1               5                  10                  15 gtc cag tgt gag gtg gag ctg gtg gag tct ggg gga ggc cta gtg cag      96
Val Gln Cys Glu Val Glu Leu Val Glu Ser Gly Gly Gly Leu Val Gln
                20                  25                  30 cct gga ggg tcc ctg aaa ctc tcc tgt gca gcc tct gga ttc acc ttc     144
Pro Gly Gly Ser Leu Lys Leu Ser Cys Ala Ala Ser Gly Phe Thr Phe
            35                  40                  45 agt act ttt ggc atg tct tgg gtt cgc cag act cca gac aag agg ctg     192
Ser Thr Phe Gly Met Ser Trp Val Arg Gln Thr Pro Asp Lys Arg Leu
        50                  55                  60 gag ttg gtc gca acc att aat agt aat ggt ggt agg acc tat tat cta     240
Glu Leu Val Ala Thr Ile Asn Ser Asn Gly Gly Arg Thr Tyr Tyr Leu
 65                 70                  75                  80 gac agt gtg aag ggc cga ttc acc atc tcc aga gaa aat gcc aag aac     288
Asp Ser Val Lys Gly Arg Phe Thr Ile Ser Arg Glu Asn Ala Lys Asn
                85                  90                  95 acc ctg tac ctg caa atg agc agt ctg aag tct gag gac aca gcc atg     336
```

```
Thr Leu Tyr Leu Gln Met Ser Ser Leu Lys Ser Glu Asp Thr Ala Met
            100                 105                 110 tat tac tgt gca aga gat ggg gga cta cta cgg gat tcc gcc tgg ttt       384
Tyr Tyr Cys Ala Arg Asp Gly Gly Leu Leu Arg Asp Ser Ala Trp Phe
            115                 120                 125 gct tac tgg ggc caa ggg act ctg gtc act gtc tct gca                   423
Ala Tyr Trp Gly Gln Gly Thr Leu Val Thr Val Ser Ala
            130                 135                 140
```

<210> SEQ ID NO 23
<211> LENGTH: 141
<212> TYPE: PRT
<213> ORGANISM: Mus musculus

<400> SEQUENCE: 23

```
Met Asn Phe Gly Phe Ser Leu Val Phe Leu Ala Leu Ile Leu Lys Gly
  1               5                  10                  15

Val Gln Cys Glu Val Glu Leu Val Glu Ser Gly Gly Gly Leu Val Gln
             20                  25                  30

Pro Gly Gly Ser Leu Lys Leu Ser Cys Ala Ala Ser Gly Phe Thr Phe
         35                  40                  45

Ser Thr Phe Gly Met Ser Trp Val Arg Gln Thr Pro Asp Lys Arg Leu
     50                  55                  60

Glu Leu Val Ala Thr Ile Asn Ser Asn Gly Gly Arg Thr Tyr Tyr Leu
 65                  70                  75                  80

Asp Ser Val Lys Gly Arg Phe Thr Ile Ser Arg Glu Asn Ala Lys Asn
                 85                  90                  95

Thr Leu Tyr Leu Gln Met Ser Ser Leu Lys Ser Glu Asp Thr Ala Met
            100                 105                 110

Tyr Tyr Cys Ala Arg Asp Gly Gly Leu Leu Arg Asp Ser Ala Trp Phe
            115                 120                 125

Ala Tyr Trp Gly Gln Gly Thr Leu Val Thr Val Ser Ala
            130                 135                 140
```

<210> SEQ ID NO 24
<211> LENGTH: 399
<212> TYPE: DNA
<213> ORGANISM: Mus musculus
<220> FEATURE:
<221> NAME/KEY: CDS
<222> LOCATION: (1)..(399)

<400> SEQUENCE: 24

```
atg agg tgc ctt gct cag ctt ctg ggg ctg ctt gtg ctc tgg atc cct        48
Met Arg Cys Leu Ala Gln Leu Leu Gly Leu Leu Val Leu Trp Ile Pro
  1               5                  10                  15 gga gcc att ggg gat att gtg atg act cag gct gca ccc tct gta cct        96
Gly Ala Ile Gly Asp Ile Val Met Thr Gln Ala Ala Pro Ser Val Pro
             20                  25                  30 gtc act cct gga gag tca gta tcc atc tcc tgc agg tct agt acg agt       144
Val Thr Pro Gly Glu Ser Val Ser Ile Ser Cys Arg Ser Ser Thr Ser
         35                  40                  45 ctc ctg cat ggt aat ggc aac act tac ttg tat tgg ttc ctg cag agg       192
Leu Leu His Gly Asn Gly Asn Thr Tyr Leu Tyr Trp Phe Leu Gln Arg
     50                  55                  60 cca ggc cag tct cct cag ctc ctg ata tat cgg atg tcc aac ctt gcc       240
Pro Gly Gln Ser Pro Gln Leu Leu Ile Tyr Arg Met Ser Asn Leu Ala
 65                  70                  75                  80 tca gga gtc cca gac agg ttc agt ggc agt ggg tca gga act gct ttc       288
Ser Gly Val Pro Asp Arg Phe Ser Gly Ser Gly Ser Gly Thr Ala Phe
```

-continued

```
                         85                  90                  95
aca ctg aga atc agt aga gtg gag gct gag gat gtg ggt att tat tac    336
Thr Leu Arg Ile Ser Arg Val Glu Ala Glu Asp Val Gly Ile Tyr Tyr
            100                 105                 110 tgt atg cag cat cta gaa tat cct ttc acg ttc gga ggg ggg acc aag    384
Cys Met Gln His Leu Glu Tyr Pro Phe Thr Phe Gly Gly Gly Thr Lys
        115                 120                 125 ctg gaa ata aaa cgg                                                399
Leu Glu Ile Lys Arg
    130
```

<210> SEQ ID NO 25
<211> LENGTH: 133
<212> TYPE: PRT
<213> ORGANISM: Mus musculus

<400> SEQUENCE: 25

Met Arg Cys Leu Ala Gln Leu Leu Gly Leu Leu Val Leu Trp Ile Pro
 1               5                  10                  15

Gly Ala Ile Gly Asp Ile Val Met Thr Gln Ala Ala Pro Ser Val Pro
                20                  25                  30

Val Thr Pro Gly Glu Ser Val Ser Ile Ser Cys Arg Ser Ser Thr Ser
            35                  40                  45

Leu Leu His Gly Asn Gly Asn Thr Tyr Leu Tyr Trp Phe Leu Gln Arg
        50                  55                  60

Pro Gly Gln Ser Pro Gln Leu Leu Ile Tyr Arg Met Ser Asn Leu Ala
    65                  70                  75                  80

Ser Gly Val Pro Asp Arg Phe Ser Gly Ser Gly Ser Gly Thr Ala Phe
                85                  90                  95

Thr Leu Arg Ile Ser Arg Val Glu Ala Glu Asp Val Gly Ile Tyr Tyr
            100                 105                 110

Cys Met Gln His Leu Glu Tyr Pro Phe Thr Phe Gly Gly Gly Thr Lys
        115                 120                 125

Leu Glu Ile Lys Arg
    130

<210> SEQ ID NO 26
<211> LENGTH: 423
<212> TYPE: DNA
<213> ORGANISM: Mus musculus
<220> FEATURE:
<221> NAME/KEY: CDS
<222> LOCATION: (1)..(423)

<400> SEQUENCE: 26

```
atg gac ttt ggg ttc agc ttg gtt ttc ctt gcc ctt att tta aaa ggt     48
Met Asp Phe Gly Phe Ser Leu Val Phe Leu Ala Leu Ile Leu Lys Gly
 1               5                  10                  15 gtc cag tgt gag gtg gag ctg gtg gag tct ggg gga ggc tta gtg cag     96
Val Gln Cys Glu Val Glu Leu Val Glu Ser Gly Gly Gly Leu Val Gln
                20                  25                  30 cct gga ggg tcc ctg aaa ctc tcc tgt gca gcc tct gga ttc acc ttc    144
Pro Gly Gly Ser Leu Lys Leu Ser Cys Ala Ala Ser Gly Phe Thr Phe
            35                  40                  45 agt agt tat ggc atg tct tgg gtt cgc cag act cca gac aag agg ctg    192
Ser Ser Tyr Gly Met Ser Trp Val Arg Gln Thr Pro Asp Lys Arg Leu
        50                  55                  60 gag ttg gtc gca acc att aat agt aat ggt ggt agg acc tat tat cta    240
Glu Leu Val Ala Thr Ile Asn Ser Asn Gly Gly Arg Thr Tyr Tyr Leu
    65                  70                  75                  80
```

```
gac agt gtg aag ggc cga ttc acc atc tcc aga gac aat gcc aag aac    288
Asp Ser Val Lys Gly Arg Phe Thr Ile Ser Arg Asp Asn Ala Lys Asn
             85                  90                  95 acc ctg tac ctg caa atg agc agt ctg aag tct gag gac aca gcc atg    336
Thr Leu Tyr Leu Gln Met Ser Ser Leu Lys Ser Glu Asp Thr Ala Met
        100                 105                 110 tat tac tgt gca aga gat ggg gga ctc cta cga gat tcc gcc tgg ttt    384
Tyr Tyr Cys Ala Arg Asp Gly Gly Leu Leu Arg Asp Ser Ala Trp Phe
    115                 120                 125 gct tac tgg ggc caa ggg act ctg gtc act gtc tct gca                423
Ala Tyr Trp Gly Gln Gly Thr Leu Val Thr Val Ser Ala
130                 135                 140

<210> SEQ ID NO 27
<211> LENGTH: 141
<212> TYPE: PRT
<213> ORGANISM: Mus musculus

<400> SEQUENCE: 27

Met Asp Phe Gly Phe Ser Leu Val Phe Leu Ala Leu Ile Leu Lys Gly
 1               5                  10                  15

Val Gln Cys Glu Val Glu Leu Val Glu Ser Gly Gly Gly Leu Val Gln
            20                  25                  30

Pro Gly Gly Ser Leu Lys Leu Ser Cys Ala Ala Ser Gly Phe Thr Phe
        35                  40                  45

Ser Ser Tyr Gly Met Ser Trp Val Arg Gln Thr Pro Asp Lys Arg Leu
    50                  55                  60

Glu Leu Val Ala Thr Ile Asn Ser Asn Gly Gly Arg Thr Tyr Tyr Leu
65                  70                  75                  80

Asp Ser Val Lys Gly Arg Phe Thr Ile Ser Arg Asp Asn Ala Lys Asn
                85                  90                  95

Thr Leu Tyr Leu Gln Met Ser Ser Leu Lys Ser Glu Asp Thr Ala Met
            100                 105                 110

Tyr Tyr Cys Ala Arg Asp Gly Gly Leu Leu Arg Asp Ser Ala Trp Phe
        115                 120                 125

Ala Tyr Trp Gly Gln Gly Thr Leu Val Thr Val Ser Ala
    130                 135                 140

<210> SEQ ID NO 28
<211> LENGTH: 384
<212> TYPE: DNA
<213> ORGANISM: Mus musculus
<220> FEATURE:
<221> NAME/KEY: CDS
<222> LOCATION: (1)..(384)

<400> SEQUENCE: 28 atg agg gcc cct gct cag att ttt gga ttc ttg ttg ctc tgg ttc cca    48
Met Arg Ala Pro Ala Gln Ile Phe Gly Phe Leu Leu Leu Trp Phe Pro
 1               5                  10                  15 ggt gcc aga tgt gaa atc cag atg acc cag tct cca tcc tct atg tct    96
Gly Ala Arg Cys Glu Ile Gln Met Thr Gln Ser Pro Ser Ser Met Ser
            20                  25                  30 gca tct ctg gga gac aga ata acc atc act tgc cag gca act caa gac    144
Ala Ser Leu Gly Asp Arg Ile Thr Ile Thr Cys Gln Ala Thr Gln Asp
        35                  40                  45 att gtt aag aat tta aac tgg tat cag cag aaa cca ggg aaa ccc cct    192
Ile Val Lys Asn Leu Asn Trp Tyr Gln Gln Lys Pro Gly Lys Pro Pro
    50                  55                  60
```

```
tca atc ctg atc tat tat gca act gaa ctg gca gaa ggg gtc cca tca    240
Ser Ile Leu Ile Tyr Tyr Ala Thr Glu Leu Ala Glu Gly Val Pro Ser
 65                  70                  75                  80 agg ttc agt ggc agt ggg tct ggg tca gac tat tct ctg aca atc agc    288
Arg Phe Ser Gly Ser Gly Ser Gly Ser Asp Tyr Ser Leu Thr Ile Ser
                 85                  90                  95 aac ctg gag tct gaa gat ttt gca gac tat tac tgt cta cag ttt tat    336
Asn Leu Glu Ser Glu Asp Phe Ala Asp Tyr Tyr Cys Leu Gln Phe Tyr
            100                 105                 110 gac ttt ccg ctc acg ttc ggt gct ggg acc aag ctg gag ctg aaa cgg    384
Asp Phe Pro Leu Thr Phe Gly Ala Gly Thr Lys Leu Glu Leu Lys Arg
        115                 120                 125

<210> SEQ ID NO 29
<211> LENGTH: 128
<212> TYPE: PRT
<213> ORGANISM: Mus musculus

<400> SEQUENCE: 29

Met Arg Ala Pro Ala Gln Ile Phe Gly Phe Leu Leu Leu Trp Phe Pro
 1               5                  10                  15

Gly Ala Arg Cys Glu Ile Gln Met Thr Gln Ser Pro Ser Ser Met Ser
            20                  25                  30

Ala Ser Leu Gly Asp Arg Ile Thr Ile Thr Cys Gln Ala Thr Gln Asp
        35                  40                  45

Ile Val Lys Asn Leu Asn Trp Tyr Gln Gln Lys Pro Gly Lys Pro Pro
    50                  55                  60

Ser Ile Leu Ile Tyr Tyr Ala Thr Glu Leu Ala Glu Gly Val Pro Ser
 65                  70                  75                  80

Arg Phe Ser Gly Ser Gly Ser Gly Ser Asp Tyr Ser Leu Thr Ile Ser
                 85                  90                  95

Asn Leu Glu Ser Glu Asp Phe Ala Asp Tyr Tyr Cys Leu Gln Phe Tyr
            100                 105                 110

Asp Phe Pro Leu Thr Phe Gly Ala Gly Thr Lys Leu Glu Leu Lys Arg
        115                 120                 125

<210> SEQ ID NO 30
<211> LENGTH: 420
<212> TYPE: DNA
<213> ORGANISM: Mus musculus
<220> FEATURE:
<221> NAME/KEY: CDS
<222> LOCATION: (1)..(420)

<400> SEQUENCE: 30 atg gga tgg agc tat atc atc ttc ttt ctg gta gca aca gct aca ggt     48
Met Gly Trp Ser Tyr Ile Ile Phe Phe Leu Val Ala Thr Ala Thr Gly
 1               5                  10                  15 gtg cac tcc cag gtc cag ctg cag cag tct ggg cct gag ctg gtg agg     96
Val His Ser Gln Val Gln Leu Gln Gln Ser Gly Pro Glu Leu Val Arg
            20                  25                  30 cct ggg gtc tca gtg aag att tcc tgc aag ggt tcc ggc tac aca ttc    144
Pro Gly Val Ser Val Lys Ile Ser Cys Lys Gly Ser Gly Tyr Thr Phe
        35                  40                  45 act gat tat gct acg cac tgg gtg agg cag agt cat gca aag agt cta    192
Thr Asp Tyr Ala Thr His Trp Val Arg Gln Ser His Ala Lys Ser Leu
    50                  55                  60 gag tgg att gga gtt att agt agt tac tct ggt aat aca aag tac aac    240
Glu Trp Ile Gly Val Ile Ser Ser Tyr Ser Gly Asn Thr Lys Tyr Asn
 65                  70                  75                  80
```

```
cag aac ttt aag gac aag gcc aca atg act gta gac aaa tcc tcc agc    288
Gln Asn Phe Lys Asp Lys Ala Thr Met Thr Val Asp Lys Ser Ser Ser
             85                  90                  95 aca gcc tat atg gaa ctt gcc aga ttg aca tct gag gat tct gcc atg    336
Thr Ala Tyr Met Glu Leu Ala Arg Leu Thr Ser Glu Asp Ser Ala Met
        100                 105                 110 tat tac tgt gca aga tat gat tac gac gtc cgg tac tat gct atg gac    384
Tyr Tyr Cys Ala Arg Tyr Asp Tyr Asp Val Arg Tyr Tyr Ala Met Asp
    115                 120                 125 tac tgg ggt caa gga acc tca gtc acc gtc tcc tca                    420
Tyr Trp Gly Gln Gly Thr Ser Val Thr Val Ser Ser
130                 135                 140
```

<210> SEQ ID NO 31
<211> LENGTH: 140
<212> TYPE: PRT
<213> ORGANISM: Mus musculus

<400> SEQUENCE: 31

```
Met Gly Trp Ser Tyr Ile Ile Phe Phe Leu Val Ala Thr Ala Thr Gly
 1               5                  10                  15

Val His Ser Gln Val Gln Leu Gln Gln Ser Gly Pro Glu Leu Val Arg
             20                  25                  30

Pro Gly Val Ser Val Lys Ile Ser Cys Lys Gly Ser Gly Tyr Thr Phe
         35                  40                  45

Thr Asp Tyr Ala Thr His Trp Val Arg Gln Ser His Ala Lys Ser Leu
     50                  55                  60

Glu Trp Ile Gly Val Ile Ser Ser Tyr Ser Gly Asn Thr Lys Tyr Asn
 65                  70                  75                  80

Gln Asn Phe Lys Asp Lys Ala Thr Met Thr Val Asp Lys Ser Ser Ser
             85                  90                  95

Thr Ala Tyr Met Glu Leu Ala Arg Leu Thr Ser Glu Asp Ser Ala Met
        100                 105                 110

Tyr Tyr Cys Ala Arg Tyr Asp Tyr Asp Val Arg Tyr Tyr Ala Met Asp
    115                 120                 125

Tyr Trp Gly Gln Gly Thr Ser Val Thr Val Ser Ser
130                 135                 140
```

<210> SEQ ID NO 32
<211> LENGTH: 8
<212> TYPE: PRT
<213> ORGANISM: Mus musculus

<400> SEQUENCE: 32

```
Ser Asn Gly Asn Thr Tyr Leu Tyr
 1               5
```

<210> SEQ ID NO 33
<211> LENGTH: 7
<212> TYPE: PRT
<213> ORGANISM: Mus musculus

<400> SEQUENCE: 33

```
Arg Met Ser Asn Leu Ala Ser
 1               5
```

<210> SEQ ID NO 34
<211> LENGTH: 9
<212> TYPE: PRT
<213> ORGANISM: Mus musculus

<400> SEQUENCE: 34

Met Gln His Leu Glu Tyr Pro Phe Thr
 1               5

<210> SEQ ID NO 35
<211> LENGTH: 5
<212> TYPE: PRT
<213> ORGANISM: Mus musculus

<400> SEQUENCE: 35

Thr Phe Gly Met Ser
 1               5

<210> SEQ ID NO 36
<211> LENGTH: 17
<212> TYPE: PRT
<213> ORGANISM: Mus musculus

<400> SEQUENCE: 36

Thr Ile Asn Ser Asn Gly Gly Arg Thr Tyr Tyr Leu Asp Ser Val Lys
 1               5                  10                  15

Gly

<210> SEQ ID NO 37
<211> LENGTH: 13
<212> TYPE: PRT
<213> ORGANISM: Mus musculus

<400> SEQUENCE: 37

Asp Gly Gly Leu Leu Arg Asp Ser Ala Trp Phe Ala Tyr
 1               5                  10

<210> SEQ ID NO 38
<211> LENGTH: 8
<212> TYPE: PRT
<213> ORGANISM: Mus musculus

<400> SEQUENCE: 38

Gly Asn Gly Asn Thr Tyr Leu Tyr
 1               5

<210> SEQ ID NO 39
<211> LENGTH: 7
<212> TYPE: PRT
<213> ORGANISM: Mus musculus

<400> SEQUENCE: 39

Arg Met Ser Asn Leu Ala Ser
 1               5

<210> SEQ ID NO 40
<211> LENGTH: 9
<212> TYPE: PRT
<213> ORGANISM: Mus musculus

<400> SEQUENCE: 40

Met Gln His Leu Glu Tyr Pro Phe Thr
 1               5

<210> SEQ ID NO 41
<211> LENGTH: 5
<212> TYPE: PRT
<213> ORGANISM: Mus musculus

```
<400> SEQUENCE: 41

Ser Tyr Gly Met Ser
1               5

<210> SEQ ID NO 42
<211> LENGTH: 17
<212> TYPE: PRT
<213> ORGANISM: Mus musculus

<400> SEQUENCE: 42

Thr Ile Asn Ser Asn Gly Gly Arg Thr Tyr Tyr Leu Asp Ser Val Lys
1               5                   10                  15

Gly

<210> SEQ ID NO 43
<211> LENGTH: 13
<212> TYPE: PRT
<213> ORGANISM: Mus musculus

<400> SEQUENCE: 43

Asp Gly Gly Leu Leu Arg Asp Ser Ala Trp Phe Ala Tyr
1               5                   10

<210> SEQ ID NO 44
<211> LENGTH: 11
<212> TYPE: PRT
<213> ORGANISM: Mus musculus

<400> SEQUENCE: 44

Gln Ala Thr Gln Asp Ile Val Lys Asn Leu Asn
1               5                   10

<210> SEQ ID NO 45
<211> LENGTH: 7
<212> TYPE: PRT
<213> ORGANISM: Mus musculus

<400> SEQUENCE: 45

Tyr Ala Thr Glu Leu Ala Glu
1               5

<210> SEQ ID NO 46
<211> LENGTH: 9
<212> TYPE: PRT
<213> ORGANISM: Mus musculus

<400> SEQUENCE: 46

Leu Gln Phe Tyr Asp Phe Pro Leu Thr
1               5

<210> SEQ ID NO 47
<211> LENGTH: 5
<212> TYPE: PRT
<213> ORGANISM: Mus musculus

<400> SEQUENCE: 47

Asp Tyr Ala Thr His
1               5

<210> SEQ ID NO 48
<211> LENGTH: 9
<212> TYPE: PRT
<213> ORGANISM: Mus musculus
```

```
<400> SEQUENCE: 48

Val Ile Ser Ser Tyr Ser Gly Asn Thr
  1               5

<210> SEQ ID NO 49
<211> LENGTH: 12
<212> TYPE: PRT
<213> ORGANISM: Mus musculus

<400> SEQUENCE: 49

Tyr Asp Tyr Asp Val Arg Tyr Tyr Ala Met Asp Tyr
  1               5                  10

<210> SEQ ID NO 50
<211> LENGTH: 3017
<212> TYPE: DNA
<213> ORGANISM: Homo sapiens

<400> SEQUENCE: 50
agcggggcga tgcccagcag ataagccagg caaacctcgg tgtgatcgaa gaagccaatt      60
tgagactcag cctagtccag gcaagctact ggcacctgct gctctcaact aacctccaca     120
caatggtgtt cgcatttttgg aaggtctttc tgatcctaag ctgccttgca ggtcaggtta    180
```

-continued

```
cggctcactg cggcctccgc tccctgggtt cgggcgattc tcctgcctgg gcctcctgag   1740
tggctgggac tgcaggcacg tgccgccacg cccggctaat tttttgtatt tttggtagag   1800
atggggtttc acgttgttgg ccaggatggt ctccatctcc tgacctcatg atccgcccac   1860
cttggcctcc caaaatgctg ggattacagg catgagccac tgcgcccggc ctcttttag    1920
ctactcttat gttccacatg cacatatgac aaggtggcat taattagatt caatattatt   1980
tctaggaata gttcctcatt cattttata ttgaccacta agaaaataat tcatcagcat    2040
tatctcatag attggaaaat tttctccaaa tacaatagag gagaatatgt aaagggtata   2100
cattaattgg tacgtagcat ttaaaatcag gtcttataat taatgcttca ttcctcatat   2160
tagatttccc aagaaatcac cctggtatcc aatatctgag catggcaaat ttaaaaaata   2220
acacaatttc ttgcctgtga ccctagcact ttgggaggcc gaggcaggtg gatcacctga   2280
ggtcaggggt tcgagaccag cctggccgac atggcgaagc cccttctctg ctaggaatgc   2340
agaaattggc tgggcgtggt ggtgcatgcc tgtagtcccg gctacttggg aggctgaggc   2400
aggagagtcg cttgaaccca gggggtggag gttgcagtga gccgagattg tgccactgca   2460
ctccaacctg ggtgacggag tgagattcca tctgaaaaac aaaaacaaaa acagaaaaca   2520
aacaaacaaa aaacaaaaaa tccccacaac tttgtcaaat aatgtacagg caaacacttt   2580
caaatataat ttccttcagt gaatacaaaa tgttgatatc ataggtgatg tacaatttag   2640
ttttgaatga gttattatgt tatcactgtg tctgatgtta tctactttga aaggcagtcc   2700
agaaaagtgt tctaagtgaa ctcttaagat ctattttaga taatttcaac taattaaata   2760
acctgtttta ctgcctgtac attccacatt aataaagcga taccaatctt atatgaatgc   2820
taatattact aaaatgcact gatatcactt cttcttccac tgttgaaaag ctttctcatg   2880
atcatatttc acccacatct caccttgaag aaacttacag gtagacttac cttttcactt   2940
gtggaattaa tcatatttaa atcttacttt aaggctcaat aaataatact cataatgtcc   3000
caaaaaaaaa aaaaaaa                                                  3017
```